US009320533B2

(12) United States Patent
Covello

(10) Patent No.: US 9,320,533 B2
(45) Date of Patent: Apr. 26, 2016

(54) DEVICES AND METHODS FOR MINIMALLY INVASIVE ACCESS TO SINUSES AND TREATMENT OF SINUSITIS

(76) Inventor: Leonard V. Covello, Munster, IN (US)

(*) Notice: Subject to any disclaimer, the term of this patent is extended or adjusted under 35 U.S.C. 154(b) by 882 days.

(21) Appl. No.: 12/804,398

(22) Filed: Jul. 20, 2010

(65) Prior Publication Data
US 2011/0021975 A1 Jan. 27, 2011

Related U.S. Application Data

(60) Provisional application No. 61/271,500, filed on Jul. 21, 2009.

(51) Int. Cl.
*A61B 17/24* (2006.01)
*A61B 17/295* (2006.01)
*A61B 17/3205* (2006.01)
(Continued)

(52) U.S. Cl.
CPC .............. *A61B 17/24* (2013.01); *A61B 17/295* (2013.01); *A61B 17/32053* (2013.01); *A61B 17/3468* (2013.01); *A61B 17/3478* (2013.01); *A61B 2019/4889* (2013.01); *A61M 25/1002* (2013.01)

(58) Field of Classification Search
CPC ............. A61B 17/24; A61B 2017/246; A61B 2017/248
USPC ...................... 606/184, 196, 199; 604/103.07
See application file for complete search history.

(56) References Cited

U.S. PATENT DOCUMENTS 3,948,254 A  4/1976 Zaffaroni
4,079,518 A  3/1978 Marshall
(Continued)

FOREIGN PATENT DOCUMENTS

DE 365099 12/1922
FR 2778839 11/1999

OTHER PUBLICATIONS

International Search Report of International Application No. PCT/US2010/042540; Dec. 3, 2010.
(Continued)

*Primary Examiner* — Nathan R Price
*Assistant Examiner* — Melissa A Snyder
(74) *Attorney, Agent, or Firm* — Goodwin Procter LLP

(57) ABSTRACT

The present invention provides minimally invasive devices and methods for accessing the sinuses and their surrounding structures for surgery and other treatments. The anterior ethmoid and maxillary sinuses are accessed and treated under minimal anesthesia with little or no postoperative limitation of activity or adverse symptoms. Direct visual verification of the sinuses and their natural ostia is utilized. Other paranasal sinuses may be treated by this method as well. The sinuses, in particular the maxillary and anterior ethmoid, are accessed via a direct anterior to posterior axis and the natural ostia of those sinuses is directly visualized for placement of a guide-free dilator, in the desired location within the natural ostia. That access to the maxillary ostium is accomplished by the anterior transuncinate "keyhole" approach in which a hole is punched in the uncinate process with the described devices according to the described methods. The properly placed dilator is expanded to allow drainage of the inflamed sinus and then withdrawn. An analogous ethmoid bulla "keyhole" approach and subsequent dilation are used for the anterior ethmoid sinus ostia. Pharmaceutical agents may be placed at desired locations in the sinuses using the same access technique.

16 Claims, 39 Drawing Sheets

(51) Int. Cl.
   *A61B 17/34*   (2006.01)
   *A61B 19/00*   (2006.01)
   *A61M 25/10*   (2013.01)

(56) References Cited

U.S. PATENT DOCUMENTS

| | | | |
|---|---|---|---|
| 4,909,250 A | 3/1990 | Smith | |
| 5,281,197 A | 1/1994 | Arias et al. | |
| 5,474,571 A | 12/1995 | Lang | |
| 5,766,151 A * | 6/1998 | Valley et al. | 604/103.07 |
| 5,782,747 A | 7/1998 | Zimmon | |
| 6,280,459 B1 * | 8/2001 | Doble | 606/206 |
| 6,527,734 B2 | 3/2003 | Cragg et al. | |
| 7,500,971 B2 | 3/2009 | Chang | |
| 7,520,876 B2 | 4/2009 | Ressemann | |
| 7,645,272 B2 | 1/2010 | Chang | |
| 7,654,997 B2 | 2/2010 | Makower | |
| 7,717,933 B2 | 5/2010 | Becker | |
| 7,740,642 B2 | 6/2010 | Becker | |
| 7,753,929 B2 | 7/2010 | Becker | |
| 7,753,930 B2 | 7/2010 | Becker | |
| 7,785,315 B1 | 8/2010 | Muni | |
| 2005/0113850 A1 | 5/2005 | Tagge | |
| 2006/0004286 A1 * | 1/2006 | Chang et al. | 600/435 |
| 2006/0149310 A1 * | 7/2006 | Becker | 606/196 |
| 2008/0015497 A1 * | 1/2008 | Keith et al. | 604/96.01 |
| 2008/0015540 A1 * | 1/2008 | Muni et al. | 604/500 |
| 2008/0015626 A1 | 1/2008 | Keith | |
| 2008/0097295 A1 | 4/2008 | Makower et al. | |
| 2008/0281300 A1 | 11/2008 | Morriss | |
| 2009/0082799 A1 | 3/2009 | Haunschild | |
| 2009/0177272 A1 | 7/2009 | Abbate et al. | |
| 2009/0216196 A1 | 8/2009 | Drontle | |
| 2010/0076269 A1 * | 3/2010 | Makower | A61B 1/233 600/178 |

OTHER PUBLICATIONS

Roelof, Moers, Extended European Search Report for Application No. PCT/US2010042540, Jun. 8, 2015, European Patent Office.

* cited by examiner

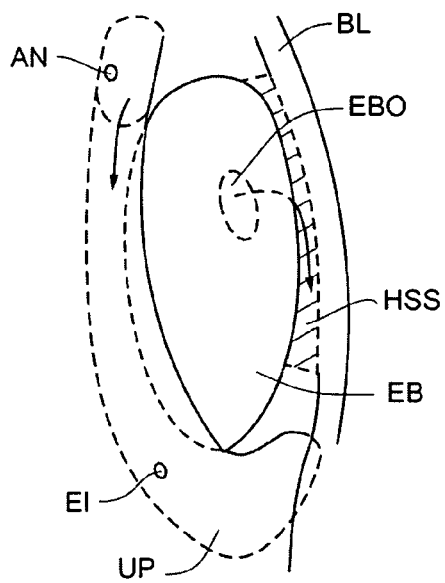
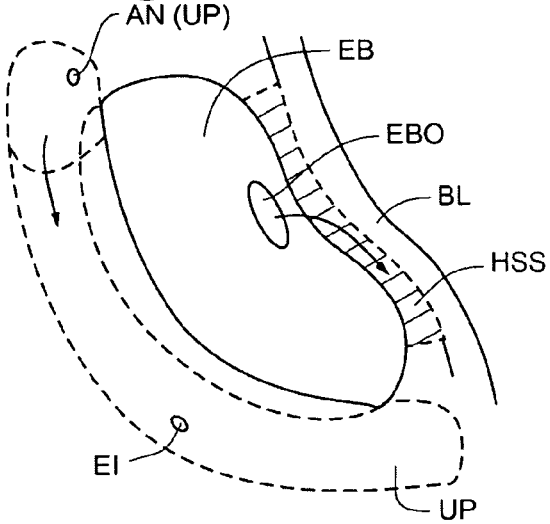
Fig. 21A
Fig. 21B
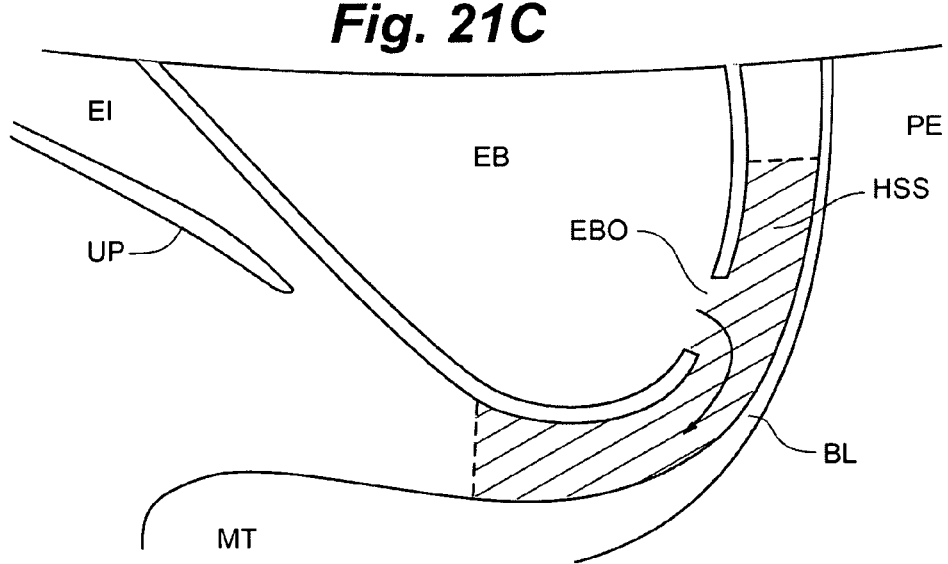
Fig. 21C

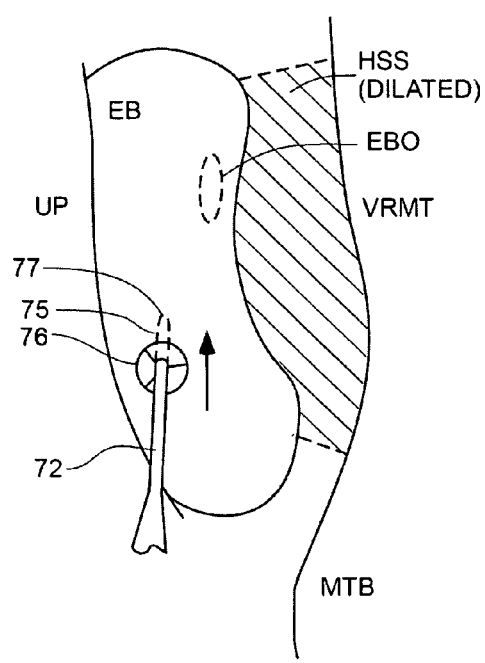
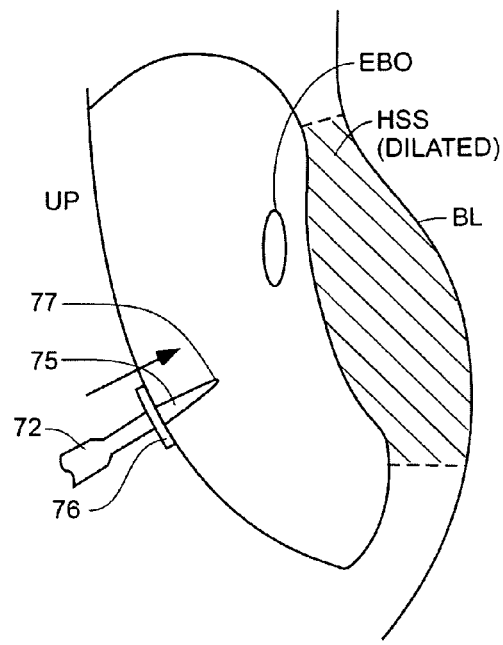
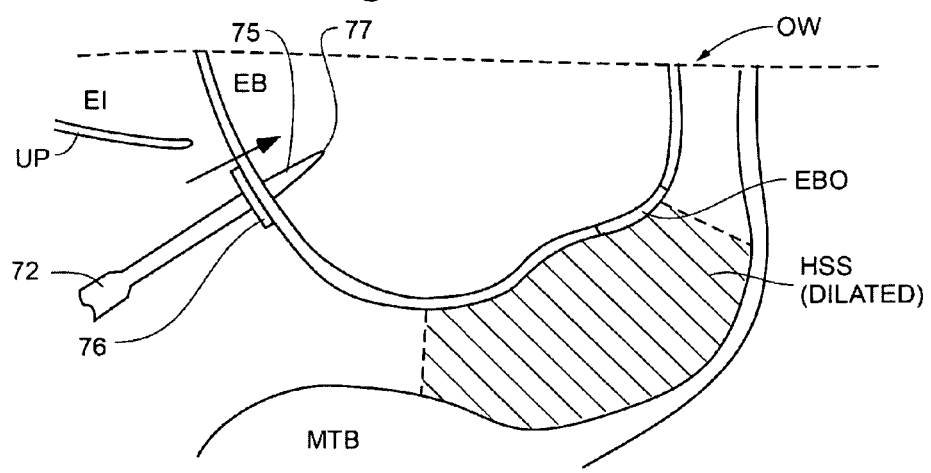

DEVICES AND METHODS FOR MINIMALLY INVASIVE ACCESS TO SINUSES AND TREATMENT OF SINUSITIS

CROSS-REFERENCE TO RELATED APPLICATION

This application claims the benefit under 35 U.S.C. 119(e) of U.S. Provisional Application No. 61/271,500, filed on Jul. 21, 2009, the contents of which are incorporated herein by reference.

FIELD OF INVENTION

The present invention relates to minimally invasive devices, systems and methods for accessing the sinuses of a human patient and for treating sinusitis.

BACKGROUND OF INVENTION

There are a substantial number of people with sinus inflammatory disease—sinusitis—that could benefit from sinus surgery. Patients with sinusitis can be grouped according to the severity of their sinusitis into those with mild and those with severe anatomic evidence of sinusitis. The latter category includes those patients with significant anatomic anomalies, patients previously operated on who have substantial postoperative defects in the diseased areas, and those with significant paranasal sinus polyps. The remaining group with mild anatomic evidence of inflammation, which makes up the largest portion of those suffering from sinusitis, may nonetheless have significant and persistent symptoms despite undergoing medical therapies. Many patients are understandably resistant to traditional surgery, such as functional endoscopic sinus surgery (FESS), in particular if their symptoms are mild. Thus, that is the target group for non-invasive treatments. The goal is a procedure that is reliable, long lasting, pain free, safe, has no tissue removal, and allows an immediate return to full activities.

Development of non-invasive procedures requires an understanding of the anatomical features of the sinuses and the nasal cavity as well as an appreciation of the mucus drainage pathways. Clinically, there are five major groups of sinuses in a human patient: frontal, anterior ethmoid, posterior ethmoid, maxillary, and sphenoid. The ethmoid is divided into anterior and posterior portions to account for the clinical observation that sinus cells anterior to the basal lamella (the lateral attachment of the middle turbinate) have a separate mucus drainage pathway from those posterior to the basal lamella. The maxillary, anterior ethmoid and frontal sinuses often are affected by inflammatory disease in unison. That tendency is believed by some to be due to a shared common drainage location; in any case, current dogma holds that inflammation in the anterior ethmoid is an indication of inflammation in the maxillary and frontal sinuses. For the maxillary sinus, the drainage site is the ethmoid infundibulum, the very narrow space between the uncinate process medially and the orbit laterally. For drainage of the anterior ethmoid sinuses, there are multiple sites, usually including the ethmoid infundibulum for a small portion, and relying on the hiatus semilunaris superior for most of the cells. That anatomic observation is not universally known to routine practitioners of the current art. For the frontal sinus, the ostium usually just posteromedial to the superior end of the uncinate (or just external to the ethmoid infundibulum proper), but sometimes is lateral to the uncinate, and therefore within the infundibulum. That slight anatomic separation coheres with the clinical observation that the maxillary and anterior ethmoid are very frequently inflamed in unison, with the frontal sinus also inflamed somewhat less often.

The posterior ethmoid and sphenoid sinuses are believed to have individual drainage sites posterior to the basal lamella. For the sphenoid, it is indisputable—the ostium can be easily seen at the sphenoid rostrum in nearly every patient if proper exposure can be obtained. For the posterior ethmoid, the putative drainage sites are not so explicit. There is some sharing of inflammatory disease by the sphenoid and posterior ethmoid sinuses. Analogous to the maxillary/anterior ethmoid/frontal system, it is believed that there is a shared pathway for the posterior ethmoid and sphenoid sinuses in the sphenoethmoid recess, the space just anterior to the sphenoid rostrum (where, as noted above, the sphenoid ostium is found) and extending laterally. (Stammberger, H. *Functional Endoscopic Sinus Surgery*. Mosby (St. Louis) 1991. See pp. 49-67.)

The vast majority of the patient group with mild anatomic sinusitis, regardless of symptom severity, has maxillary or anterior ethmoid inflammation, which also is referred to as limited maxillary and anterior ethmoid disease. If a minimally invasive treatment is to be effective for a majority of patients, it must be effective for patients with maxillary or anterior ethmoid inflammation.

The Maxillary Sinus

The maxillary sinus is a large air space, filling essentially the entire cheekbone in the typical patient. From the transnasal aspect, that air space lies just lateral to the entire lower half of the lateral wall of the nose. From the oral/sublabial aspect, it lies just superior to the tooth roots from the canine to the last molar and extends to the orbit. The maxillary sinus is relatively large and most of it is relatively far from the eye, which is the most important structure in that area. Traditional access to the maxillary sinus involved either forcing a trocar through the low lateral nasal wall or sublabially through the anterior wall of the sinus just lateral to the canine root or both, followed by the enlargement of the resulting hole via removal of bone to drain the sinus and remove any diseased tissue. Those approaches were developed to best avoid damaging the eye, yielding a suitable surgical margin of error for that purpose. At the end of the procedure, one sought to preserve the intranasal hole in the belief that the sinus would continue to drain through it for the rest of the patient's life, an assumption later realized to be incorrect.

A seminal development in sinus surgery was Messerklinger's work in the 1960's (and applied clinically in the 1980's) on the physiology of sinus clearance of mucus, and its rather rigid connection to sinus microanatomy. (Messerklinger, W., multiple references quoted in Stammberger, ibid., pp. 27-28.) Among other observations, Messerklinger's work involved placing traceable, visible granules into the maxillary sinuses. Using a high resolution endoscope, he observed that the granules would migrate along the lining in a very specific path, exiting the maxillary sinus through an ostium near the anterior superior extreme of the sinus, lateral to the uncinate process, and following an explicit and narrow stream just above the inferior attachment of the uncinate to the lateral wall, before exiting that narrow space posteriorly. Of crucial interest, that pathway was preserved independent of any other, even larger, holes that might exist, naturally or surgically, in the medial wall of the sinus. In effect, the cilia always push sinus mucus in the direction of the so-called natural ostium, whether or not other ostia exist or are created. That observation suggested that the previously-held belief in the benefit of surgically-created sinus ostia was misplaced. The new paradigm was to become surgical enlargement of the natural ostium explicitly, finally gaining wide adoption in the early 1990's with utilization of functional endoscopic sinus surgery (FESS), particularly among new trainees and professors. That strategy subsequently has been validated clinically. Placement of ostia elsewhere was too often found to be useless or injurious and, crucially, those problems could be reliably corrected only by addressing the natural ostium in an appropriate way. That principle continues to be important, beneficially if honored, detrimentally if neglected.

In state-of-the-art endoscopic maxillary sinus surgery today, the uncinate process first is removed from its posterior margin back to its anterior maxillary attachment, revealing the (often small) natural ostium just posterior to the anterior maxillary attachment. The natural ostium is assessed. If deemed too small to effectively permit long-term drainage from the sinus (an arbitrary decision), it is enlarged posteriorly. In approximately one-third of patients, there is a naturally occurring accessory ostium posterior to the natural ostium. In those patients, the surgeon enlarges the natural ostium to broadly connect with and encompass the accessory ostium to avoid having mucus recirculate; i.e., to prevent mucus that is exiting the sinus via the augmented natural ostium from reentering via the accessory ostium. It is not clear how often that pathway is utilized for recirculation, if ever. A problem results, however, if a surgeon creates a new ostium posterior to the natural ostium, which often does cause recirculation, or if a surgeon enlarges an accessory ostium thinking it to be the natural one, which will not achieve the objective and might, as discussed above, cause recirculation. If those errors occur, they usually can be corrected by finding the natural ostium and connecting it with the accessory ostium to create a single large ostium.

The minimally invasive balloon sinuplasty surgical method for application to the maxillary sinus, as exemplified by the transnasal approach of U.S. Pat. No. 7,500,971, which is incorporated herein by reference in its entirety, involves placing a curved, tubular guide into the posterior slit-like opening of the infundibulum, between the posterior margin of the uncinate medially and the orbital wall laterally. A guide wire is then fed through the lumen of the tube and into the infundibulum. The wire is gently manipulated until it, by trial and error, drops into the ostium. The tip can be verified to be in the sinus by X-ray fluoroscopy or more commonly by light from the wire tip seen to transilluminate the cheek. See, e.g., U.S. Pat. No. 7,559,925. Both X-ray fluoroscopy and transillumination are cumbersome to a degree, fluoroscopy especially so as it requires large machines that are not normally present at sinus surgery and get in the way of easy, interruption-free operating. The wire transillumination method is more convenient, but requires the surgeon to juggle instruments in his/her hands and creates tangles on an operative field already wound with a variety of suction hoses and cords. Fluoroscopy and transillumination can assist the surgeon in determining if the instrument is in the sinus, but do not indicate whether the instrument is in the natural ostium. Thus, they are not substitutes for direct visualization. The balloon catheter is passed through the lumen of the tubular guide over the wire until it is believed to be spanning the ostium at which point it is expanded, putatively stretching the ostium and spreading the space between the orbit and uncinate by stretching the uncinate medially. As noted above, that action may instead result in dilation of an accessory ostium.

Another minimally invasive sinuplasty method, as exemplified by the canine fossa approach of U.S. Pat. No. 7,520, 876, which is incorporated herein by reference in its entirety, utilizes the older sublabial approach to the maxillary sinus (described above), which requires puncturing the bone of the alveolus just above the tooth roots in the canine fossa region. The anterior wall of the maxillary sinus is punctured a bit lateral to the canine root. A miniature endoscope is passed coaxially through a tubular guide and advanced into the sinus and the natural ostium is directly visualized from this lateral aspect. The balloon catheter is passed into the ostium by manipulation of the guide according to what is visualized with the endoscope and the balloon is expanded.

Both the transnasal and canine fossa approaches have disadvantages. In the transnasal approach, the advance to the infundibulum is awkward. Surgical instrumentation—including the guides, balloon catheter, endoscope and guide wire—is introduced into the nose from anterior to posterior, but the infundibulum is entered posteriorly and the wire advanced anteriorly from that point. Those two maneuvers necessitate a 180 degree turn of the guide, guide wire and balloon catheter that is difficult to execute atraumatically in the tight spaces involved.

Another substantial problem with the transnasal approach is that the method is performed blindly because the surgeon's view of the natural ostium and any intervening accessory ostia is blocked by the more medial uncinate. The instrumentation is rounded and made flexible to avoid inadvertent introduction into the eye. However, that does not prevent inadvertent introduction into and cannulation of an accessory ostium, rather than the natural ostium, caused by the surgeon's inability to see the position of the instrument. In fact, in the significant number of cases that an accessory ostium is present (estimated at about one third of all patients), the accessory ostium is encountered first by the guide wire, as it is more posteriorly placed, and is probably more likely to be dilated than the natural ostium. In such cases, the surgeon mistakenly enlarges the accessory ostium rather than the natural ostium. As discussed above, that is not helpful and often harmful. Protecting against that eventuality is difficult. It is common, therefore, for surgeons to resort to a "hybrid" invasive/non-invasive procedure in which the lower uncinate is surgically removed to visualize the natural ostium in the usual fashion. Performed appropriately by a competent surgeon, the "hybrid" approach solves the problem, but necessitates reverting to an essentially standard approach that is more than minimally invasive. Using a balloon to dilate the now visible natural ostium is of questionable benefit compared to the standard surgical approach of trimming the posterior margin of the ostium—likely a mere victory of style over substance. Surgeons that would prefer a minimally invasive method will often revert to the unsatisfactory "hybrid" procedure because of frustration with the awkward approach to the natural ostium or because of concern that they will inadvertently and unknowingly dilate the wrong (accessory) ostium.

The canine fossa approach offers the advantage that the surgeon accesses the maxillary sinus and views the ostia from inside the sinus, from which they can be seen unobstructed. If more than one ostium exists, the natural ostium will be the anterior one, so verification of the natural ostium and avoidance of the accessory ostium is possible. The route also is direct. It does not require a 180 degree turn. Proponents of the canine fossa approach of U.S. Pat. No. 7,520,876 further represent that the balloon dilation succeeds in also enlarging the ethmoid infundibulum in that it stretches the uncinate medially, and it certainly seems that it does so. They claim that balloon dilation of the ethmoid infundibulum, in addition to treating the maxillary sinus, results in treating the primary ethmoid drainage, which apparently is believed to be located in the ethmoid infundibulum. The anatomic evidence, however, is overwhelmingly against that possibility.

Nonetheless, the problems with the canine fossa approach are substantial. It requires a separate incision and access for a trocar under the lip. Thus, it is not easily and naturally combined with intranasal procedures. Moreover, it is more difficult or impossible to access the ethmoid, frontal, and sphenoid sinuses from the canine fossa access site. Access to the anterior ethmoid is possible, but cumbersome. Access to the frontal sinus is quite difficult, and access to the posterior ethmoid and sphenoid is virtually impossible. Surgeons must utilize another "hybrid" invasive/non-invasive procedure for those sinuses that require a second incision site and a cumbersome combination of nasal and oral procedures. The primary incision required by the canine fossa approach might be undesirable to patients seeking less rather than more surgery. Surgeons likewise might hesitate to embrace it.

The canine fossa procedure also utilizes a miniature endoscope. The image quality of the miniature endoscopes that are commercially available are suboptimal due to the very fine fiberoptic thread transmitting the image. The endoscope is understandably fragile with a short (25 procedures) life and therefore carries a rather high cost per use.

In sum, there is a need for a minimally invasive method to access and dilate the natural ostium of the maxillary sinus, preferably via transnasal access, without commonly resorting to traditional resection as a "hybrid" rescue during the procedure. Access to the natural ostium should be direct and not awkward so as to not frustrate the surgeon and to avoid trauma, should be verifiable, and should be easy to combine with minimally invasive approaches to the other sinuses.

The Anterior Ethmoid

The drainage pathways of the anterior ethmoid sinus are less explicitly defined than in the maxillary sinus. The ethmoid sinuses, anterior and posterior, are often referred to as a labyrinth. Unlike the maxillary sinus, the ethmoid is partitioned into many small contiguous cells, with the anterior cells draining anterior to the basal lamella (and containing more and smaller chambers) and the posterior cells draining posterior to the basal lamella (and containing one to three or so larger chambers). The labyrinth occupies roughly the upper half of the nose, is bounded superiorly by the rather thin skull base (and brain beyond), and laterally by the orbit. Landmarks are less explicit and more variable than those in the maxillary sinus area. Consequently, serious injuries to the eye and brain during sinus surgery can occur in approaches to the ethmoid.

Traditional invasive ethmoid surgery utilized an incision between the eye and the nose and a puncture of the medial wall of the orbit to access the ethmoid. The surgeon penetrated the ethmoid sinuses below the frontoethmoid suture line (which lies roughly at the equator of the orbit at the level of the corner of the eye) to avoid the brain while removing pieces of ethmoid bone and nasal lining. That approach was rendered obsolete for most cases in the 1990's with the maturation of endoscopic sinus surgery.

In the current standard of endoscopic surgery of the anterior ethmoid, the largest and most prominent cell of the anterior ethmoid, the ethmoid bulla, is opened and its walls and those of adjacent cells are removed until opened "enough" (an arbitrary designation). Experience has shown that the opening of the ethmoid bulla and those adjacent cells fixes mild sinusitis satisfactorily in most cases.

Minimally invasive methods for ethmoid surgery have not progressed as far as those methods for maxillary surgery. This deficiency is likely due to the significant anatomic variation of the anterior ethmoid anatomy and confusion within the field as to the location of its mucus outlets. The accepted minimally invasive paradigm would require that one identify and open those outlets, an objective only partially accomplished (usually without specific identification) in the routine art by resecting most of the septations of the anterior ethmoid, and not yet addressed in the prior balloon-dilation art.

One relatively new method in the minimally invasive realm avoids the anatomic variation problem entirely by circumventing the paradigm of dilating natural ostia. Instead, in this method, the ethmoid bulla is engaged with a trocar that is pushed through its anterior and posterior walls, into the posterior ethmoid. A reservoir is then passed into the tunnel to rest in the anterior and posterior ethmoid. The reservoir contains steroid that elutes into the sinus over days-to-weeks, decreasing inflammation.

It is reasonable to speculate that application of targeted pharmacotherapeutic agents, as in the above method, will be a helpful adjunct to the treatment of sinusitis. In the current routine sinus art, topical steroid spray is a mainstay of treatment, and topical antibiotics and antifungals are occasionally used to treat select patients. The benefits from these topical agents, however, have been limited. There is reason to suspect that the limitation is due to an inability to direct the agents to the diseased areas of intact sinuses in sufficient concentrations to be effective, rather than to some more fundamental shortcoming. In an analogous situation, acute and chronic infections and inflammation of the ear canal skin are much more rapidly and effectively treated with topical agents than with oral ones. Topical medications probably result in local pharmaceutical concentrations that are several orders of magnitude greater than those safely achievable in oral administration. Obviously, the ear canal is more easily targeted with repeated administration of concentrated therapeutic agents than the more hidden recesses of the paranasal sinuses.

The aforementioned placement of a pharmaceutical-eluting implantable device seeks to surmount that largely anatomic challenge, and has achieved some promising early results. There are certainly some drawbacks to this method, however. The placement of the device alters anterior ethmoid anatomy without explicit attention to the natural drainage pathways thereof, possibly, although not necessarily, compromising mucus clearance in the long-term. Taken together, the cost of the device and the nature of its placement do not lend themselves to repeated use in an office setting; rather, they are more suited to a single treatment or very occasional treatments in a surgical setting. As many patients have some degree of ongoing medical sinus disease, this is a significant drawback. Ideally, one would prefer that targeted pharmacotherapy be a viable alternative to oral therapy for many patients, necessitating a more convenient and inexpensive option. Lastly, the method by which the trocar is directed into the sinuses is of some concern. One would prefer, if possible, a more precise and less traumatic means of accessing the ethmoid sinuses. A reliable means to treat the maxillary sinus with targeted pharmacotherapy would also be desirable, an option lacking in the prior art. This gap in current treatment options is largely because of the presence of the uncinate, which prevents direct atraumatic access to the maxillary sinus, frustrating the guide-based system currently used.

In sum, there is a need for a minimally invasive method for accessing and treating the anterior ethmoid that augments flow through natural drainage pathways of the anterior ethmoid. There further is a need for a minimally invasive means to introduce targeted pharmacotherapeutic agents to the maxillary and anterior ethmoid sinuses (as well as others) in a more cost-effective and atraumatic manner than in the current art.

SUMMARY OF INVENTION

The present invention provides devices and methods to refine the existing minimally invasive methods for accessing the sinuses and their surrounding structures for surgery and other treatments. In preferred embodiments of the present invention, the anterior ethmoid and maxillary sinuses are accessed in a minimally invasive manner for treating mild inflammatory disease of those spaces, enabling surgical treatment for mild-to-moderate sinusitis to be performed under minimal anesthesia in an office setting, if desired, and with little or no postoperative limitation of activity or adverse symptoms. To facilitate broad application, the devices of the present invention have a form and maneuverability similar to those used routinely by practitioners of endoscopic sinus surgery so that the methods of the present invention can be easily taught, learned, and executed.

In one aspect of the present invention, a method of treating a congested maxillary sinus via a minimally invasive intranasal approach includes making a perforation ("keyhole") in the uncinate process, inserting a guide-free dilator through the keyhole perforation and dilating the natural ostium of the maxillary sinus or the ethmoid infundibulum.

In another aspect of the present invention, a method of treating a congested anterior ethmoid sinus pathway via a minimally invasive intranasal approach includes dilating the hiatus semilunaris superior, making a perforation ("keyhole") in the thin wall surrounding the ethmoid bulla, inserting a guide-free catheter through the keyhole perforation and dilating the ethmoid bulla ostium.

In another aspect of the present invention, a method of opening a constricted ethmoid sinus passageway includes introducing a probe into the nose, engaging the ethmoid bulla ostium, stretching the ethmoid bulla ostium, introducing a guide-free dilator into the hiatus semilunaris superior and dilating the hiatus semilunaris superior.

In yet another aspect of the present invention, a method of opening a constricted ethmoid sinus passageway includes introducing a probe into the nose, engaging the ethmoid bulla ostium, stretching the ethmoid bulla ostium, introducing a guide-free dilator into the hiatus semilunaris superior, dilating the hiatus semilunaris superior, making a perforation ("keyhole") in the thin wall surrounding the ethmoid bulla, inserting a guide-free catheter through the keyhole perforation and dilating the ethmoid bulla ostium.

In yet another aspect of the present invention, a method of introducing an active agent into a constricted maxillary sinus includes making a perforation ("keyhole") in the uncinate process, inserting a drug delivery device containing the active agent through the keyhole, and eluting the drug in the maxillary sinus.

In yet another aspect of the present invention, a method of introducing an active agent into a constricted anterior ethmoid sinus, particularly the ethmoid bulla, includes making a perforation ("keyhole") in the wall of the ethmoid bulla, inserting a drug delivery device containing the active agent through the keyhole, and eluting the drug in the sinus.

In still another aspect of the present invention, a method of retracting the middle turbinate includes introducing a middle turbinate retractor into the axilla of the middle meatus and expanding the middle turbinate retractor to retract the middle turbinate.

Another aspect of the present invention includes a middle turbinate retractor comprising two rigid parallel platforms composed of metal or plastic and a metal or plastic spring situated between the rigid platforms and a pair of forceps on the outer surfaces of the parallel platform that allow for expansion and compression of the spring.

Another aspect of the present invention includes a middle turbinate retractor comprising two parallel arms that are capable of being expanded or compressed with respect to each other, said arms crossing each other, thereby forming an upper portion and a lower portion, a pair of expansion receptacles at the lower portion of each arm, whereby squeezing of said expansion receptacles results in expansion of the parallel arms and a ratchet arm connected at the upper portion of each parallel arm capable of holding the parallel arms in place.

Another aspect of the present invention includes a hole punch capable of making a perforation in the uncinate process comprising a shaft, a stationary platform mounted on the shaft, a blade attached to one end of the stationary platform, a mobile tapered flange containing a receptacle pivotally connected to the stationary platform, and a means of bringing the blade of the stationary platform and the receptacle of the mobile tapered flange together, thereby generating a perforation in the uncinate process.

Yet another aspect of the present invention includes a guide-free dilator comprising a rigid shaft with a bottom portion and a top portion, a rigid handle mounted at the bottom portion of the rigid shaft, and a dilator segment mounted at the top portion of the rigid shaft. The dilator segment is comprised of a semiridgid shaft and a mounting balloon. In one embodiment, top portion of the rigid shaft is angled in the range of from about 30 degrees to about 60 degrees.

Still another aspect of the present invention includes a medial ethmoid probe comprising a handle having a top portion and a bottom portion and a shaft having a proximal segment and a distal segment, said proximal segment comprising a rigid material mounted on the top portion and the bottom portion of the handle and said distal segment comprising a semirigid material with a curved tip to engage an ostium in the ethmoid bulla. Preferably, the distal segment of the shaft curves to an angle ranging from about 30 degrees to about 60 degrees.

Still another aspect of the present invention includes a probe capable of making a perforation in the wall of the ethmoid bulla comprising a handle having a top portion and a bottom portion, an upper shaft mounted on the top portion of said handle, a lower shaft mounted on the bottom portion of said handle, and a perforator tip with a stop collar, said perforator tip mounted on the upper shaft.

Yet another aspect of the present invention includes a drug insertion device comprising a rigid shaft containing a lumen, said rigid shaft angled distally at an angle between about 55 degrees and about 60 degrees, a piston coaxial with and guided by said lumen of said rigid shaft, a receptacle for holding a drug or drug delivery device, said receptacle mounted at the distal end of the rigid shaft, and a means for moving the piston through the lumen of the rigid shaft to the receptacle, causing release of the drug or drug delivery device.

Still another aspect of the present invention includes a device for controlled delivery of a drug into a sinus, comprising a drug containing matrix and a degradable framework having a spine and a series of coplanar ribs protruding radially from the spine, the tips of the ribs protruding past the outer surface of the drug containing matrix, wherein the drug containing matrix degrades at a rate faster than the degradable framework.

Still another aspect of the present invention includes a device for controlled delivery of a drug into a sinus comprising a drug containing matrix and a degradable framework having a spine and an umbrella of ribs attached to the spine, said umbrella is on the outside surface of the drug containing matrix, wherein the umbrella expands upon insertion into the sinus and wherein the drug containing matrix degrades at a rate faster than the degradable framework.

BRIEF DESCRIPTION OF DRAWINGS

FIG. 21A illustrates the typical anteroinferomedial-to-posterosuperolateral view obtained during nasal endoscopy, FIG. 21B illustrates a medial-to-lateral sagittal view of the relevant structures of the middle meatus.

FIG. 21C illustrates a transverse view from superior-to-inferior of the relevant structures of the middle meatus.

FIGS. 28A-28C illustrate three views (endoscopic, sagittal, traverse) of using the ethmoid keyhole probe of the present invention to make a perforation in the wall of the ethmoid bulla.

DETAILED DESCRIPTION OF INVENTION

The following sections describe exemplary embodiments of the present invention. It will be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments or modifications thereof are contemplated as falling within the scope of the present invention as defined herein and equivalents thereto.

Throughout the description, if items are described as having, including, or comprising one or more specific components, or if processes and methods are described as having, including, or comprising one or more specific steps, it is contemplated that, additionally, there are items of the present invention that consist essentially of, or consist of, the one or more recited components, and that there are processes and methods according to the present invention that consist essentially of, or consist of, the one or more recited processing steps.

It should be understood that the order of steps or order for performing certain actions is immaterial, as long as the invention remains operable. Moreover, two or more steps or actions may be conducted simultaneously. Scale-up or scale-down of systems, processes, units, and/or methods disclosed herein may be performed by those of skill in the relevant art.

The invention provides novel devices and methods for accessing the sinuses and their surrounding structures for surgery and other treatments. The devices and methods are useful in the treatment of mild or severe sinusitis. The devices of the present invention have a form and maneuverability that will be suitable for routine use by current practitioners of endoscopic sinus surgery so that the methods of the present invention can be easily taught, learned, and executed. The methods of the present inventions are substantially non-invasive or minimally invasive and are pain free, safe and long lasting. The methods of the present invention can be performed under minimal anesthesia in an office setting, if desired, and with little or no postoperative limitation of activity or adverse symptoms.

In the figures described below, various anatomical structures of the sinuses and nasal cavity are displayed.

The following reference letters are used in the diagrams to show these anatomical features.

Figure 1A:
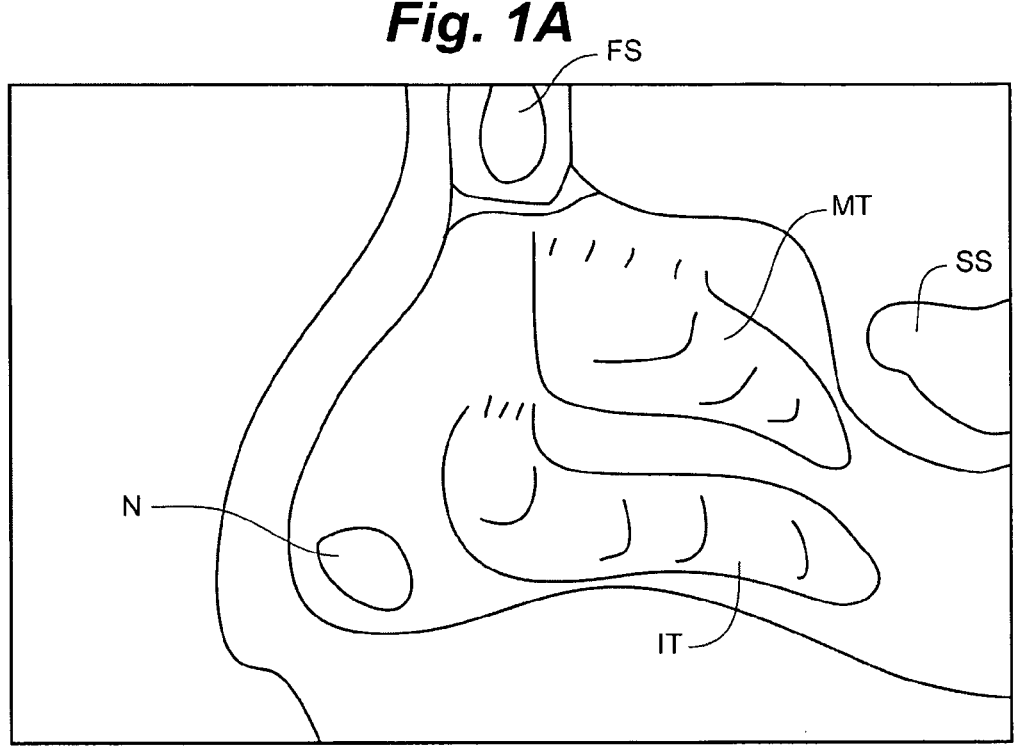
FIG. 1A-1C illustrate a sagittal view of the lateral nasal wall with various anatomical features thereof.

AAUP anterior attachment of the uncinate process
AN agger nasi cell
AO accessory ostium
BL basal lamella
EB ethmoid bulla
EBO ethmoid bulla ostium
EI ethmoid infundibulum
FS frontal sinus
FO frontal ostium
HSS hiatus semilunaris superior
IAUP inferior attachment of the uncinate process
IT insferior turbinate
KH keyhole
LF lacrimal fossa
LP lacrimal prominence
LW lateral wall
MS maxillary sinus
MSA maxillary sinus antrum
MT middle turbinate
MTB middle turbinate body
N nostril
NOMS natural ostium of the maxillary sinus OW orbital wall
OZ ostial zone
PAUP posterior attachment of the uncinate process
PE posterior ethmoid
PRMT posterior root of middle turbinate
SRMT superior root of middle turbinate
SS sphenoid sinus
UKP uncinate keyhole punch
UP uncinate process
VRMT vertical root of the middle turbinate A brief initial overview of some of the relevant anatomy is in order. In FIG. 1A, the right side of the nose is represented in a medial-to-lateral sagittal view. The diagram depicts the nostril (N), the interior turbinate (IT), the middle turbinate (MT), the frontal sinus (FS) and the sphenoid sinus (SS). The crucial structures to be manipulated in the method of the present invention lie lateral to the middle turbinate (MT). If the middle turbinate is reflected superiorly for clarity (FIG. 1B), we see the largest cell of the ethmoid complex, the ethmoid bulla (EB) and, anterior-inferior to it, the uncinate process (UP). Manipulation of the ethmoid bulla (EB) will be outlined in the description of the method below. The opening of the maxillary sinus, its natural maxillary ostium (NOMS), lies just lateral to the anterior-inferior attachment of the uncinate and can be seen if we remove the uncinate, again for clarity (FIG. 1C). It should be apparent from this discussion that both the middle turbinate (MT) and uncinate process (UP) comprise physical and visual barriers to manipulations of the ethmoid bulla (EB) and natural ostium of the maxillary sinus (NOMS). The method and devices of the present invention are designed accordingly, to address and remedy these challenges.

Retraction of the Middle Turbinate

Figure 1B:
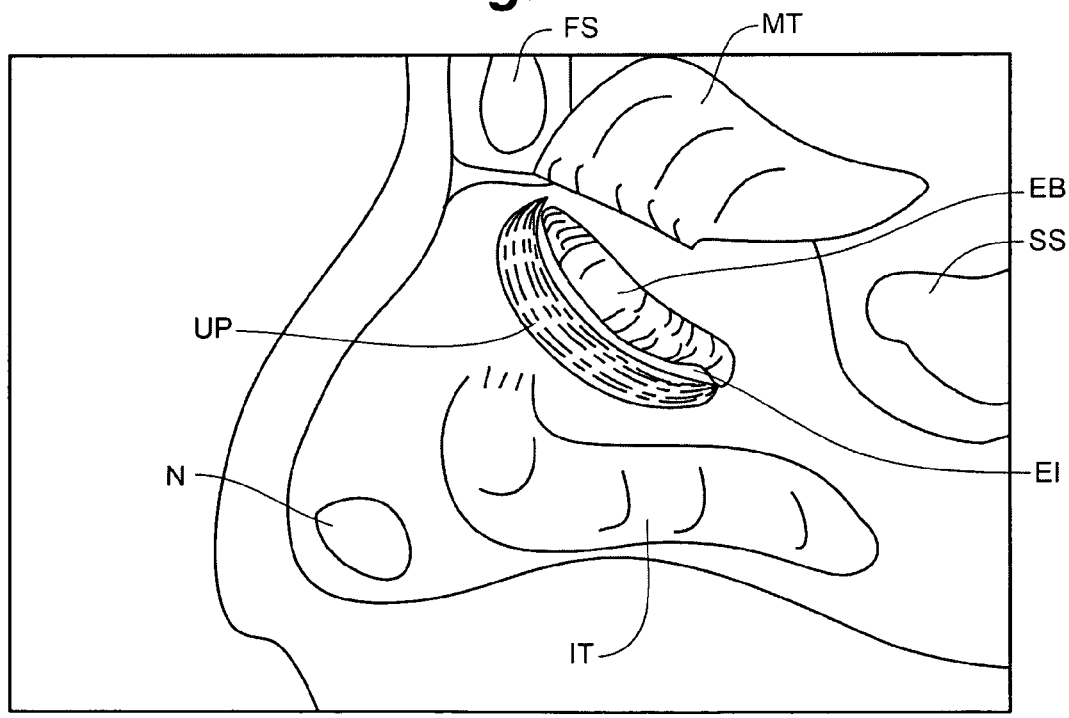
Figure 1C:
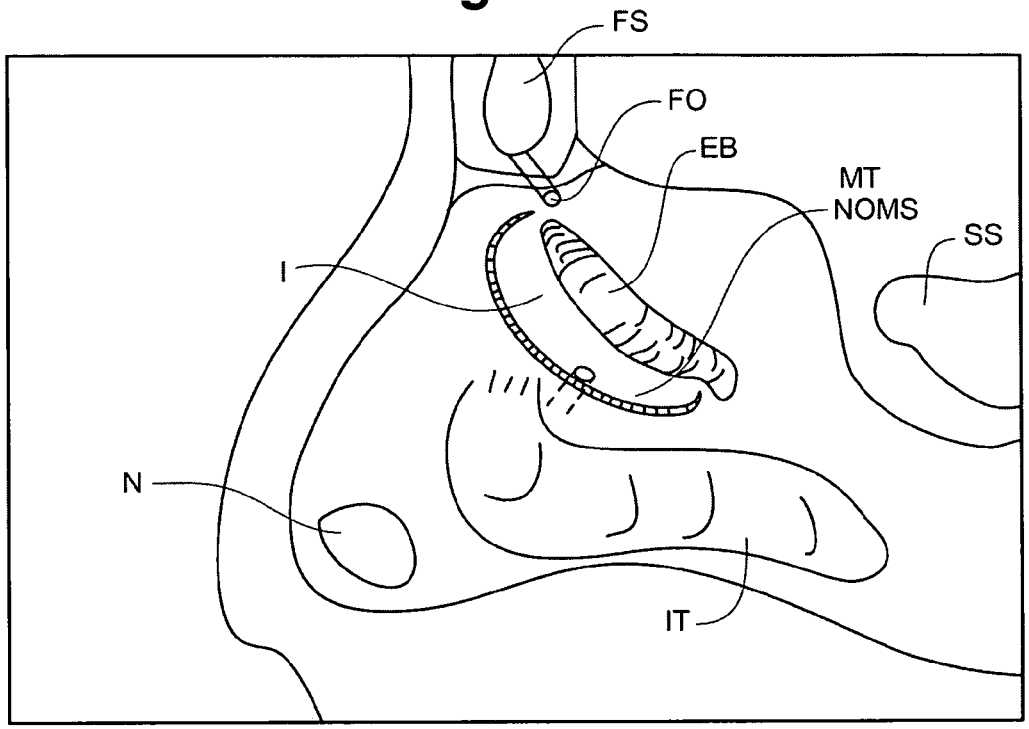
Figure 2A:
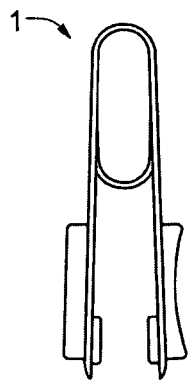
FIGS. 2A-2B illustrate one embodiment according to the present invention of an anterior/superior middle turbinate retractor in compressed and expanded forms, respectively.
Figure 2B:
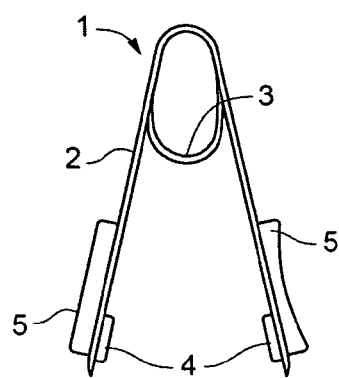

As depicted in FIG. 1A and FIG. 1B, the middle turbinate (MT) obstructs the surgeon from clearly viewing the uncinate process (UP) and the ethmoid bulla (EB). In the non-invasive procedures described below, it may be advantageous to first temporarily retract the middle turbinate from the procedural area and then restore it once the procedure is complete. To this end, I have developed turbinate retractors that assist the surgeon in visualizing the relevant anatomy around the obstructed sinus cavities. One embodiment of turbinate retractors in accordance with the present invention is displayed in FIGS. 2A-2B. FIGS. 2A and 2B depict an anterior/superior middle turbinate retractor (1) in compressed and expanded states, respectively. The anterior/superior middle turbinate retractor (1) is compressed (FIG. 2A) for introduction into the narrow space between the middle turbinate and lateral nasal wall in which it is allowed to passively expand (FIG. 2B) for gentle retraction. The retractor consists of a thin rigid metal or plastic frame (2) approximating a V-shape. An intervening pliable metal or plastic spring (3) enables compression and expansion upon squeezing and releasing the forceps receptacles (4). Pads (5) are placed at the contact surfaces of the lateral nasal wall and middle turbinate. These consist of a slightly compressible substance (e.g., foam rubber) surfaced with a smooth thin nonadherent, nonabrasive film to avoid trauma to the nasal lining. Preferably, the device should compress to a width of less than 3 mm and should be able to expand to a width that need not markedly exceed 10 mm.

Figure 3A:
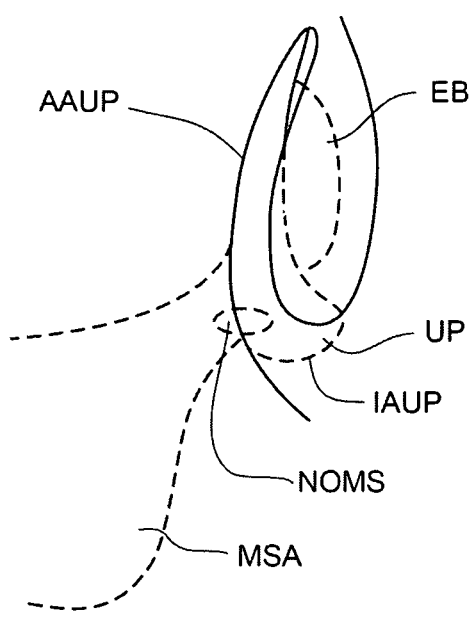
FIGS. 3A-D illustrate one embodiment of the present invention showing middle turbinate retraction by expansion of an anterior/superior middle turbinate retractor.
Figure 3B:
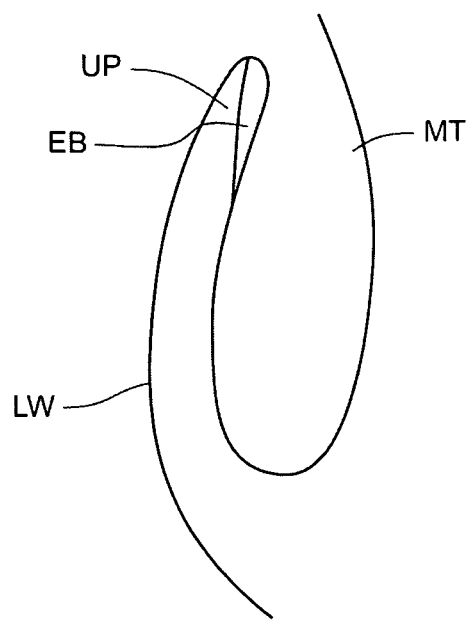
Figure 3C:
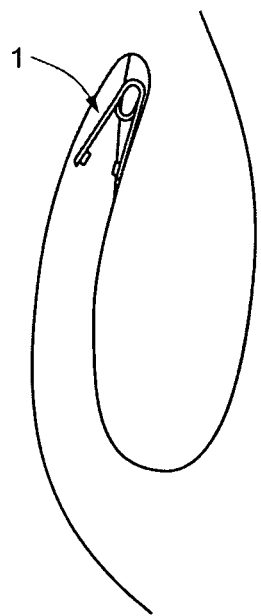
Figure 3D:
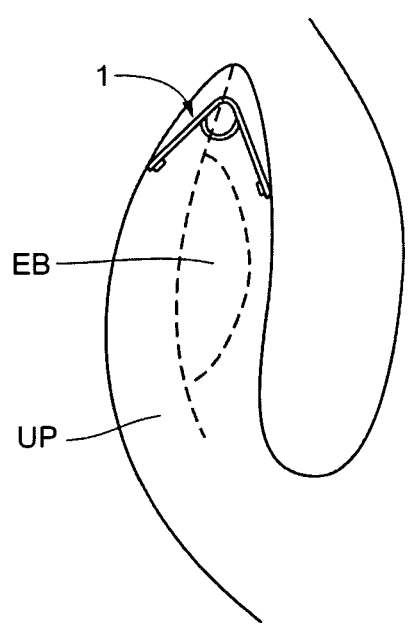

FIGS. 3A-3D show application of the use of the anterior/superior middle turbinate retractor (1) of the present invention. In the intact and unoperated nose, the middle turbinate (MT) obstructs the view of the structures practitioners wish to manipulate from the routine endoscopic vantage point (FIGS. 3A and 3B). Placement of the anterior/superior retractor (1) into the axilla of the middle meatus (FIG. 3C) and its subsequent expansion (FIG. 3D) reveals those structures and maintains the view throughout the procedure without repeated manipulation of the middle turbinate (MT), which is often otherwise required.

Figure 4A:
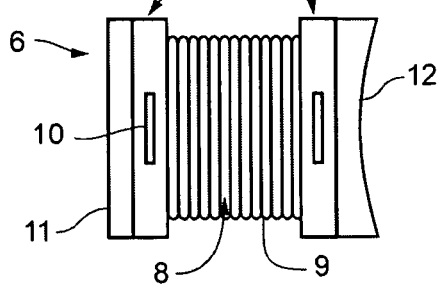
FIGS. 4A-4B illustrate one embodiment according to the present invention of a posterior/inferior middle turbinate retractor in compressed and expanded forms, respectively
Figure 4B:
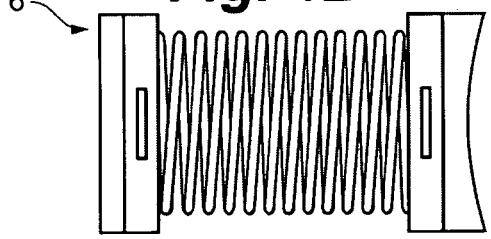

The middle turbinate (MT) may also be retracted medially by another device of the present invention depicted in FIGS. 4A-4B. FIGS. 4A and 4B depict an embodiment of a posterior/inferior middle turbinate retractor (6) in compressed and expanded form, respectively. The posterior/inferior middle turbinate retractor (6) is wedged between the lateral wall of the nose and the middle turbinate just posterior and inferior to the posterior root of the uncinate process (refer to FIGS. 7A-7F). The posterior/inferior middle turbinate retractor (6) functions via a passive spring compression-expansion mechanism, analogous to that described above for the anterior-superior retractor shown in FIGS. 2A-2B. The posterior-inferior middle turbinate retractor consists of two rigid metal or plastic platforms (7) with an intervening metal or plastic spring (8). It may be preferable to have the spring encased in a thin plastic sleeve (9) to aid in spring alignment and to avoid tangling. The device is manipulated via the forceps receptacles (10), similar to the anterior/superior middle turbinate retractor. Similar padding also is present here (11) with a curvature (12) incorporated to accommodate the anatomy near the middle turbinate (MT).

Figure 5A:
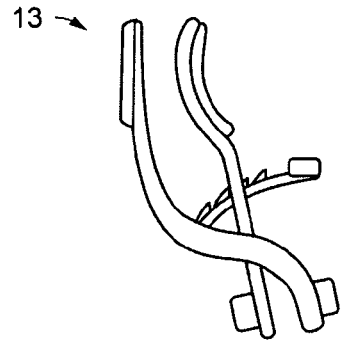
FIGS. 5A-5B illustrate an alternative embodiment according to the present invention of a posterior/inferior middle turbinate retractor in compressed and expanded forms, respectively
Figure 5B:
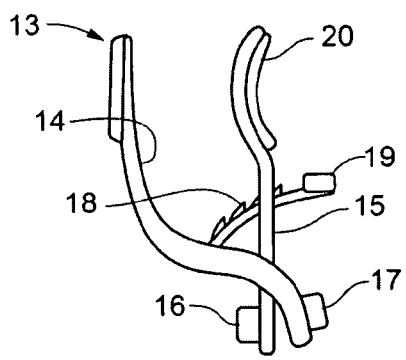

Another embodiment of the posterior/inferior middle turbinate retractor of the present invention is depicted in FIGS. 5A and 5B. FIGS. 5A and 5B depict an embodiment of a posterior/inferior middle turbinate retractor (13) in compressed and expanded form, respectively. In this embodiment, posterior/inferior middle turbinate retractor (13) expands by a ratcheting mechanism and passively contracts upon release. The device (13) consists of two rigid metal or plastic arms. The first plastic arm (14) comes in contact with the lateral wall of the nose and the second plastic arm (15) abuts the middle turbinate. The arms are actively expanded by squeezing the expansion receptacles (16 and 17) together. The arms are held in expansion by the ratchet arm (18) at the desired width and released by squeezing the release receptacle (19) toward the expansion receptacle (17). Pads (20) also may be present on this device. Dimensions of the arms (14) should be similar to those described previously for the anterior/superior middle turbinate retractor.

Figure 6A:
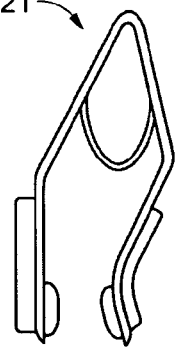
FIGS. 6A-6B illustrate an alternative embodiment according to the present invention of a posterior/inferior middle turbinate retractor in compressed and expanded forms, respectively
Figure 6B:
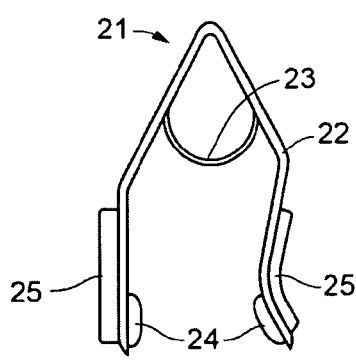

Another embodiment of the posterior/inferior middle turbinate retractor of the present invention is depicted in FIGS. 6A and 6B. FIGS. 6A and 6B depict an embodiment of a posterior/inferior middle turbinate retractor (21) in compressed and expanded form, respectively. The retractor consists of a thin rigid metal or plastic frame (22). An intervening pliable metal or plastic spring (23) enables compression and expansion upon squeezing and releasing the forceps receptacles (24). Pads (25) are placed at the contact surfaces of the lateral nasal wall and middle turbinate. These consist of a slightly compressible substance (e.g., foam rubber) surfaced with a smooth thin nonadherent, nonabrasive film so as to avoid trauma to the nasal lining. Preferably, the device should compress to a width of less than 3 mm and should be able to expand to a width that need not markedly exceed 10 mm.

Figure 7A:
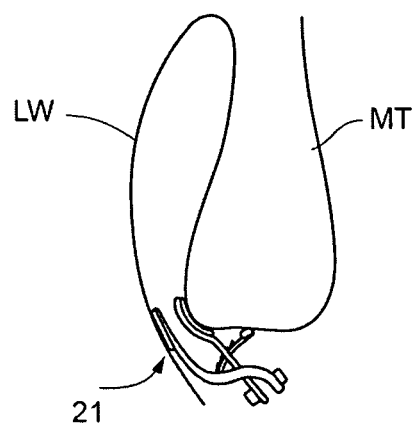
FIGS. 7A-7B illustrate one embodiment of the present invention showing middle turbinate retraction by expansion of a posterior/inferior turbinate retractor.
Figure 7B:
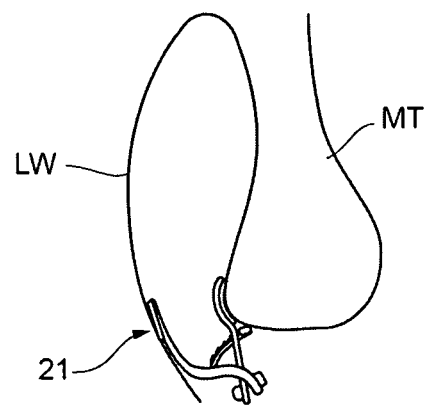
Figure 7C:
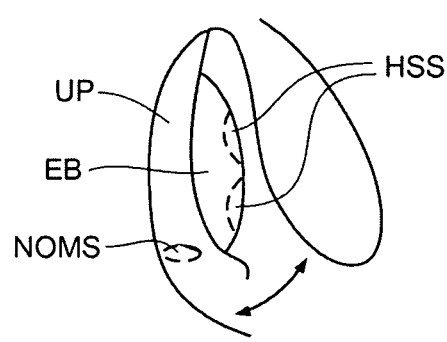
FIG. 7C illustrates a sinus in which the middle turbinate is retracted using a posterior/inferior turbinate retractor of the present invention.
Figure 7D:
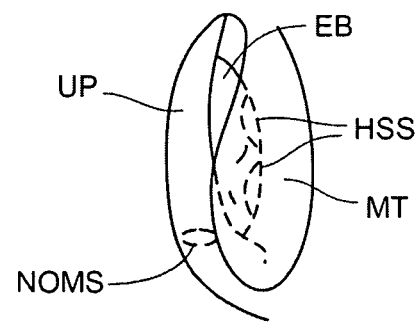
FIG. 7D illustrates a sinus in which the middle turbinate is not retracted.

FIGS. 7A-7C show application of the use of a posterior/inferior turbinate retractors of the present invention. FIGS. 7A-7C depict a cross-section of the lateral wall (LW) and middle turbinate (MT) in the coronal plane of the bulla. Notably, the posterior/inferior retractor (FIGS. 4-6) serves the same purpose as the anterior/superior middle turbinate retractor, but is placed in a separate location and may have the advantage of remaining posterior to all surgical maneuvers in subsequent steps. As depicted in FIG. 7A, the posterior/inferior turbinate retractor (21) is placed between the lateral wall (LW) and the middle turbinate (MT). Placement of the posterior/inferior turbinate retractor (21) is inferior to the ethmoid bulla (not shown in FIG. 7A). It is then expanded (FIG. 7B) to retract the middle turbinate. FIG. 7C depicts an endoscopic view with the posterior/inferior turbinate retractor in place. The result of the retraction is to improve the exposure of vital sinus structures including the uncinate process (UP), ethmoid bulla (EB), hiatus semilunaris superior (HSS) and natural ostium of the maxillary sinus (NOMS). Comparably, without the aid of a posterior/inferior turbinate retractor (FIG. 7D), these anatomical structures are substantially unexposed.

Because both middle turbinate retractors of the present invention yield improved exposure of the sinus surgical field, they may be useful in more traditional endoscopic surgeries as well as methods described in the present invention. It should also be noted that although these retractors are deemed convenient for the methods of the present invention, as described below they would not considered necessary for their execution.

Access To The Maxillary Sinus

A substantial application for the minimally invasive sinus access of the present invention is to provide solutions to mild-to-moderate sinusitis in the maxillary and ethmoid sinuses. In preferred embodiments of the present invention, the procedures can be performed in the surgeon's office, under minimal anesthesia, and after moderate (rather than extensive) medical options are exhausted. Such a procedure must (1) be easy to learn by practitioners of current routine sinus surgical art; (2) produce reliable prolonged improvement after healing rapidly with little-to-no pain or bleeding; and (3) provide a quick return to normal activity. As such, the procedure should resemble, as much as possible, the familiar approaches to the sinuses in question, and intranasal trauma must be minimized, especially in the sinus outflow tracts and at the ostium margin, where mucus first exits the sinus.

In a preferred embodiment of the present invention, the procedure of the present invention approaches the maxillary sinus natural ostium transnasally, from anterior to posterior, avoids traumatizing the outflow tract of any known sinus, and allows direct visual verification of a true natural ostium placement of the dilator before dilation is performed. That is accomplished by an anterior transuncinate "keyhole" approach to the natural ostium of the maxillary sinus described in detail below. Safe, reliable perforation of the uncinate and dilation of the natural ostium and ethmoid infundibulum are obtained using new devices of this invention as described below. This approach and these devices enable the performance of a reliable minimally invasive correction of maxillary sinusitis under minimal anesthesia.

Prior to addressing the uncinate process (UP) and ethmoid infundibulum (EI), it may be convenient to retract the middle turbinate as described above. However, middle turbinate retraction is not necessary for performing the procedures described below.

Figure 8A:
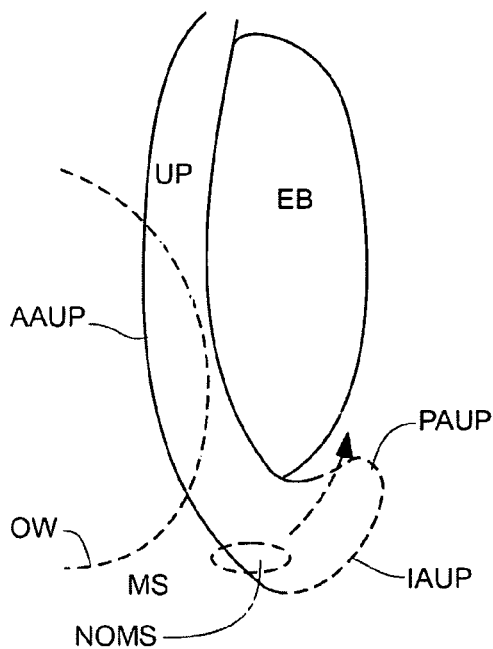
FIG. 8A illustrates the anatomical structures observed during a typical anteroinfermedial-to-posterosuperolateral view during nasal endoscopy (i.e., endoscopic view).
Figure 8B:
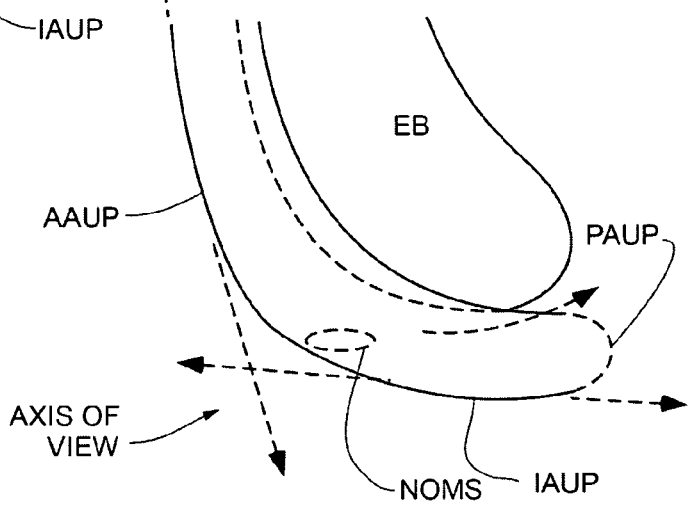
FIG. 8B illustrates a medial-to-lateral sagittal view of the relevant structures of the middle meatus.
Figure 8C:
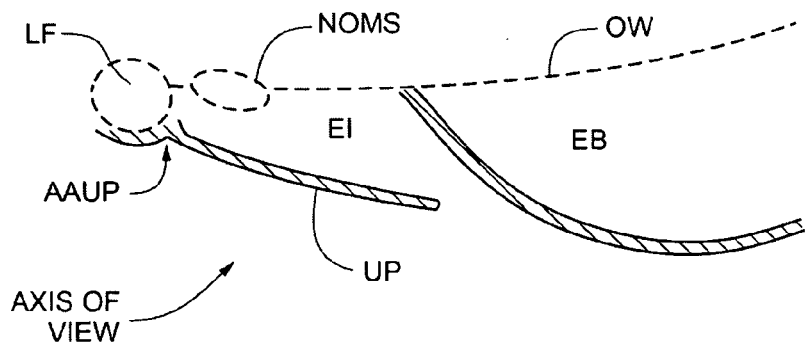
FIG. 8C illustrates a transverse view from superior-to-inferior of the relevant structures of the middle meatus.

Relevant anatomy around the maxillary sinus is illustrated in FIGS. 8A-8C. FIG. 8A shows the typical anteroinferomedial-to-posterosuperolateral view obtained during nasal endoscopy; FIG. 8B represents a medial-to-lateral sagittal view of the relevant structures of the middle meatus; FIG. 8C represents the same structures in transverse view from superior-to-inferior. It is noted that each procedure described below with respect to the maxillary sinus shows these three separate views for clarity. The patient's right side is chosen for consistency and convenience. The figures show that the uncinate process (UP) is anterior and inferior to the ethmoid bulla (EB). The anterior attachment of the uncinate process (AAUP) and the posterior attachment of the uncinate process (PAUP) are depicted. The ethmoid infundibulum (EI) lies in the narrow space between the uncinate process (UP) and the lateral wall of the nose, just anterior to the ethmoid bulla (EB) and can be seen most clearly in FIG. 8C. The maxillary sinus (MS) connects to the natural ostium of the maxillary sinus (NOMS) which is located lateral to the uncinate process. Natural drainage of mucous from the maxillary sinus, indicated by the arrow in FIG. 8A, occurs through the natural ostium of the maxillary sinus (NOMS) into the ethmoid infundibulum (EI). The natural ostium of the maxillary sinus (NOMS) cannot be observed directly because it is blocked by the uncinate process (UP). The "keyhole" approach of the present invention overcomes this problem and allows the surgeon a direct view of the natural ostium of the maxillary sinus (NOMS) and ethmoid infundibulum (EI).

In accordance with one aspect of the present invention, access to the ethmoid infundibulum (EI) is gained at the anterior-inferior extent of the uncinate using a backbiting hole punch of the present invention (FIG. 9A) to create a transuncinate "keyhole". The intended site of the keyhole is indicated with an asterisk in FIGS. 10A-10C, which show the anteroinferomedial-to-posterosuperolateral view, medial-to-lateral sagittal view, and the transverse view from superior-to-inferior, respectively. The backbiting hole punch (26) depicted in FIG. 9A enables atraumatic access to the natural ostium. It is configured much like the backbiting forceps used by most surgeons in the prior routine sinus art. Unlike that instrument, however, it perforates the uncinate near its anterior attachment only, rather than removing it en route from the posterior margin. Perforating the uncinate process (UP) anteriorly rather than dividing it transversely into superior and inferior "flail segments" preserves the overall integrity of the uncinate mucosa and bony framework. This structural support is key to preserving surgical modifications that will be described below in the method of the present invention and avoiding complications of healing.

Figure 9A:
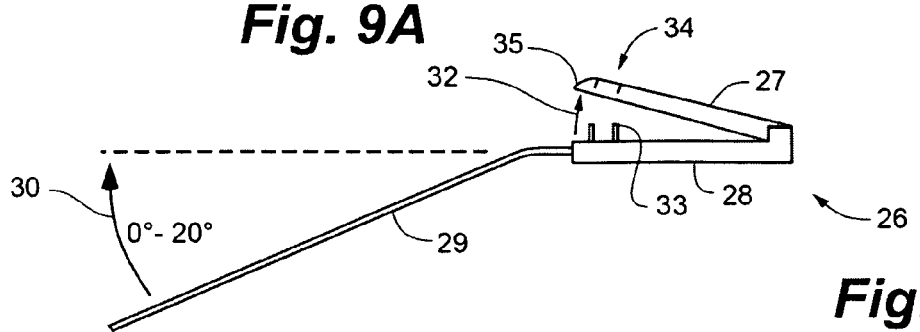
FIG. 9A illustrates a backbiting hole punch according to one embodiment of the present invention.
Figure 9B:
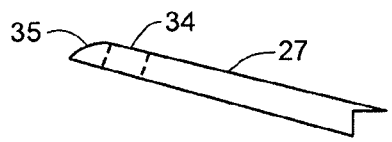
FIGS. 9B-9D illustrate a side view, a top view and an end-on view, respectively, of the mobile tapered flange of the backbiting hole punch of the present invention.
Figure 9C:
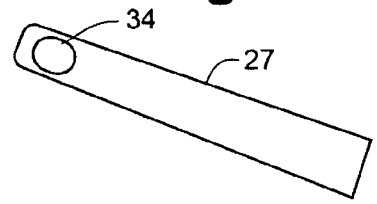
Figure 9D:
Figure 9E:
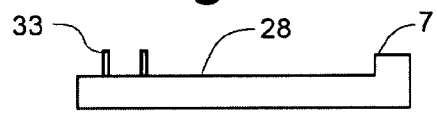
FIGS. 9E-9G illustrate a side view, a top view and an end-on view, respectively, of the stationary platform of the backbiting hole punch of the present invention.
Figure 9F:
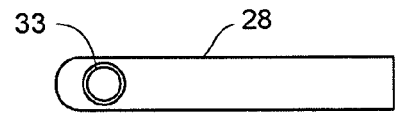
Figure 9G:
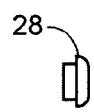
Figure 9H:
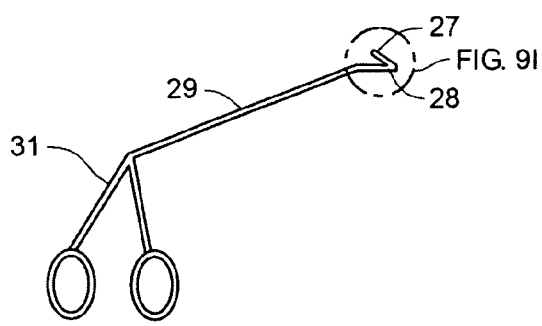
FIG. 9H illustrates a view of the handles of the backbiting hole punch of the present invention.
Figure 10A:
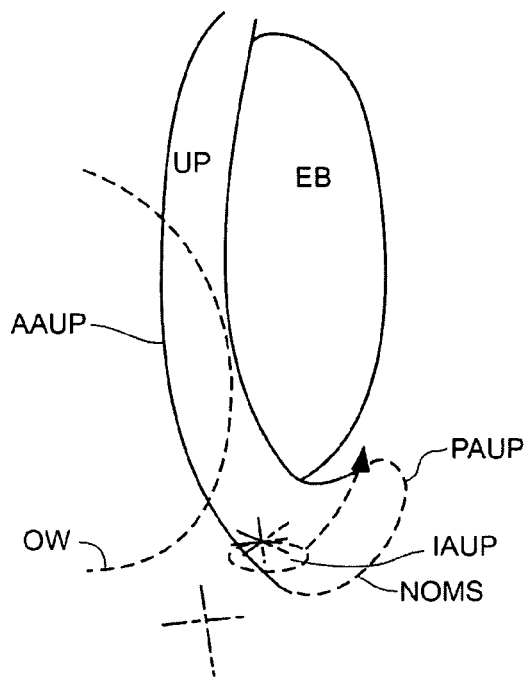
FIGS. 10A-10C illustrates three views (endoscopic, sagittal, transverse) of the intended site of the uncinate process "keyhole" formed using instruments and methods of the present invention.
Figure 10B:
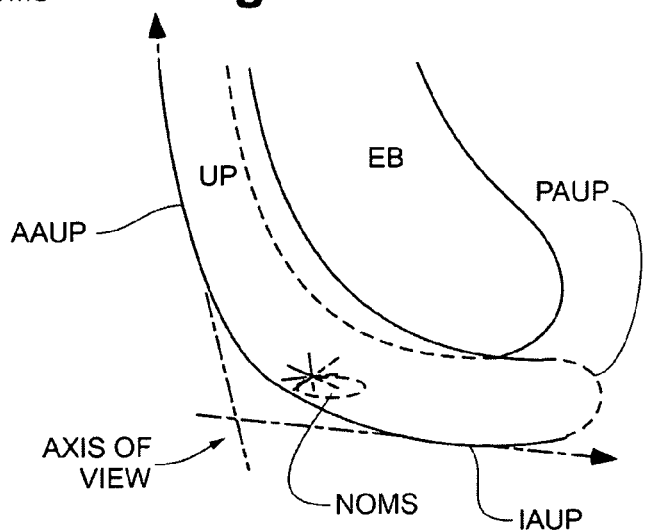
Figure 10C:
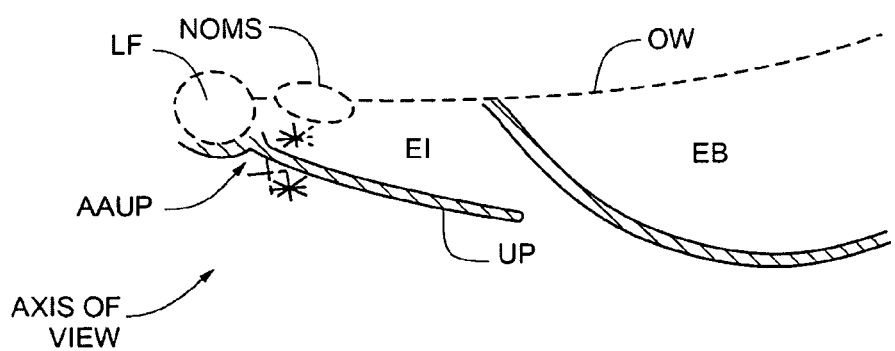

The backbiting hole punch (26) depicted in FIG. 9A consists of a mobile tapered flange (27) and a stationary platform (28) mounted on a shaft (29) that connects to handles (31) (not shown in FIG. 9A) that are manipulated by the practitioner. FIGS. 9B-9D show a side view, a top view and an end-on view of mobile tapered flange (27), respectively. Likewise, FIGS. 9E, 9F, and 9G show a show a side view, a top view and an end-on view the stationary platform (28), respectively. A blow-up of the handles (31) is depicted in FIG. 9H. As depicted in FIG. 9H, the handles (31) are located at the proximal end of the shaft (29). The handles (31) are manipulated by sticking two fingers is the holes and squeezing the holes together. The instrument can be made wholly of rigid material like metal or plastic but a portion of the shaft (29) may be composed of a semirigid material with some flex such as plastic, fiber compound, or rubber, in order to facilitate intranasal maneuvering. The shaft (29) may be straight or angled (30) up to approximately 20 degrees. If an angled shaft is used, the angle allows the mobile flange (27) and the stationary platform (28) to be delivered into the target area of the nose parallel to the orbital wall, uncinate process, and middle turbinate, facilitating access and limiting trauma. Spreading the handles (31) opens the gap angle (32) between the mobile flange (27) and the stationary platform (28) and squeezing them together closes it. Upon closure, a thin layer of material (in the method of the present invention, the thin bone and mucosa of the uncinate) is transfixed in between the flange (27) and platform (28) and creates a perforation ('keyhole') in the material as the blade (33) is pushed into the receptacle (34). In these diagrams, the blade is depicted on the platform (28) rather than on the mobile flange (27) so as to render the mobile flange (27) as thin as possible, a desirable characteristic for atraumatically introducing it into the narrow ethmoid infundibulum (EI), as described below in the method of the current invention. Nonetheless, the orientation can be reversed, if desired. The tip (35) of the mobile flange (27) may be tapered to facilitate the aforementioned insertion.

Figure 9I:
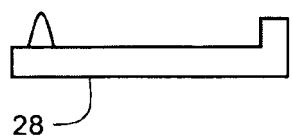
FIGS. 9I-9J illustrate an alternative stationary platform of the backbiting hole punch of the present invention.
Figure 9J:
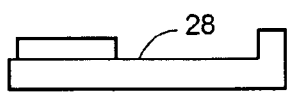

The length of the mobile flange (27) is preferably in the range of about 1.0 cm to about 2.0 cm. This length is chosen to maximize the possibility that the perforating tip will reach the anterior attachment of the uncinate when it is pulled to the anterior extent allowed by the uncinate atraumatically (see FIGS. 13A-13C and FIGS. 14A-14C) while at the same time maintaining maneuverability within the nose. A hole of approximately 3 mm is chosen as this size easily admits the guide-free dilator of this invention (see FIGS. 15A-15C, below) and a 2.7 mm endoscope (widely available), but other sizes are admissible, including a blade design that punctures without removing tissue (FIG. 9I) or one that removes a strip rather than a circle of tissue (FIG. 9J).

Figure 11A:
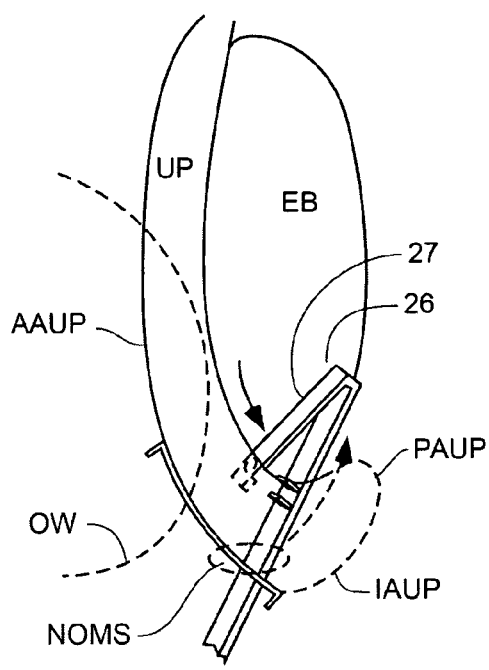
FIGS. 11A-11C illustrate three views (endoscopic, sagittal, transverse) of initial placement of the backbiting hole punch into the posterior opening of the ethmoid infundibulum and the levering of the uncinate, in accordance with one aspect of the present invention.
Figure 11B:
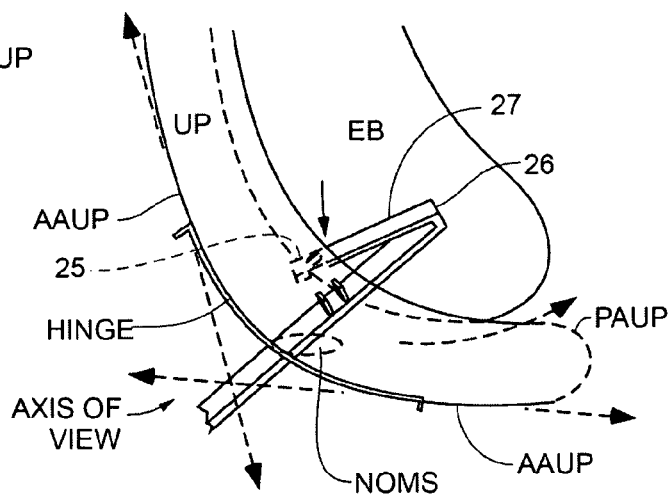
Figure 11C:
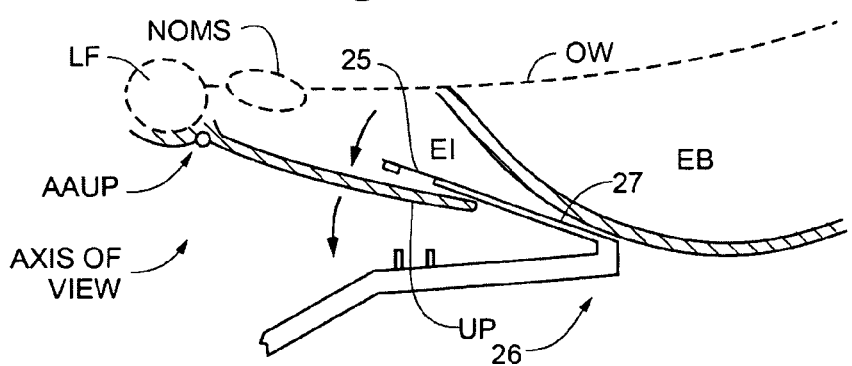
Figure 12A:
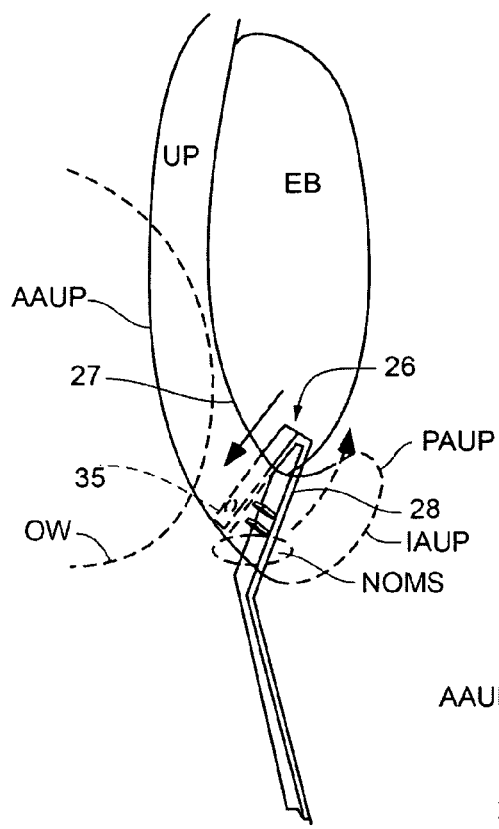
FIGS. 12A-12C illustrate three views (endoscopic, sagittal, transverse) of final placement of the backbiting hole punch into the posterior opening of the ethmoid infundibulum and the levering of the uncinate, in accordance with one aspect of the present invention.
Figure 12B:
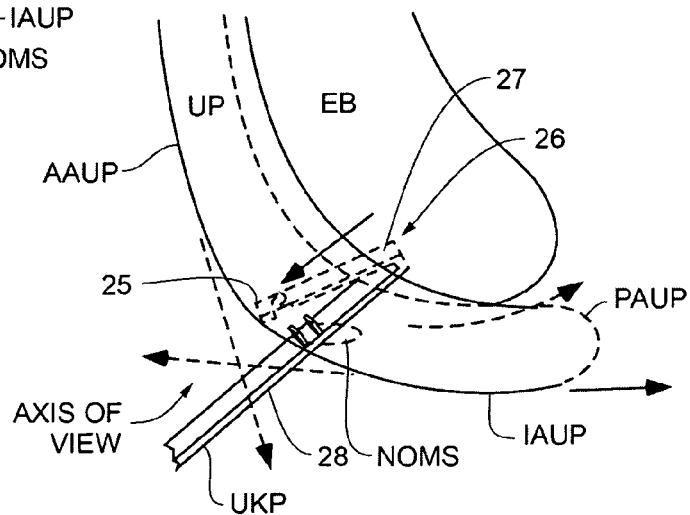
Figure 12C:
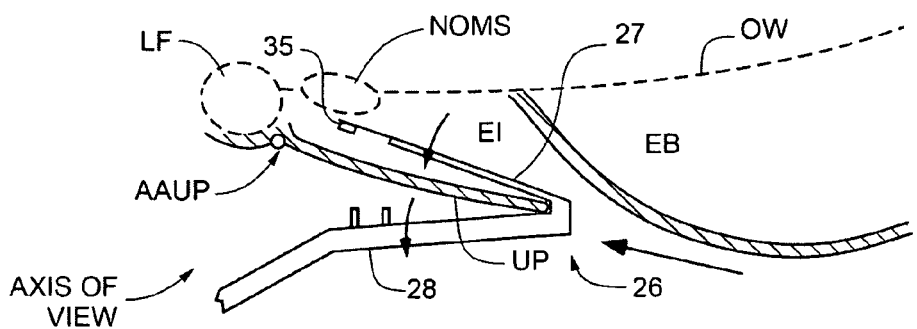
Figure 13A:
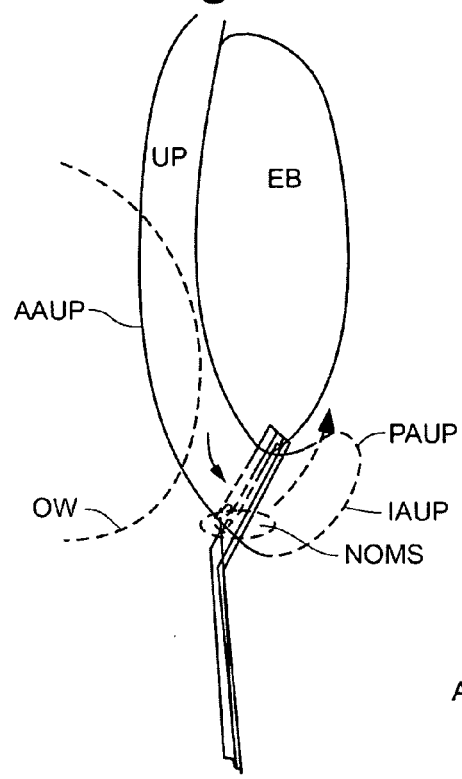
FIGS. 13A-13C illustrate three views (endoscopic, sagittal, transverse) of creating a keyhole in the uncinate process, in accordance with one aspect of the present invention.
Figure 13B:
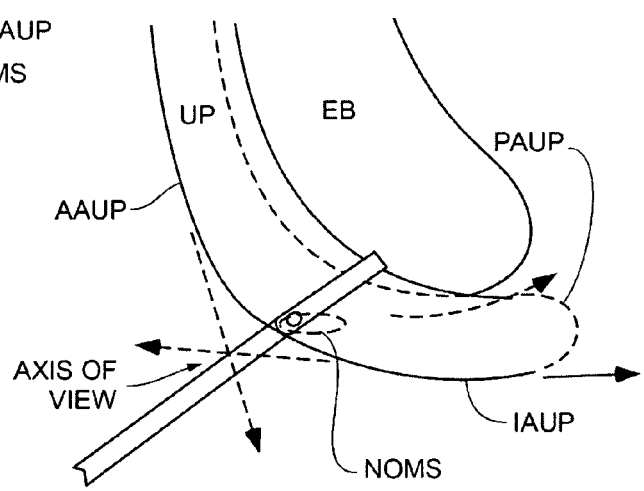
Figure 13C:
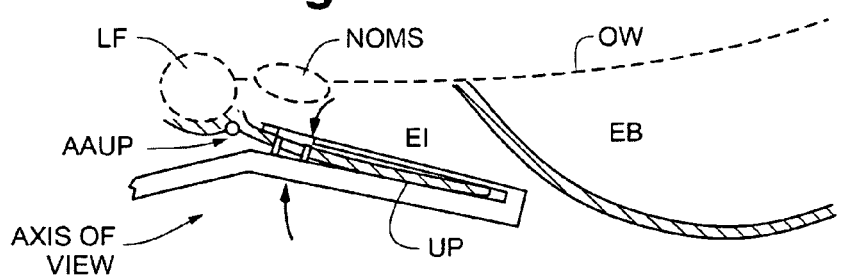
Figure 14A:
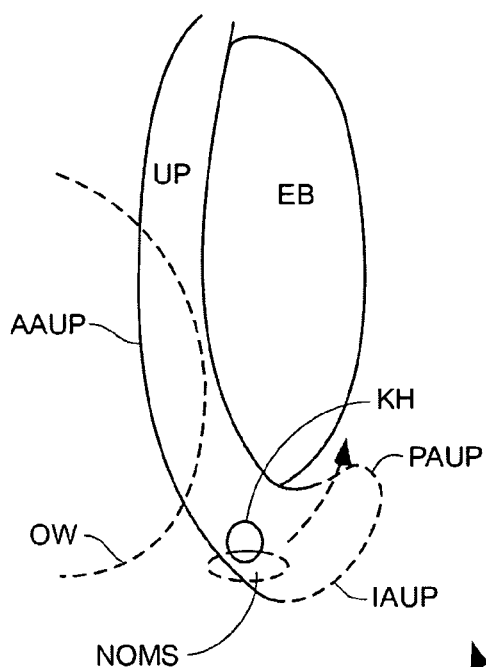
FIGS. 14A-14C illustrate three views (endoscopic, sagittal, transverse) of the keyhole created in the uncinate process, in accordance with one aspect of the present invention.
Figure 14B:
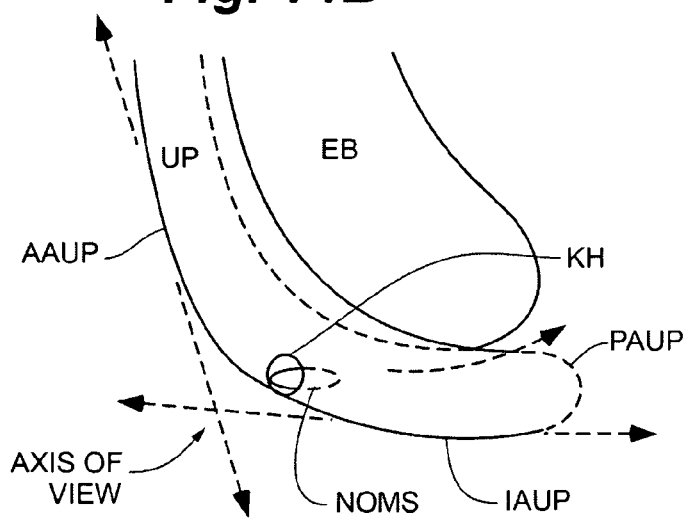
Figure 14C:
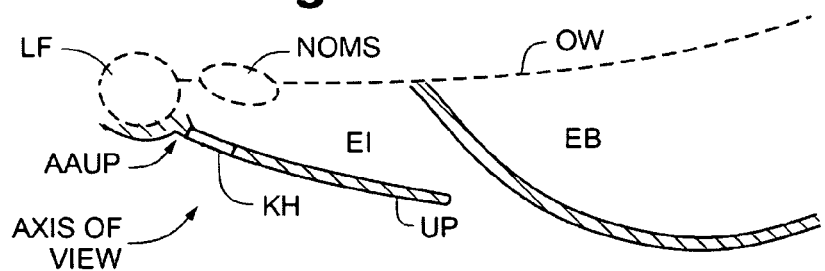

Referring again to FIG. 10B, the uncinate process (UP) has a shape similar to a boomerang with its arms directed anterosuperior and posterior, respectively. The entry site (indicated on FIGS. 10A-10C by an asterisk) of the hole punch mobile flange (27) is in the crotch of the boomerang and directed anteriorly toward the apex of the boomerang. As depicted in FIGS. 11A-11C, the mobile flange (27) of backbiting hole punch (26) is advanced into the posterior opening of the ethmoid infundibulum (EI) well superior to the pathway of mucus exit from the posterior ethmoid infundibulum (EI) and levered gently to assess the location of the anterior and inferior attachment of the uncinate process (UP). This maneuver facilitates the anterior advance of the mobile flange (27) within the ethmoid infundibulum (EI) by stretching the uncinate process (UP) a bit medially and helps define the anterior and inferior attachments of the uncinate process (UP) where the "swinging door" of the uncinate process "hinges" with respect to its skull attachments (FIGS. 11A-11C). The hinge zone (marked in FIGS. 11A-11C) defines the anterior and inferior extent of the ethmoid infundibulum (EI). The natural ostium of the maxillary sinus (NOMS) is reliably found a few millimeters posterior to the anterior-inferior apex of the ethmoid infundibulum (EI). As such the surgeon seeks to create the keyhole perforation as anterior and inferior as possible on the uncinate process (UP). He aims the tip (35) of the mobile flange (27) of hole punch (26) anterior and inferior toward the apex of the uncinate "boomerang," roughly the intersection of the axes of the anterior and inferior attachments of the uncinate (target sign in FIGS. 10A-10C). The tip (35) is advanced anteriorly and inferiorly by pulling the instrument toward the surgeon. It will naturally stop at the anterior inferior extent of the infundibulum (FIGS. 12A-12C) and the keyhole perforation is created there by squeezing the finger action together to close the mobile flange (27) to the stable platform (28) of the backbiting hole punch (26), transfixing the uncinate process (UP) and excising the intervening tissue (FIGS. 13A-13C). The tip works much like a paper hole-punch, scrupulously protecting the orbit while creating a perforation ('keyhole') in the uncinate process (UP) in the appropriate, strategically located position. Reliably, this maneuver will place the keyhole (KH) immediately medial to the natural ostium of the maxillary sinus (NOMS) or just anterosuperior to it (FIGS. 14A-14C). Such a position is ideal to allow anterior to posterior access to and visual verification of the natural ostium of the maxillary sinus (NOMS).

Figure 15A:
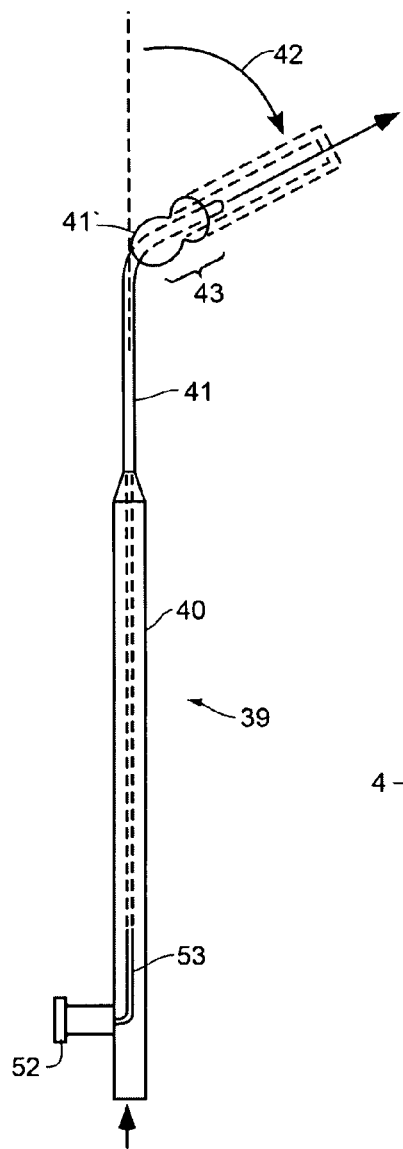
FIG. 15A illustrates one embodiment of a guide-free dilator of the present invention.
Figure 15B:
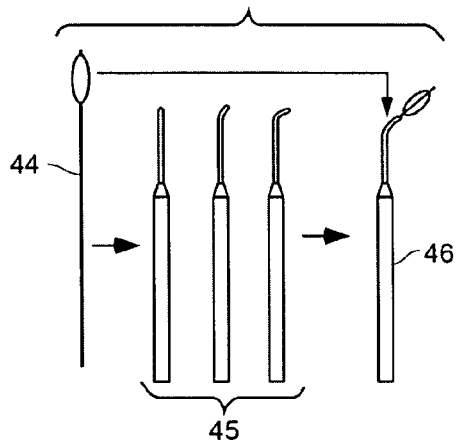
FIG. 15B illustrates an alternative embodiment of the guide-free dilator of the present invention.

After removal of the backbiter hole punch, a guide-free dilator of the present invention is used to restore the flow of mucous from the maxillary sinus to the nasal cavity. An embodiment of the guide-free dilator of is displayed in FIG. 15A. The guide-free dilator (39) consists of a rigid handle (40), preferably composed of metal or plastic, and a sufficiently rigid shaft (41), similarly composed, that incorporates a specific distal angulation (42). The range of allowable angles may be anywhere from 0 to 145 degrees from straight, but is preferably in the range of 30 to 60 degrees. The most preferred embodiment for general applicability in the sinuses is likely to be at or near 45 degrees. This fixed angulation (42) may be accomplished with a single integrated instrument as shown in FIG. 15A. Alternatively, multiple fixed angulations may be accomplished with a two-part embodiment (FIG. 15B). In this embodiment, a single semirigid catheter (44) can be clipped into a choice of several interchangeable handle-shaft carriers (45), each of a distinct fixed angle, if such versatility is desired. The combined instrument (46) would share the other characteristics of the integrated instrument and would be expected to function similarly. It will be appreciated that the sufficiently rigid shaft (41) of the guide free dilator (39) may have a minimal amount of malleability.

Figure 15C:
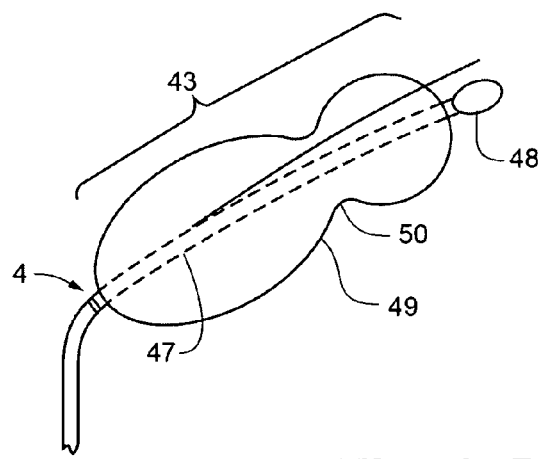
FIG. 15C illustrates a view of one embodiment of the dilator of the guide-free dilator of the present invention.
Figure 15D:
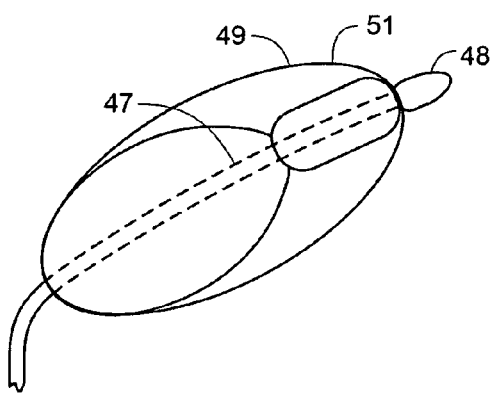
FIG. 15D illustrates a view of an alternative embodiment of the dilator of the guide-free dilator of the present invention.

The dilator segment (43) of guide-free dilator (39) is shown in FIG. 15C. The dilator segment (43) consists of a semirigid shaft (47), preferably composed of an external sheath of a plastic or fiber compound, ending in a spatulate or ellipsoid tip (48), and mounting a balloon (49). The semirigid shaft (47) is preferably made from a polymer. Preferable polymers include but are not limited to silicone rubber, polyurethane, polyethylene terephthalate, polyethylene, polypropylene, polyvinyl chloride, polymethyl methacrylate and polytetrafluoroethylene. In the embodiment shown in FIG. 15C, the balloon (49) can be configured as a modified "figure-8" (50). Alternatively, in the embodiment shown in FIG. 15D, the balloon has an ellipsoid configuration (51). The balloon is inflated and deflated by introduction or withdrawal of fluid through the inflation port (52) via the inflation conduit (53) (see FIG. 15A).

The guide-free dilator of the present invention has several unique properties that enable it to operate optimally within the sinuses. The handle (40) is widened to accommodate its fit within the surgeon's hand. The guide-free dilator is only semirigid distally but remains stiff for most of its length, facilitating control, allowing the surgeon to retract or reflect intranasal structures to a degree and to precisely direct the instrument using the dominant hand only. The device is intended to be used without a guide, and therefore, permits only minimal flexion, and only over a short segment of its total length. After the instrument angles distally at the bend (41') of substantially rigid shaft (41), it becomes semirigid in the dilator segment (43). This unique property is used in order to maintain enough rigidity to pass alongside walls at sufficiently shallow angles of address but to flex at sufficiently perpendicular angles. This property facilitates finding ostia and natural pathways through the paranasal sinuses and nose while avoiding the creation of false passages. These characteristics make it easier to navigate existing anatomy while avoiding damage. A spatulate tip (48) further reinforces these effects. As indicated above, the approximate angle of curvature is preferably given at 30-60 degrees, most preferably at about 45 degrees. This general range of angulation is appropriate for the intended approaches to the superior and inferior ethmoid infundibulum, natural maxillary ostium, hiatus semilunaris superior, ostia of the ethmoid bulla, and frontal sinus ostium.

In a preferred embodiment of the present invention, a balloon (49) functions as the actively dilating portion of the instrument. The length of the balloon is chosen to be approximately 1.0-2.0 cm, again appropriate for access to and dilation of the aforementioned structures. The range of 4-7 mm diameter for the balloon is chosen as appropriate to the anatomy of the structures intended for dilation. The modified "FIG. 8" configurations of the balloon depicted in FIG. 15C may help seat the balloon in the intended ostium, and if used, the dimensions presented do help the surgeon to work in these narrow spaces. A standard ellipsoid configuration of the balloon is also satisfactory. Although the above dimensions were not chosen expressly for other paranasal sinuses, they do allow navigation of the posterior ethmoid and sphenoid as well. Furthermore, its design enables dilation of the maxillary sinus and ethmoid infundibulum completely independent of guides or guide wires and only using the dominant hand, unique to the present invention, and unknown in the minimally invasive balloon dilation prior art.

Figure 16A:
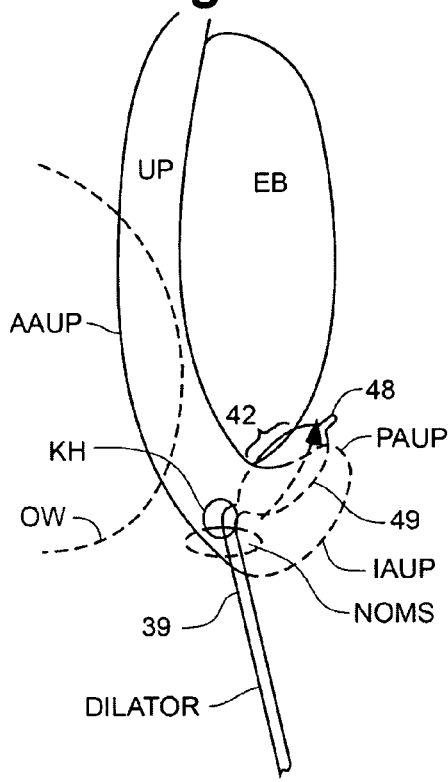
FIGS. 16A-16C illustrate three views (endoscopic, sagittal, transverse) of advancement of a guide-free dilator of the present invention through the transuncinate keyhole and dilation of the ethmoid infundibulum, in accordance with one aspect of the present invention.
Figure 16B:
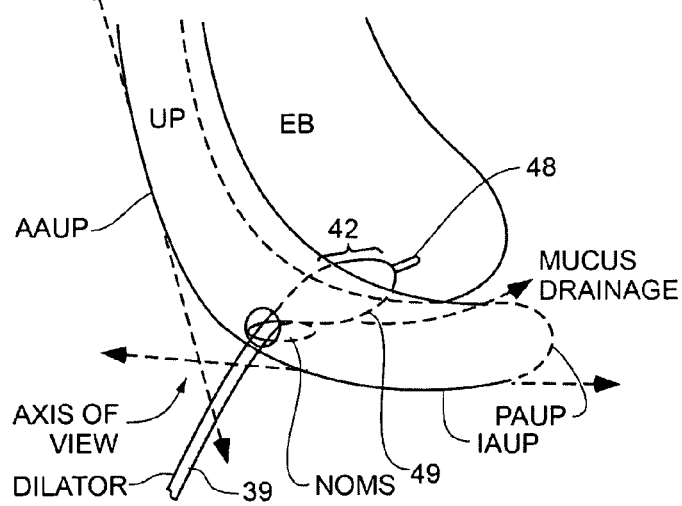
Figure 16C:
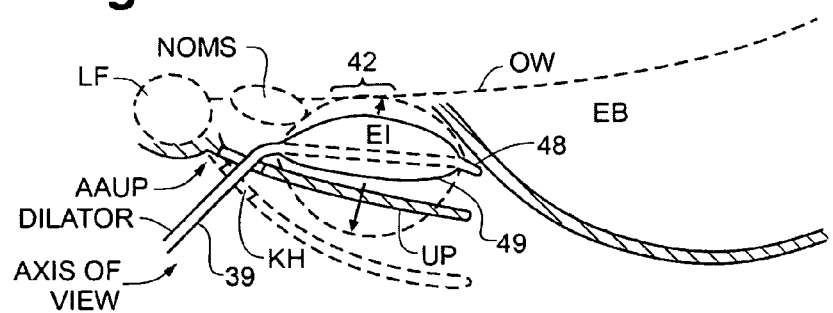
Figure 17A:
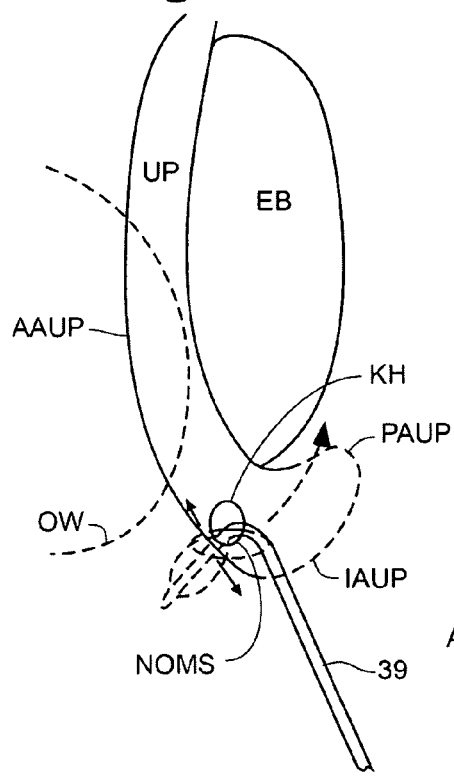
FIGS. 17A-17C illustrate three views (endoscopic, sagittal, transverse) of dilation of the natural ostium of the maxillary sinus using a guide-free dilator, in accordance with one aspect of the present invention.
Figure 17B:
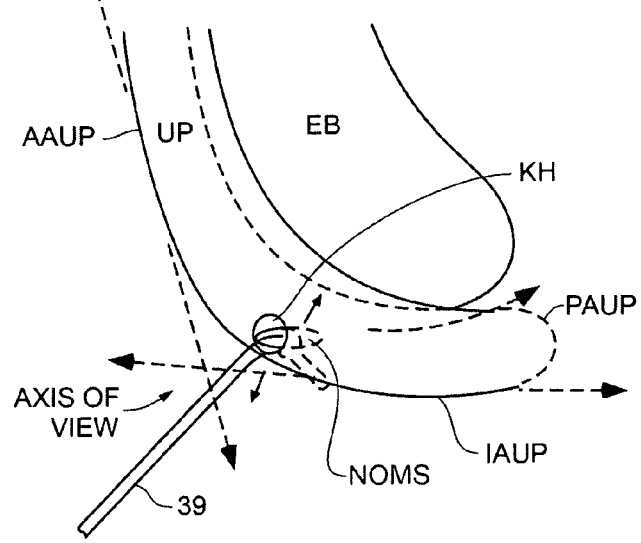
Figure 17C:
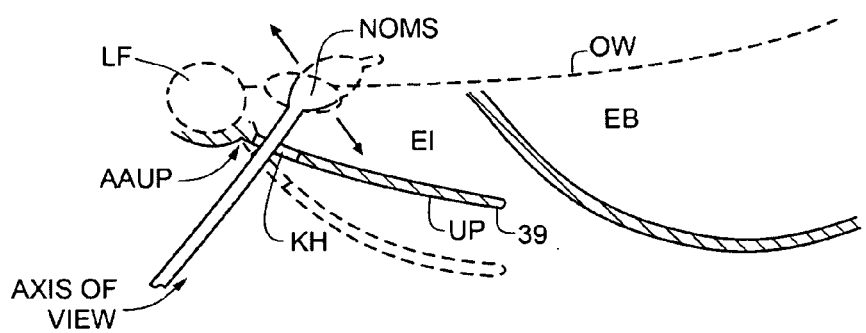

FIGS. 16A-16C depict use of the guide-free dilator (39) of the present invention. The guide-free dilator (39) can be advanced readily through the keyhole (KH) perforation in the uncinate process (UP). Under direct vision with an endoscope, the dilator tip (48) is advanced through the anterior uncinate keyhole (KH) into the mid-to-inferior ethmoid infundibulum (EI) and the balloon (49) is expanded, medializing the uncinate process. The 45 degree (approximate) angulation of dilator tip to shaft (FIG. 15A) is expressly chosen to allow easy and accurate advance of the tip into the ethmoid infundibulum (EI) via the keyhole (KH). This maneuver helps to open the final pathway of mucus drainage from the posterior infundibulum, best observed in FIG. 16B. The dilator is then withdrawn slightly, the tip is turned laterally and inferiorly and directed into the natural ostium of the maxillary sinus (NOMS) where dilation can again be accomplished (FIGS. 17A-17C). Again, the 45 degree angulation of the guide-free dilator (39) is ideal for this maneuver, with atraumatic, direct, and easy passage through the natural ostium of the maxillary sinus (NOMS) and into its antrum.

Figure 18A:
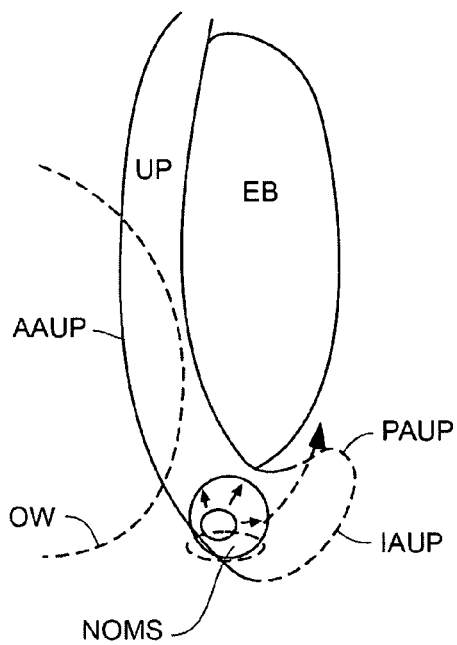
FIGS. 18A-18C illustrate three views (endoscopic, sagittal, transverse) of dilation of the transuncinate keyhole using a guide-free dilator, in accordance with one aspect of the present invention.
Figure 18B:
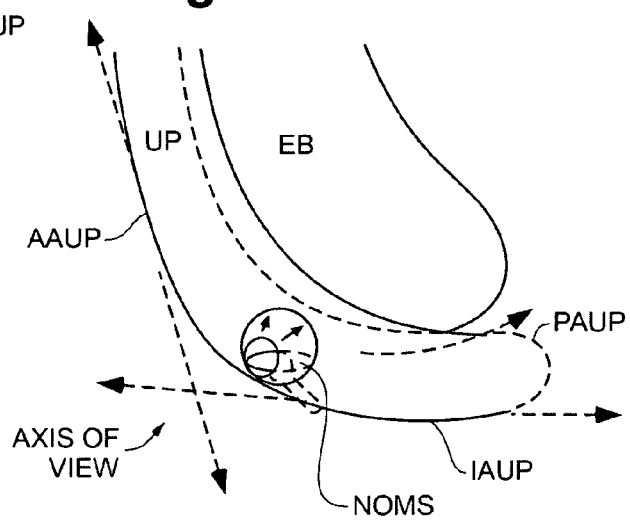
Figure 18C:
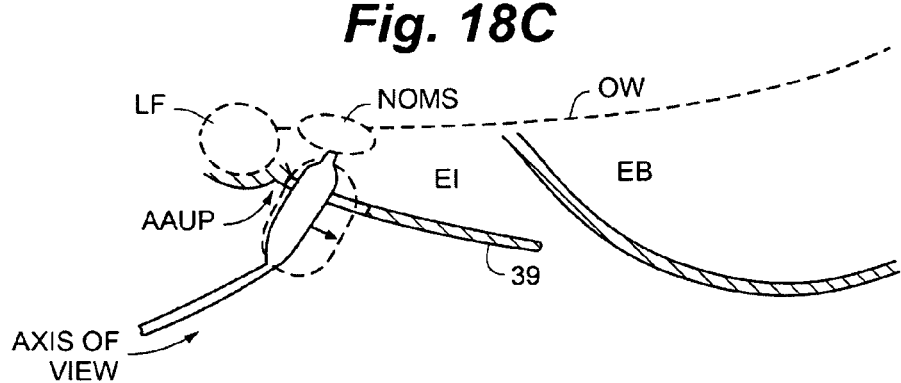

Of note, the dilator (39) of the present invention can also be used to dilate the keyhole (KH), if desired (FIGS. 18A-18C). The dilation is eccentric as maxillary bone is far more resistant than uncinate. The resulting dilation of the ethmoid infundibulum, natural ostium of the maxillary sinus, and, if desired, the keyhole are all visually verifiable with this approach.

Figure 19A:
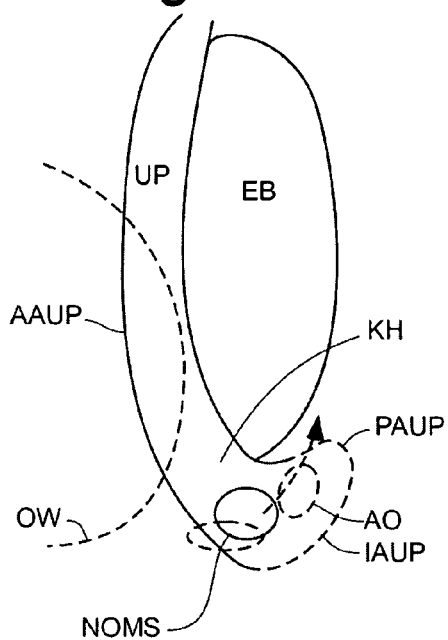
FIGS. 19A-19C illustrates attachment of the natural ostium of the maxillary sinus with an accessory ostium, according to one aspect of the present invention.
Figure 19B:
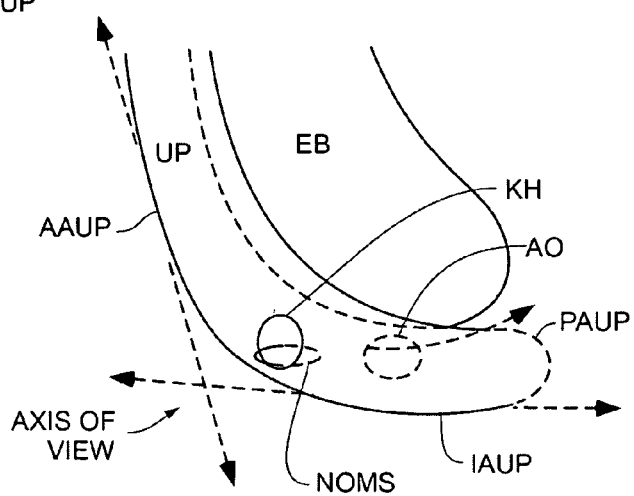
Figure 19C:
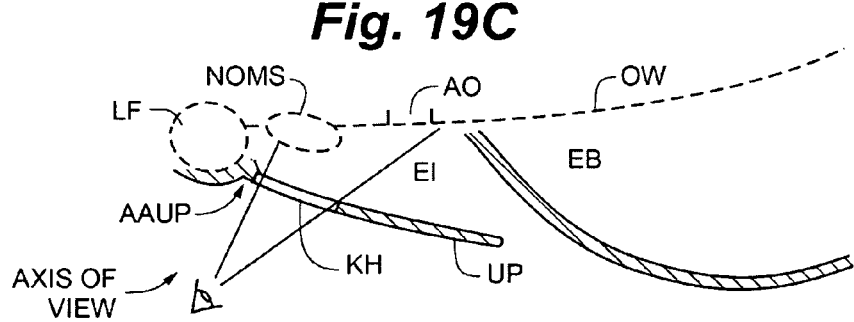

If an accessory ostium (AO) is identified (FIGS. 19A-19C), it may be broadly connected to the natural ostium of the maxillary sinus (NOMS) at this point, according to the surgeon's discretion. This option is deemed useful to exercise in many patients and is unique to the present invention in the balloon dilation art.

There are several key advantages of the present invention for treating obstructed maxillary sinuses:

1. Ease of use: For each maneuver of the present invention, the surgeon uses the nondominant hand purely for manipulation of the endoscope and the dominant hand purely for manipulation of a single surgical instrument. Both minimally invasive approaches of the prior art (see U.S. Pat. Nos. 7,500,971 and 7,559,925) use tubular guide catheters to direct the dilator appropriately, requiring more surgical field clutter and hand-switching maneuvers. These catheter-guide based systems are well-suited for (and, indeed, adapted from) percutaneous endovascular procedures like angioplasty, but foreign to sinus surgeons accustomed to instruments that enable fine movements of the fingers to translate directly and reliably into equally fine movements of the working tip of that instrument, and to do so using the dominant hand exclusively.
2. Direct visualization of the operative site: In the present invention, the surgeon can see the natural ostium before manipulating it and the approach is, conveniently, along the axis of the endoscopic view into the nose. In the intranasal procedure of the prior art, the natural ostium is never actually seen, but is presumptively identified by the verified presence of the guidewire in the maxillary sinus after blind passage (see U.S. Pat. Nos. 7,500,971 and 7,559,925).
3. Avoidance of trauma to key structures: The method of the present invention gains access to the natural ostium of the maxillary sinus without trauma to any areas that participate in mucus drainage from that sinus. In contrast, the guide-catheter system of the prior intranasal art requires a near-180 degree turn within the narrow confines of the middle meatus, a cumbersome approach that unavoidably traumatizes the ethmoid bulla and outflow tract of mucus exiting the maxillary sinus. Although we are proceeding posterior to anterior with the backbiter of the present invention, due to its design and surgeon control, it is essentially atraumatic in its passage. Further, one advances the backbiter from a point much higher in the posterior infundibulum than is used by the nose for mucus drainage, an area that is, on the contrary, necessarily traumatized by the guide, guidewire, and for that matter, withdrawal of the balloon post dilation in the method of prior intranasal art.
4. Identifying and appropriately treating accessory ostia: As noted above, accessory ostia are frequent anatomic findings. Mistaken dilation of these structures to the neglect of the natural ostium results in one of the commonest adverse complications of maxillary sinus surgery (mucus recirculation and worsening of maxillary sinusitis). The method of the present invention allows unequivocal identification of the natural ostium and easily enables identification of accessory ostia The intranasal procedure of the prior art may actually be more likely to dilate an accessory ostium, if present, than the natural ostium because the accessory ostia are frequently larger and invariably lie along the path that the guide wire follows in blind search for the natural ostium.
5. The procedure is easily combined with other sinus/nasal procedures: Unlike the canine fossa procedure (U.S. Pat. No. 7,520,876) of the prior art, the method of the present invention employs a purely intranasal approach that easily marries with the other intranasal procedures that usually are performed alongside the maxillary procedure. In addition to the simplicity of the approach, the method of the present invention uses the same core device for access to the other paranasal sinuses (as will be seen below), in marked distinction to the canine fossa approach and to the multiple guides employed by the intranasal approach of the prior art.

Access to the Anterior Ethmoid Sinuses

Figure 20:
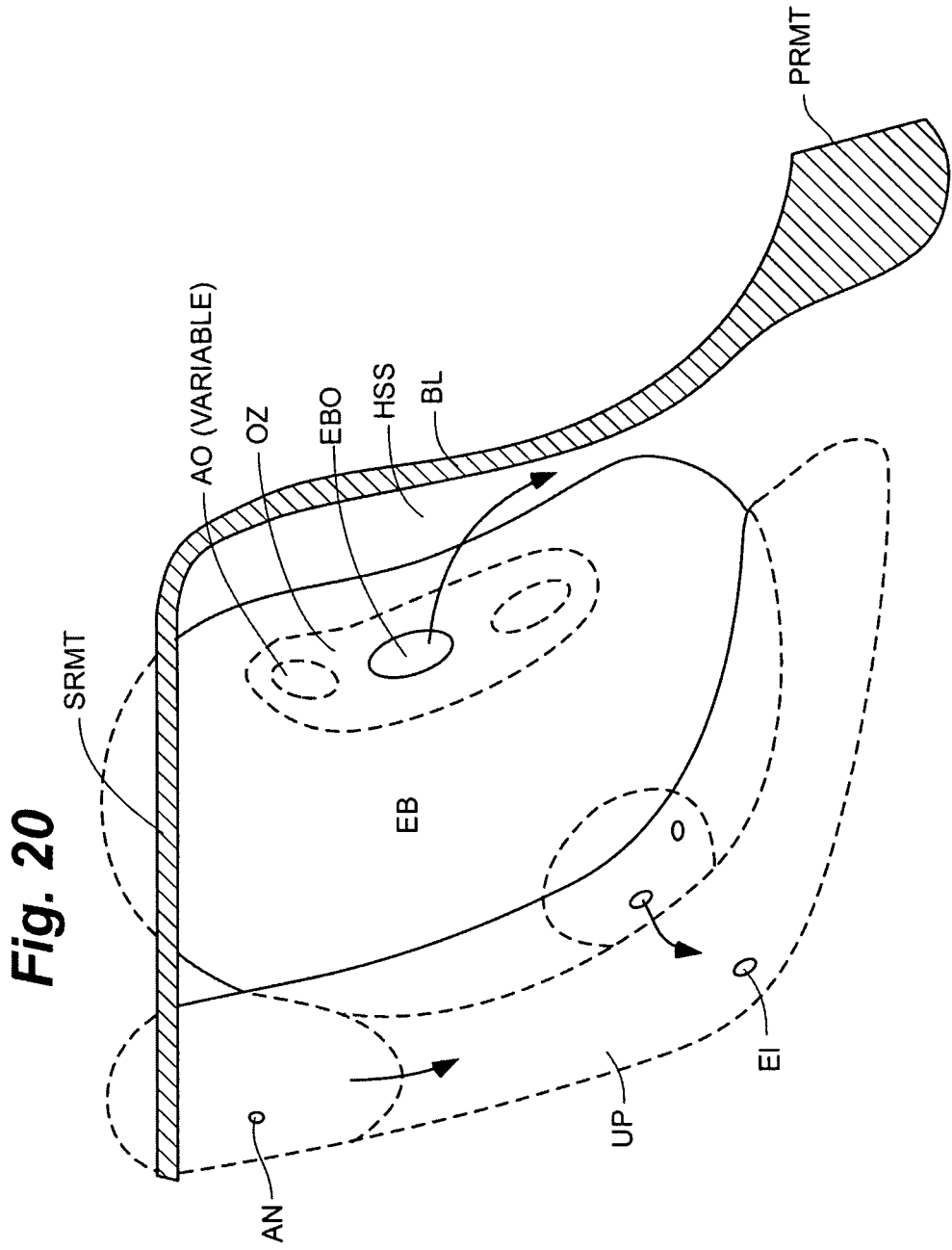
FIG. 20 illustrates a view from medial to lateral of the structures lateral to the middle turbinate with the turbinate removed.

The important anatomical features discussed in this section are displayed in FIGS. 20 and 21A-C. FIG. 20 is a view from medial to lateral of the structures lateral to the middle turbinate with the turbinate itself removed. Both the superior root of the middle turbinate (SRMT) and the posterior root of the middle turbinate (PMRT) can be seen in the diagram. The solid arrows indicate the path of mucous drainage. As will be discussed in more detail below, mucous from the anterior ethmoid sinus cells drains primarily through the ethmoid bulla ostium (EBO) into a narrow passageway between the ethmoid bulla (EB) and the basal lamella (BL), referred to as the hiatus semilunaris superior (HSS). Accessory ostia (AO) cam also be seen in the figure. The ethmoid bulla (EB) and accessory ostia (OA) are found in the posteromedial wall of the ethmoid bulla (EB). The ostial zone (OZ) in the ethmoid bulla wall is depicted in the diagram. FIG. 21A shows the typical anteroinferomedial-to-posterosuperolateral view obtained during nasal endoscopy. FIG. 21B represents a medial-to-lateral sagittal view of the relevant structures of the middle meatus. FIG. 21C represents the same structures in transverse view from superior-to-inferior. These three viewpoints will be used to depict the embodiments discussed below. In these figures, the solid arrows indicate the path of mucous drainage.

The anterior ethmoid is that group of pneumatized cells of the ethmoid that drain anterior to the basal lamella (BL), a roughly vertical thin bony wall that comprises the attachment of the middle turbinate to the lateral wall of the nose (FIG. 20). Those cells are often involved with inflammation synchronously with their maxillary sinus counterpart, frequently to the exclusion of the posterior ethmoid (PE)—or, that part of the ethmoid sinuses posterior to the basal lamella (FIG. 20)—hence, the distinction in clinical nomenclature within the ethmoid. A preferred embodiment of the present invention allows for systematically addressing the anterior ethmoid seamlessly with the maxillary sinus. In conventional minimally invasive sinus surgery (as per Messerklinger), the uncinate process (UP) is completely removed and the ethmoid bulla (EB) and adjacent anterior ethmoid air cells completely marsupialized (i.e., widely opened to broadly drain into the main vault of the nose.) With perhaps other minor alterations, that succeeds in opening all of the major cells and recesses of the anterior ethmoid. That procedure is largely successful in solving the inflammatory problems it sets out to treat. Those traumatic efforts can be painful for the patient, and in any case, moderate degrees of anesthesia, bleeding or nasal packing, prolonged stuffiness, and some missed work/activities are to be expected. The present invention achieves the same clinical results without those demerits.

As discussed above, there is greater variability and uncertainty as to the identity of the true drainage pathways for the anterior ethmoid. There also is variability among patients in the structure of the aptly-named ethmoid labyrinth. Many surgeons believe that the ethmoid infundibulum (EI) is the primary drainage site for the anterior ethmoid. Indeed, that is the usual drainage site for the agger nasi cell(s) (AN) (FIG. 20). The hypothesis in general, however, likely is unsound because the ethmoid bulla antrum rarely has a drainage communication with the ethmoid infundibulum (a septum of bone usually separates the two spaces), and when there is such a communication, it drains only a small isolated chamber of the ethmoid bulla (EB). In general, the main outlet from the ethmoid bulla (EB) and its dependent adjacent anterior ethmoid air cells is an ostium in the posteromedial wall of the ethmoid bulla, referred to as the ethmoid bulla ostium (EBO) (FIG. 20). Although the ethmoid bulla ostium (EBO) is not rigorously defined in the literature, it is invariably present, occasionally with a second or accessory ostium.

As depicted in FIGS. 21A-C, Mucus exits the ethmoid bulla ostium (EBO) into a narrow crescentic space between the posteromedial wall of the ethmoid bulla (EB) and the anterolateral wall of the basal lamella (BL) called the hiatus semilunaris superior (HSS). These anatomic observations are well-supported by published work dating back over one hundred years. The careful reader will note the analogy between the described drainage pathway in the anterior ethmoid and that previously elucidated for the maxillary sinus. In the anterior ethmoid, as in the maxillary, a well-defined ostium drains into a narrow secondary space. In the maxillary sinus, a successful method for augmenting flow will simultaneously open the natural ostium and ethmoid infundibulum (EI), as outlined earlier; in the anterior ethmoid sinuses, the method must open the ethmoid bulla ostium (EBO) and hiatus semilunaris superior (HSS).

In the current state of the art, marsupializing the anterior ethmoid is accomplished by removing most of the walls or septations of the anterior ethmoid with a microdebrider, cutting forceps, or some combination thereof. For those few surgeons who feel comfortable addressing the hiatus semilunaris superior (HSS) specifically, the same instrumentation is used to remove the medial wall of the ethmoid bulla (EB), leaving the opening in continuity with the hiatus. With current instrumentation, the hiatus area is opened by traumatizing it, thereby temporarily obstructing it with eschar (and possibly permanently with synechiae). There also is the typical bleeding, pain, healing time, need for anesthesia, and the use of stents or packing, all of which would be better to minimize or avoid. Most of these problems can be avoided by a minimally invasive approach that seeks to dilate the hiatus semilunaris superior (HSS) and ethmoid bulla ostium (EBO) without significant resection. To date, no such procedure exists in the prior art of sinus ostia dilation.

In a preferred embodiment of the present invention, the anterior ethmoid is addressed without necessitating prolonged healing by directly dilating the ethmoid bulla ostium (EBO) and the hiatus semilunaris superior (HSS). The ethmoid bulla ostium (EBO) is generally found on the superior posteromedial aspect of the ethmoid bulla (EB), and as such, is usually hidden from direct endoscopic view in the intact patient (FIG. 21A, endoscopic view). In accordance with the present invention, the hiatus can often be successfully entered from the medial approach, described below. If the medial approach is not easily successful, and in accordance with another aspect of the present invention, the surgeon can reliably perforate the anterior surface of the ethmoid bulla (EB) inferiorly and probe under direct vision superiorly to access the ethmoid bulla ostium (EBO) and through it, the hiatus semilunaris superior (HSS). As discussed below, such an anterior keyhole can also be used in conjunction with a medial approach to provide direct visual confirmation that the ethmoid bulla ostium (EBO) has been entered from without.

The medial approach is depicted in FIGS. 22-25. For clarity, these figures each show three different views of the relevant anatomy, which are identical to the views shown in FIGS. 21A-C. The procedure may begin, in identical fashion to that described above for the maxillary sinus, with middle turbinate retraction (FIGS. 3 and 7). Anesthesia is achieved locally and the middle turbinate is retracted out of the way. In this procedure, the retractor is of particular use in that here we require as much medial exposure of the ethmoid bulla as possible, and the middle turbinate otherwise obscures this area.

Figure 22A:
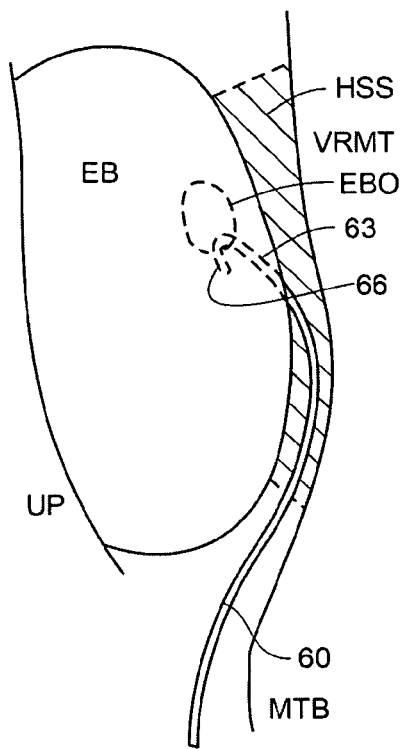
FIGS. 22A-22C illustrate three views (endoscopic, sagittal, traverse) of locating the ethmoid bulla ostium using an ethmoid probe of the present invention.
Figure 22B:
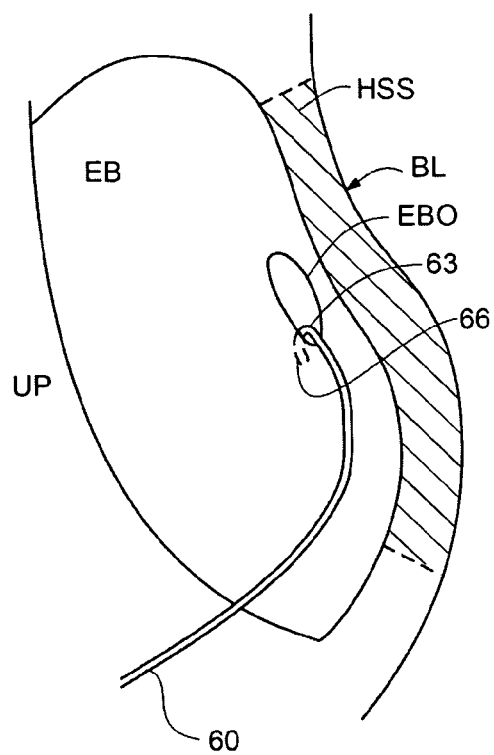
Figure 22C:
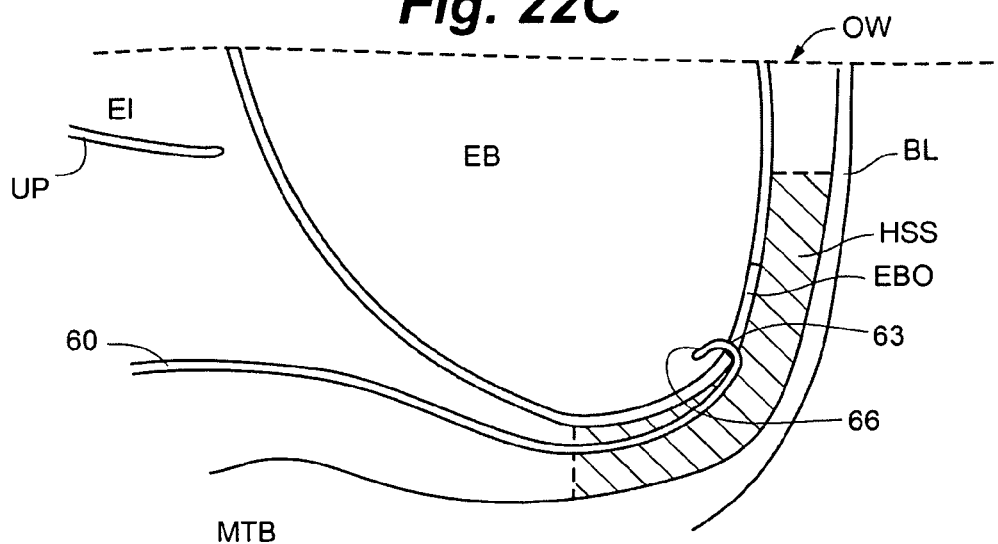
Figure 26A:
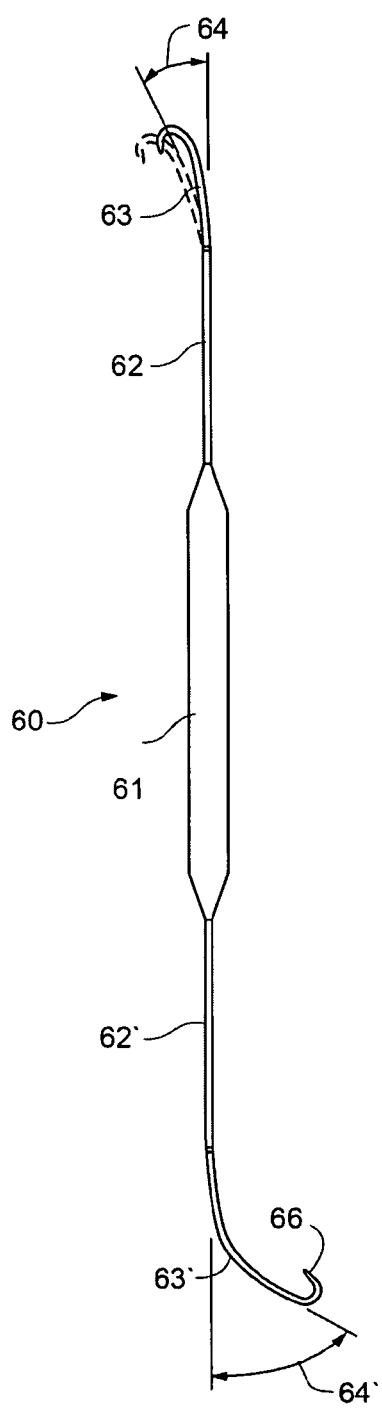
FIG. 26A illustrates an ethmoid probe of the present invention.
Figure 26B:
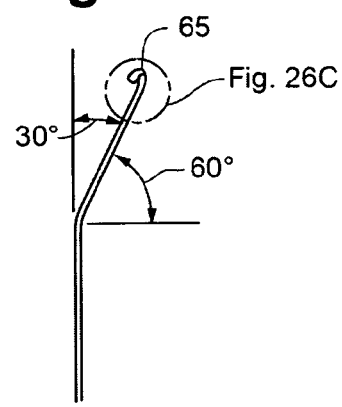
FIG. 26B illustrates the axis of approach of the ethmoid probe of the present invention.
Figure 26C:
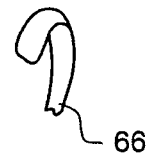
FIG. 26C illustrates a detail the curved tip of the ethmoid probe of the present invention.

Next, the hiatus semilunaris superior (HSS) is addressed from the medial approach. Turning to FIGS. 22A-C, curvilinear recess between the basal lamella (BL) of the middle turbinate and the posteromedial wall of the ethmoid bulla (EB) is entered with one or both ends of the medial ethmoid probe of the present invention. The medial ethmoid probe (60) is displayed in FIG. 26A. This probe has a handle (61) and shaft (62 and 62') on both sides of the handle. The shaft is made of a rigid material such as metal or plastic. The distal segment (63 or 63') of either end may be of rigid or semirigid material. The distal segment is preferably made from a polymer including but not limited to silicone rubber, polyurethane, polyethylene terephthalate, polyethylene, polypropylene, polyvinyl chloride, polymethyl methacrylate and polytetrafluoroethylene. The distal segment (63) curves to a final angle (64) of less than 110 degrees to the axis of approach. Preferably, the angle (64) is between 20 degrees and 80 degrees. More preferably, the angle (64) is between 30 and 60 degrees. FIG. 26B shows a distal segment (63) that is angled superiorly approximately 30 degrees (64) from the axis of approach. It is noted that the angles (64 and 64') may be the same or different. The length of the distal segment (63 or 63') preferably ranges from approximately 0.5 cm to 2.0 cm, more preferably from 0.7 cm to 1.5 cm, and most preferably about 1.2 cm. The materials, curvatures, angles, and lengths as defined facilitate atraumatically maneuvering the distal segment within the hiatus semilunaris superior (HSS) to engage the ethmoid bulla ostium (EBO) with the curved tip (66), shown in higher magnification in FIG. 26C In one embodiment of the present invention, the concave surface of the distal tip (66) and distal segment (63) may be wedge-shaped in profile, to facilitate deforming or stretching the medial margin of the ethmoid bulla ostium (EBO) when the instrument is pulled toward the operator while engaging the ostium (see FIGS. 23A-23C and discussion below.) The function of the medial ethmoid probe (60) is to palpably identify an ostium concealed (as it usually is) on the posterior aspect of the ethmoid bulla (EB) and to enlarge it medially and anteriorly so that it can be seen and therefore treated more definitively.

Manipulation of the medial ethmoid probe (60) is depicted in FIGS. 22A-22C. In the method of the present invention, the medial ethmoid probe is grasped by handle and the shaft and distal segment are introduced into the nose. The distal segment (63) of the medial ethmoid probe (60) is inserted into the hiatus semilunaris superior (HSS) and with the manipulated such that the curved tip (66) engages the rim of the ethmoid bulla ostium (EBO). The procedure is facilitated owing to the angulations and material composition outlined previously for the medial ethmoid probe (60). This interaction is easily palpated and occasionally directly visualized. If a shallow angulation (64) of medial ethmoid probe (60) (e.g., 30 degrees) is not able to engage the ostium, a steeper angle (e.g., 60 degrees) is used.

Figure 23A:
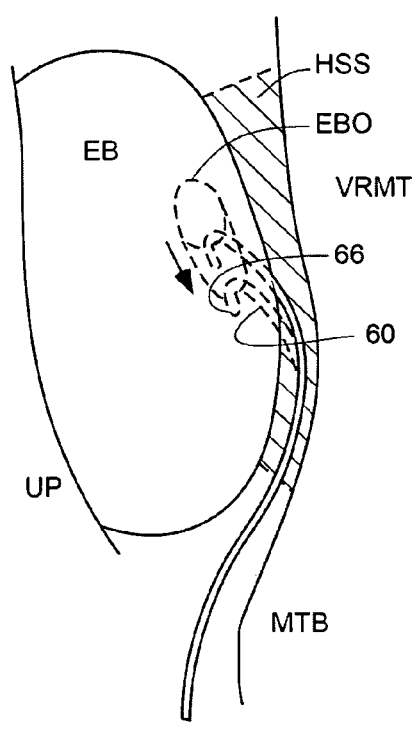
FIGS. 23A-23C illustrate three views (endoscopic, sagittal, traverse) of expansion of the ethmoid bulla ostium using an ethmoid probe of the present invention.
Figure 23B:
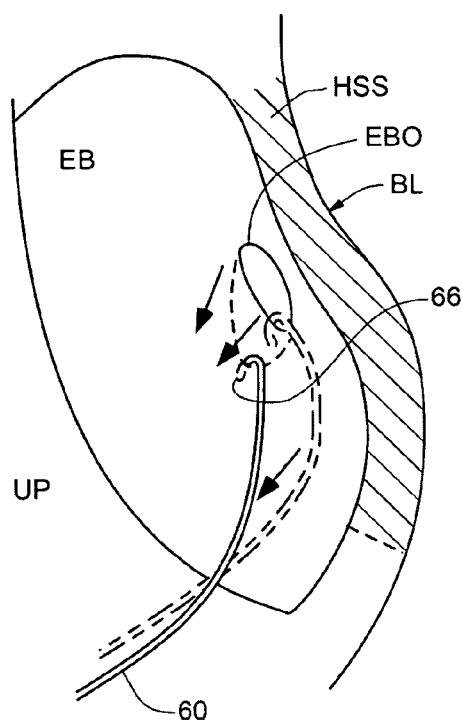
Figure 23C:
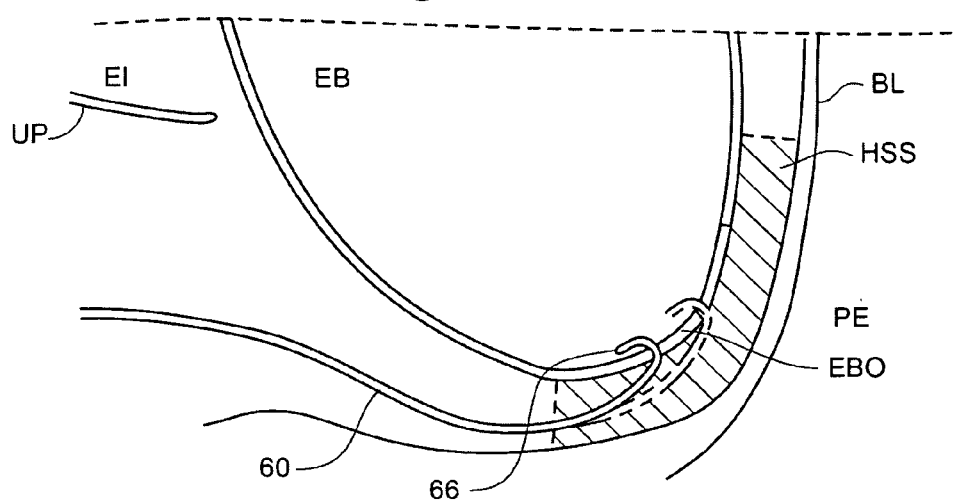
Figure 24A:
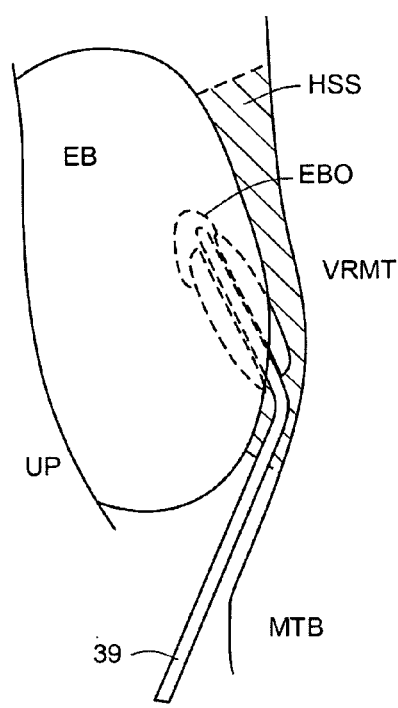
FIGS. 24A-24C illustrate three views (endoscopic, sagittal, traverse) of dilating the hiatus semilunaris superior using a guide-free dilator, in accordance with one aspect of the present invention.
Figure 24B:
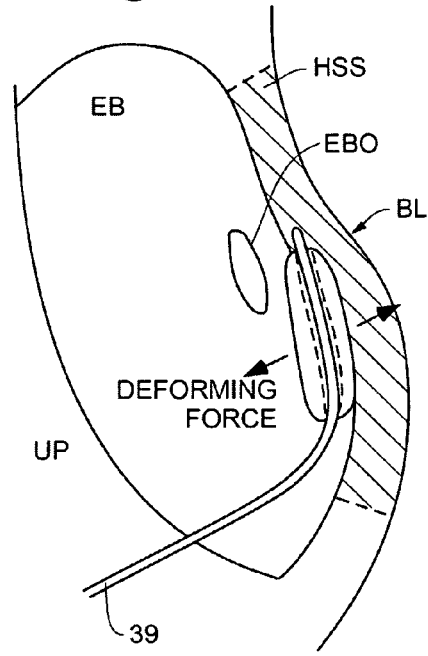
Figure 24C:
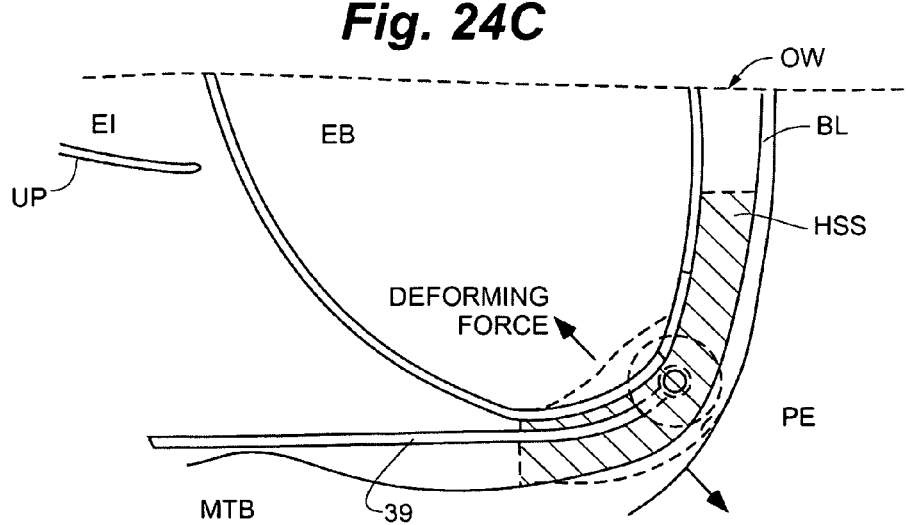
Figure 25A:
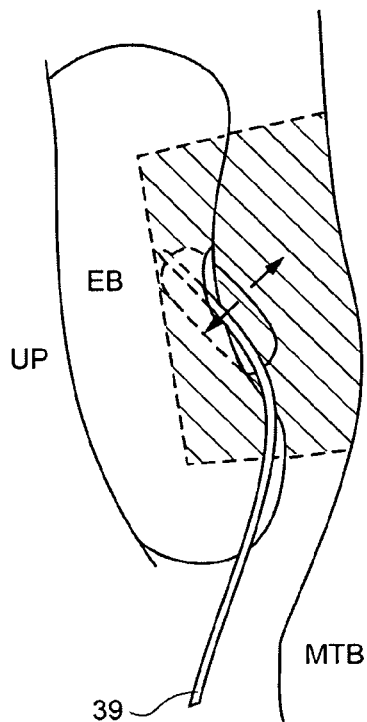
FIGS. 25A-25C illustrate three views (endoscopic, sagittal, traverse) of dilating the ethmoid bulla ostium using a guide-free dilator, in accordance with one aspect of the present invention.
Figure 25B:
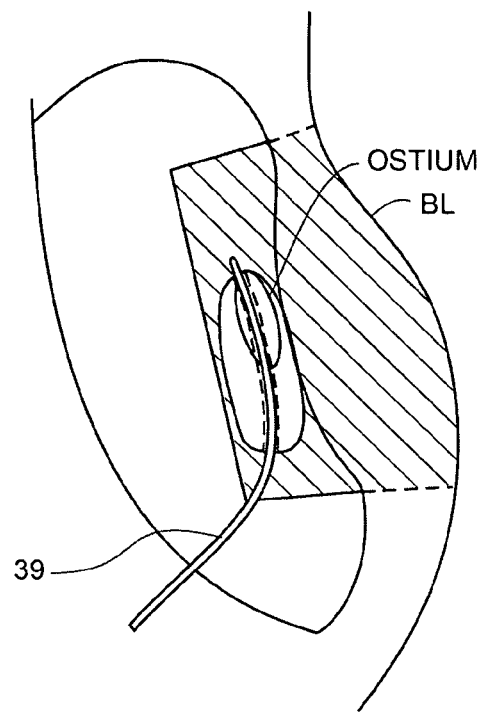
Figure 25C:
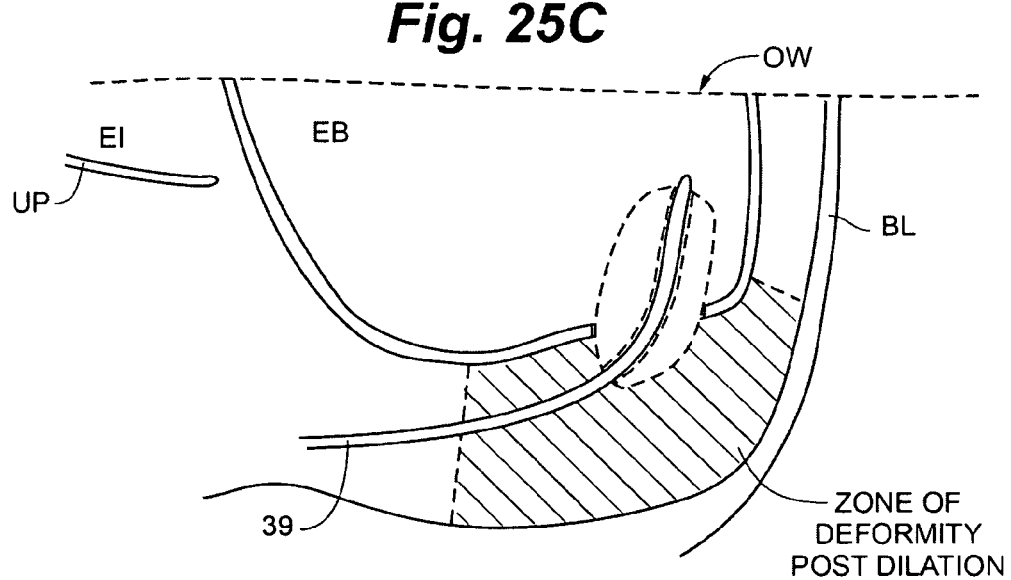

In most cases, the ethmoid bulla ostium (EBO) can be identified at this point and stretched open with a gentle posterior to anterior traction, indicated by the solid arrow in FIGS. 23A-23C. In FIGS. 23A-23C, the starting point of medial ethmoid probe (60) is shown with dotted lines and the ending point is depicted with a solid line. The traction maneuver is facilitated by a cutting edge on the inner curvature of the distal tip (66) and distal of the medial ethmoid probe (60). Once identified and gently stretched, the ethmoid bulla ostium (EBO) of the hiatus can usually be seen. Whether or not the ostium is directly visualized at this point, the tip of the guide-free dilator (39) of the present invention can be passed into the hiatus semilunaris superior (HSS)—i.e., the space between the ethmoid bulla (EB) and the basal lamella (BL)—and expanded (FIGS. 24A-24C). The guide-free dilator (39) is depicted in FIG. 15A and was discussed in reference to the maxillary sinus embodiments. Expansion of the guide-free dilator (39) leads to dilation of the hiatus semilunaris superior (HSS), widening the narrow cleft into which the ethmoid bulla ostium (EBO) drains and improving further access to the ostium itself. Now that the ethmoid bulla ostium (EBO) can, in most cases, be directly seen, it is entered under direct vision with the tip of the guide-free dilator (39) and dilated (FIGS. 25A-25C). Alternatively, cannulating and dilating the ostium with the guide-free dilator of the present invention may succeed in also dilating the hiatus semilunaris superior (HSS) in a single-maneuver if the ostium can be easily visualized after the stretching maneuver outlined earlier. Regardless, as shown in FIGS. 25A-25C, expansion of the dilator widens the hiatus semilunaris superior (HSS) leading to a zone of deformity (shaded region in FIGS. 25A-25C).

Despite appropriate efforts, the medial approach occasionally will not gain reliable access to the ethmoid bulla ostium (EBO), usually because the ostium is placed exceptionally superior and lateral on the posterior wall of the bulla. In such cases, in accordance with another aspect of the present invention, an anterior keyhole perforation is created. The anterior keyhole approach is preferably performed after dilation of the hiatus semilunaris superior (HSS) using the medial approach described above. Alternatively, the anterior keyhole approach may be performed prior to dilation of the hiatus semilunaris superior (HSS).

The anterior keyhole approach is depicted in FIGS. 27-33. As described above, each of these figures depicts three separate views of the relevant anatomy surrounding the ethmoid bulla (EB). For ease of approach, the surgeon attempts to remain as lateral as possible, while still medial to the free posterior margin of the uncinate process (UP). The point (marked by asterisk in FIG. 27) chosen is also just below the "equator" of the ethmoid bulla (FIG. 27A-27C, dashed line)—i.e., the anterior extent of the convexity of the anterior wall of the bulla at about the midpoint of its inferior-to-superior height—yet above the pathway of mucus exit from the ethmoid infundibulum (EI). As a practical matter, this places the perforation in the inferolateral quadrant of the visible anterior wall of the ethmoid bulla (EB). The chosen site has the advantage of affording the best view of any ostium likely to escape probing from the medial aspect (i.e., a superior and lateral ostium placement) while also remaining out of any known common drainage pathway for the anterior ethmoid, frontal, or maxillary sinuses.

Figure 27A:
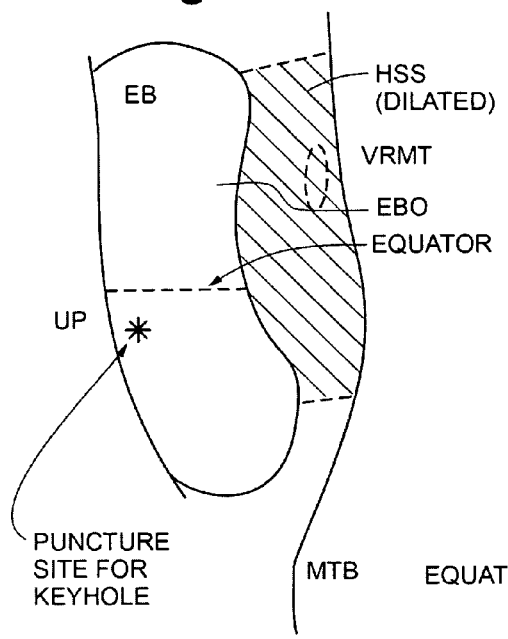
FIGS. 27A-27C illustrate three views (endoscopic, sagittal, traverse) of the desired site of the 'keyhole' in the wall of the ethmoid bulla, using the anterior keyhole approach of the present invention.
Figure 27B:
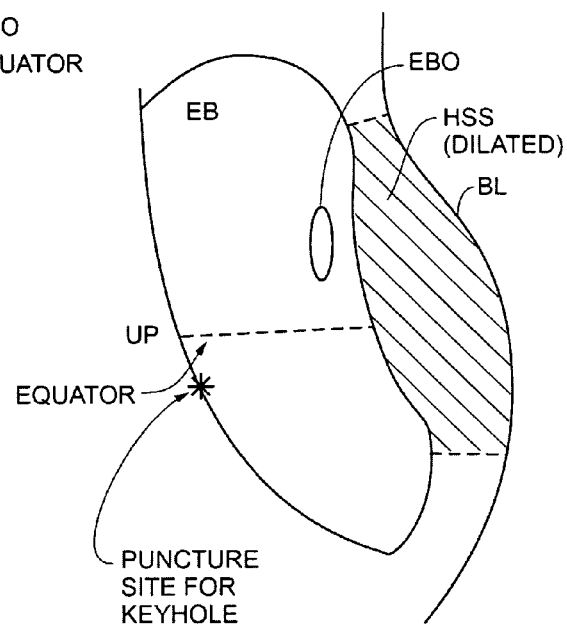
Figure 27C:
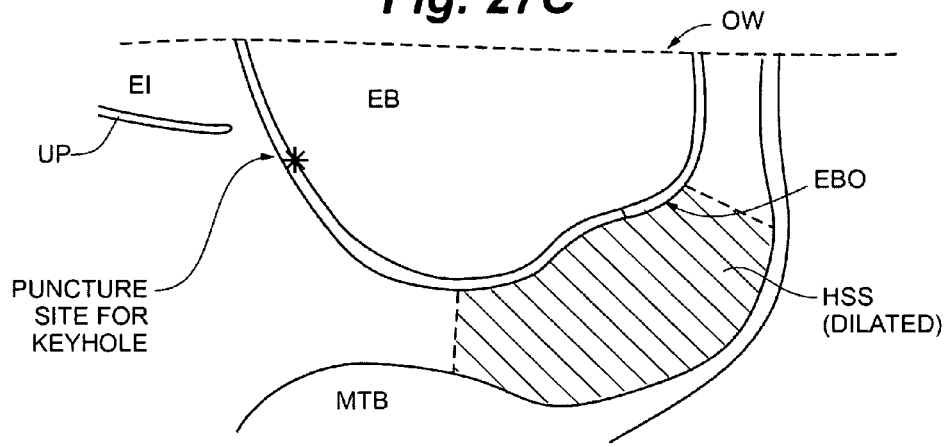
Figure 34:
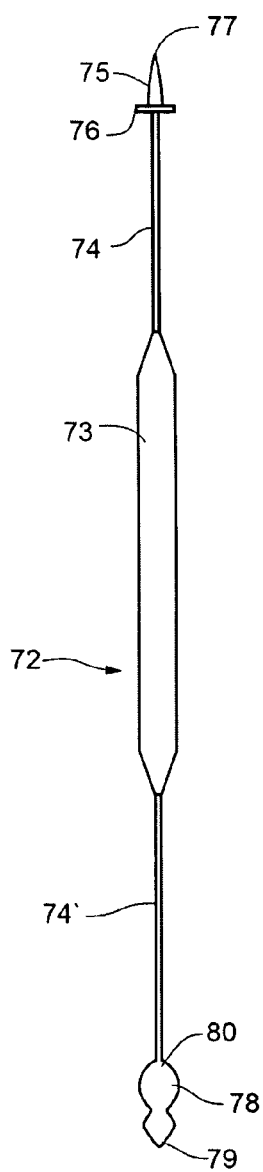
FIG. 34 illustrates an ethmoid keyhole probe of the present invention.

As shown in FIGS. 28A-28C, a perforation is made in the wall of the ethmoid bulla (EB) at the site indicated in FIGS. 27A-27C. Such a perforation may be accomplished using the ethmoid keyhole probe of the present invention, depicted in FIG. 34. Ethmoid keyhole probe (72) is composed of entirely rigid materials and consists of a handle (73) with a thin shaft (74 and 74') on both ends. One end mounts a perforator tip (75) with a stop collar (76). The perforator tip terminates in a sharp pointed end (77) that is ideal for making a small perforation in the bone. The distance from the pointed end (77) to the stop collar (76) is preferably less than 1.0 cm and most preferably about 0.5 cm. The other end mounts a dilator tip (78) that is bluntly tapered at the distal end (79) and rounded at its proximal end (80). The tapered distal tip (79) has a smaller diameter than the rounded proximal end (80) which is itself not more than 0.5 cm in diameter. As will be apparent from the figures below, the ethmoid keyhole probe (72) depicted in FIG. 34 serves the dual purpose of making the perforation in the wall of the ethmoid bulla (EB) and dilating the resultant perforation. However, in accordance with another aspect of the present invention, the perforation and dilation can be accomplished with separate instruments.

Perforation of the wall of the ethmoid bulla (EB) using the anterior ethmoid keyhole method of the present invention is depicted in FIGS. 28A-28C. In these figures the pointed end (77) of the perforator tip (75) of the ethmoid keyhole probe (72) engages the anterior wall of the ethmoid bulla (EB) at the chosen site (see FIGS. 27A-27C) and penetrates the wall into the antrum of the ethmoid bulla (EB). The stop collar (76) limits the extent of penetration.

Figure 29A:
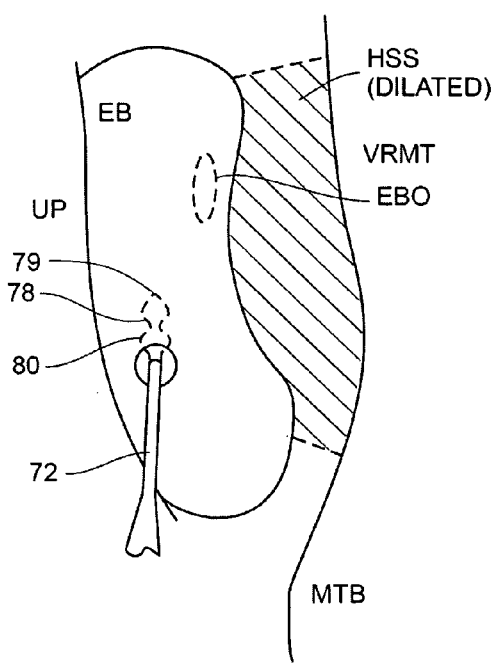
FIGS. 29A-29C illustrate three views (endoscopic, sagittal, traverse) of dilating the perforation in the wall of the ethmoid bulla using the ethmoid keyhole probe of the present invention.
Figure 29B:
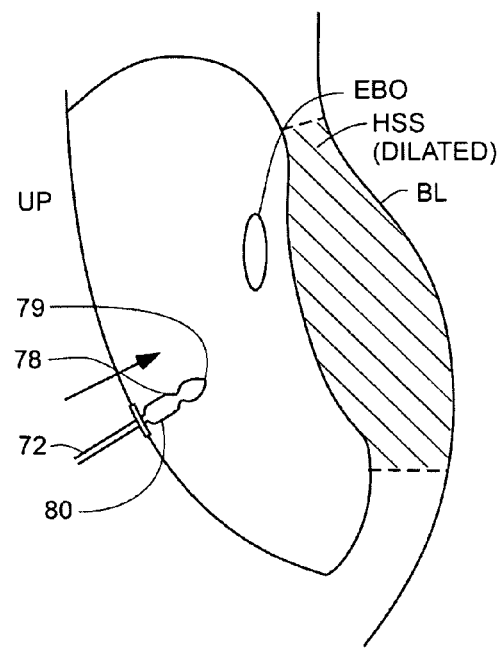
Figure 29C:
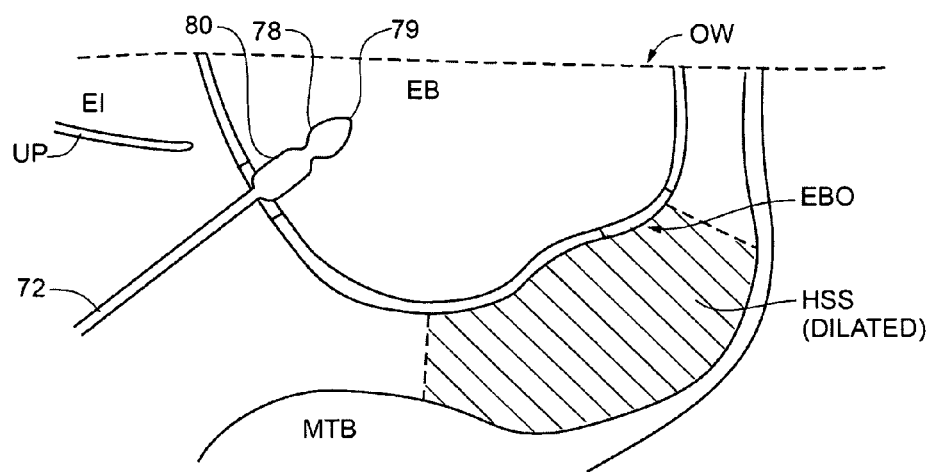
Figure 30A:
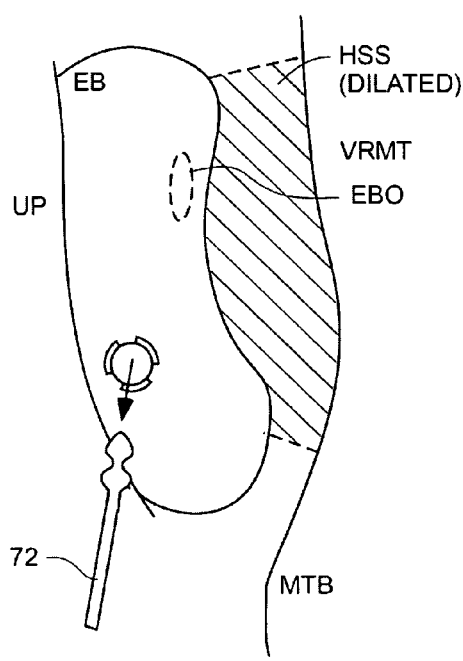
FIGS. 30A-30C illustrate three views (endoscopic, sagittal, traverse) of removing the ethmoid keyhole probe of the present invention following dilation.
Figure 30B:
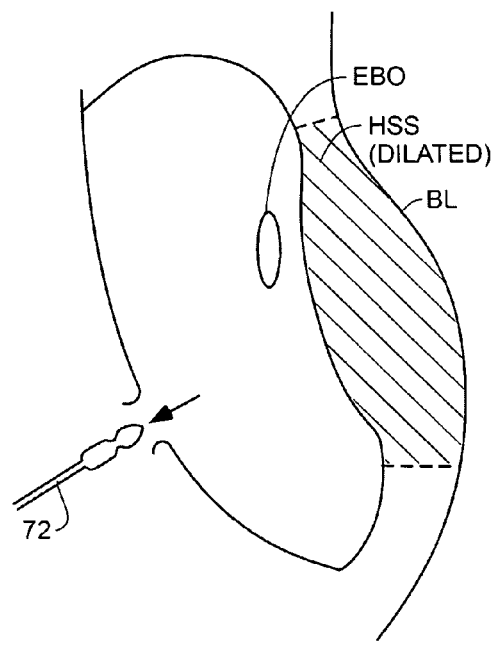
Figure 30C:
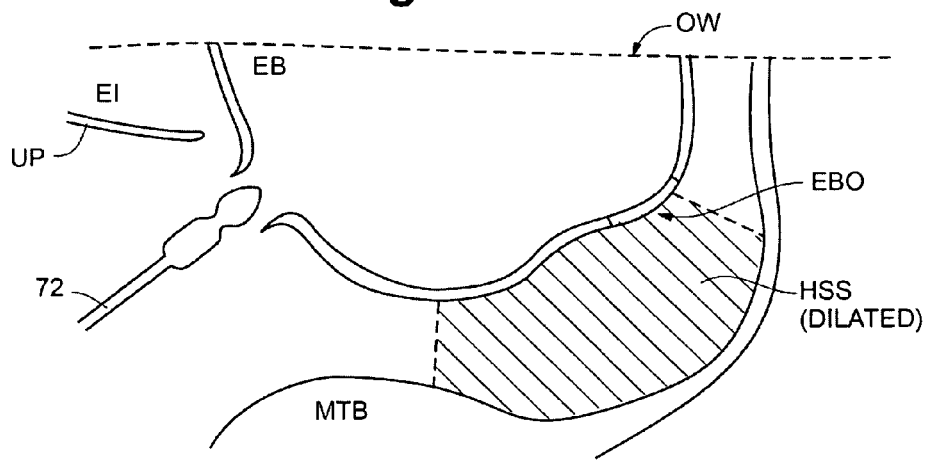
Figure 31A:
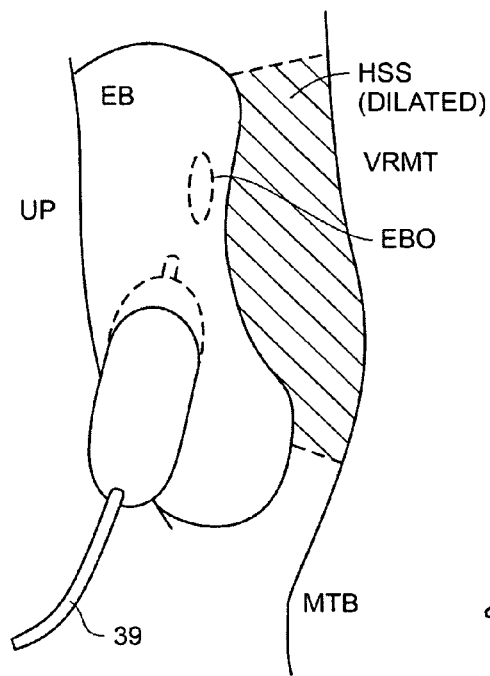
FIGS. 31A-31C illustrate three views (endoscopic, sagittal, traverse) of enlarging the perforation in the wall of the ethmoid bulla using a guide-free dilator, in accordance with one aspect of the present invention.
Figure 31B:
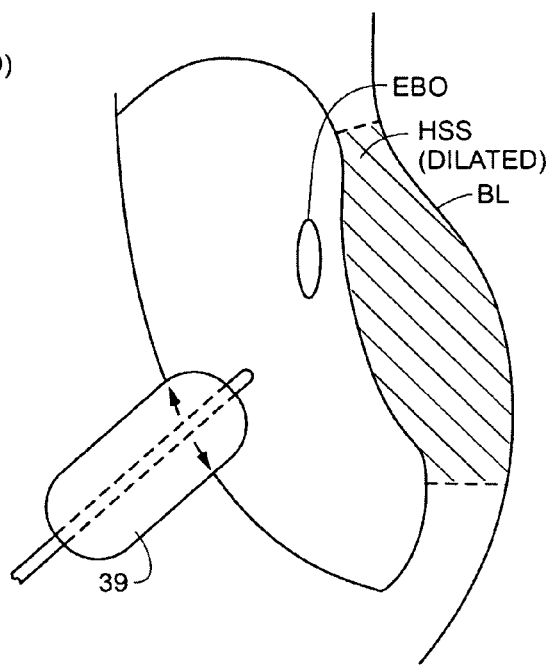
Figure 31C:
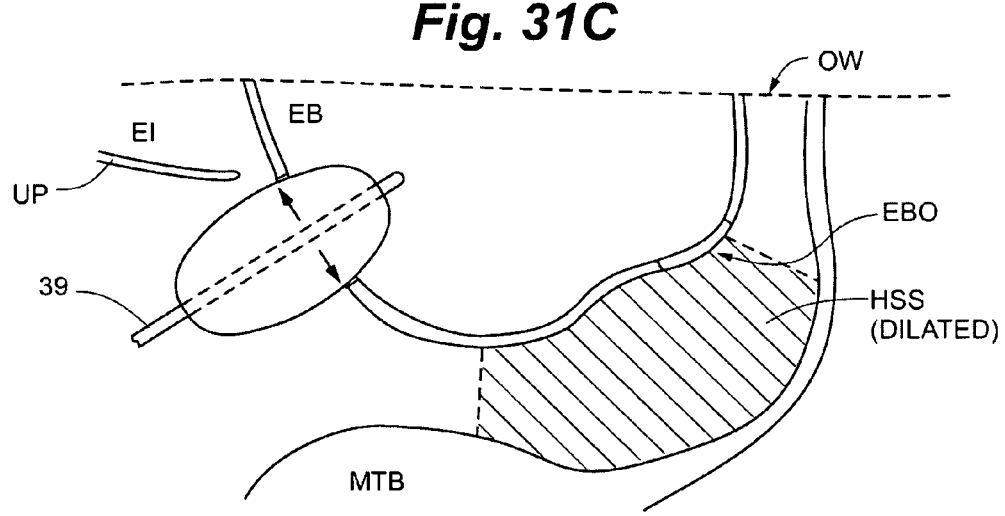
Figure 32A:
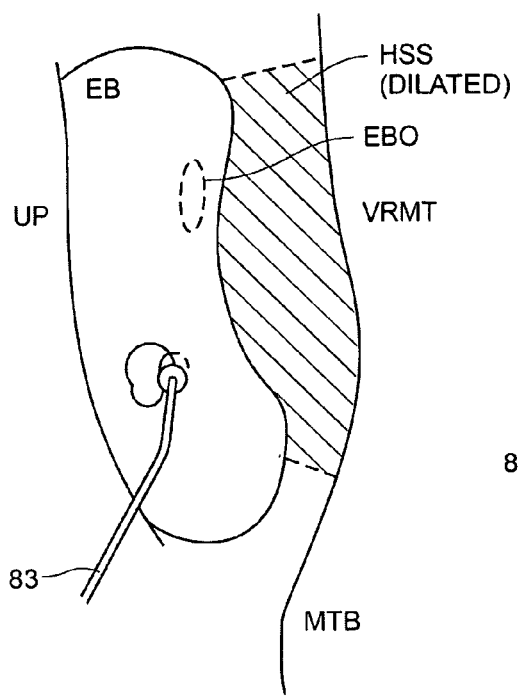
FIGS. 32A-32C illustrate three views (endoscopic, sagittal, traverse) of enlarging the perforation in the wall of the ethmoid bulla using a sphenoid punch, in accordance with one aspect of the present invention.
Figure 32B:
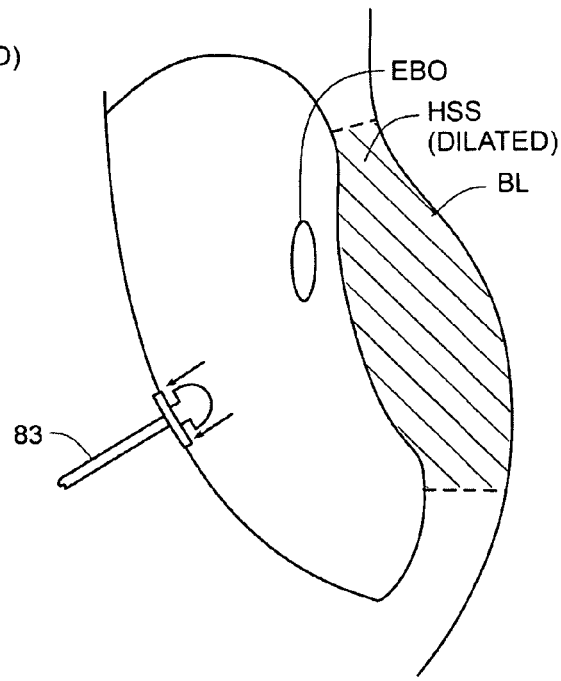
Figure 32C:
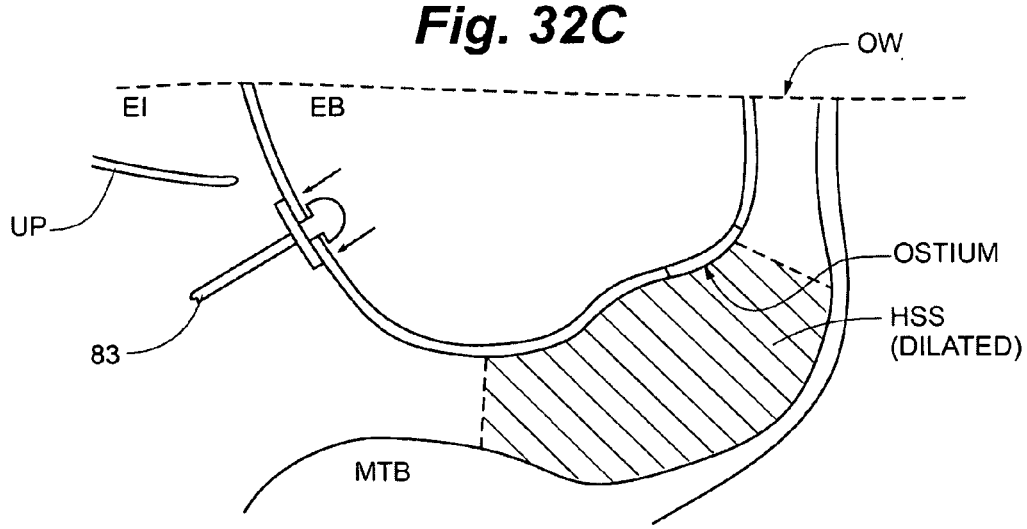

As shown in FIGS. 29A-29C, the ethmoid keyhole probe (72) then is withdrawn, inverted and the dilator tip (78) of the ethmoid keyhole probe (72) is introduced completely into the ethmoid bulla antrum through the perforation. The ethmoid keyhole probe (72) is then withdrawn (FIGS. 30A-30C), everting the mucosa of the wall. At this point, the perforation can be enlarged with the guide-free dilator (39) of the present invention (FIGS. 31A-31C). Alternatively, as depicted in FIGS. 32A-32C, dilation of the perforation may be accomplished with a conventional sphenoid punch (83). For example, a 19.5 centimeter sphenoid punch can be obtained from V. Mueller, catalog no. RH550-452. Note that while the guide-free dilator (39) expands to a predetermined diameter, the sphenoid punch (83) can incrementally remove smaller amounts of tissue to a desired stopping point, at the discretion of the surgeon. Although this yields control of size, it does so by cutting rather than stretching tissue and therefore likely generates a little more bleeding than the dilator.

Figure 33A:
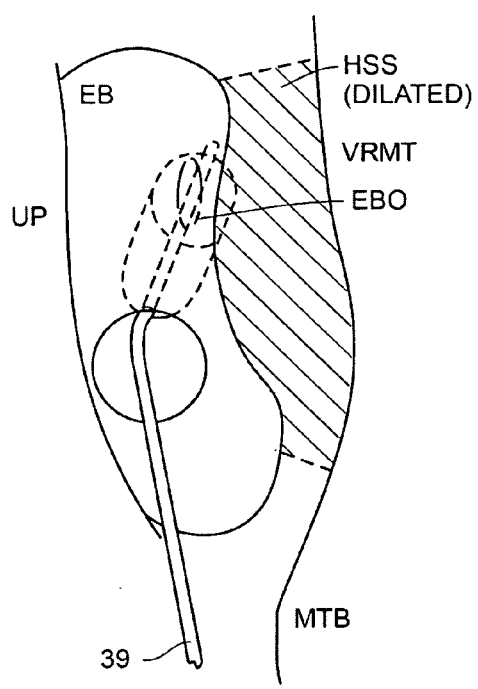
FIGS. 33A-33C illustrate three views (endoscopic, sagittal, traverse) of enlarging the ethmoid bulla ostium using a guide-free dilator, in accordance with one aspect of the present invention.
Figure 33B:
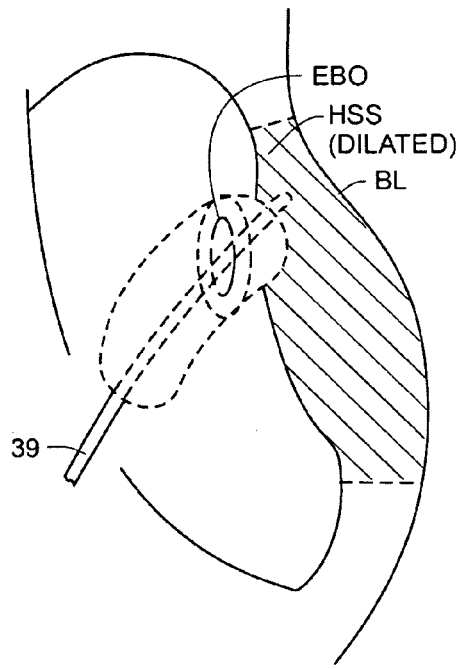
Figure 33C:
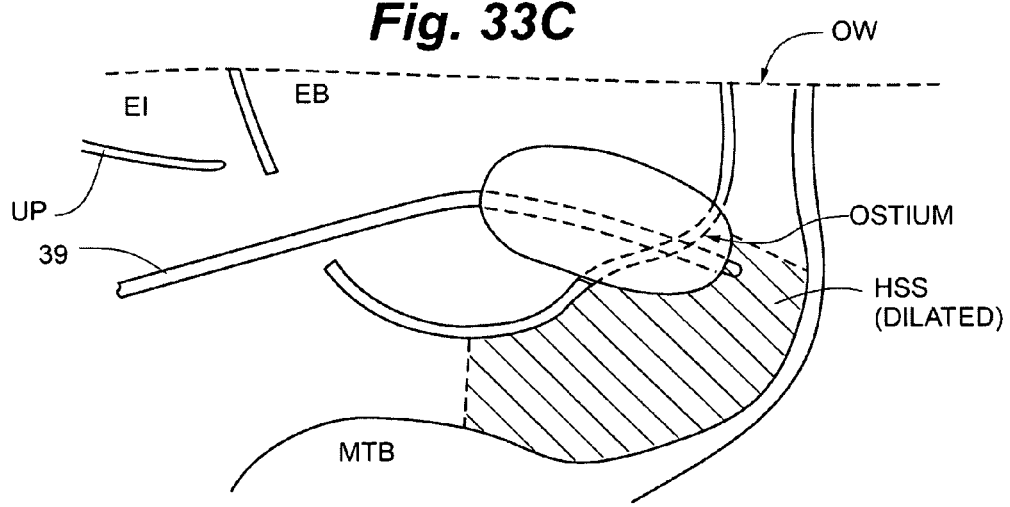

Referring back to FIG. 31 or 32, dilation of the keyhole should provide enough exposure to identify, cannulate, and dilate the ethmoid bulla ostium (EBO). Hence, similar to the maxillary sinus embodiments discussed above, the guide-free dilator (39) is introduced through the perforation and the ethmoid bulla ostium (EBO) is dilated (FIGS. 33A-33C). It should be noted that the success of this approach may depend on previously achieving the dilation of the space of the hiatus semilunaris superior (HSS) from the medial approach, much as the success of maxillary sinus approaches depends not only on dilation of the natural ostium but also on dilation of the ethmoid infundibulum (EI). (cf. FIGS. 16A-16C and FIGS. 24A-24C and FIGS. 25A-25C). The ethmoid keyhole approach gives the surgeon exposure to the ostia from both anterolateral (inside the ethmoid bulla) and posteromedial (outside the bulla, in the HSS). In many cases, this increased exposure will be crucial to knowing the job was accomplished. One can tell by working from the outside first, as in the described method, and if adequate ostium dilation can not be effected easily, gain the improved exposure through the keyhole, while still limiting or eliminating resection of tissue.

The other major cells of the anterior ethmoid bear some discussion. The space often styled the "sinus lateralis" can also be subdivided into fairly distinct suprabullar and retrobullar recesses. Fortunately, these spaces have fairly broad communication with the nasal vault in most cases; in any case, significant disease in these areas does not lend itself to minimally invasive approaches. Similarly, other more distal cells of the anterior ethmoid often communicate with the aforementioned spaces and the ethmoid bulla (EB). Accordingly, procedures described above for dilating the ethmoid bulla ostium (EBO) and the hiatus semilunaris superior (HSS) should mitigate blockage of these cells as well.

Figure 35A:
FIGS. 35A-B illustrate alternative embodiments of a guide-free dilator of the present invention.
Figure 35B:
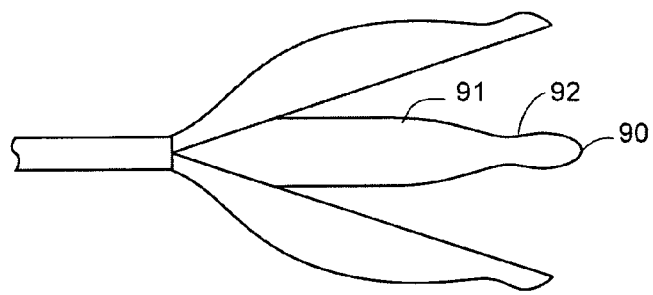

The agger nasi (AN) also bears special mention. When present, the agger nasi (AN) is found lateral to the superior uncinate and has a separate drainage pathway inferiorly, into the ethmoid infundibulum (EI). It can easily be dilated during the maxillary procedure, if desired, by directing the tip of the guide-free dilator (39) of the present invention superiorly, into the antrum of that cell. The proximal end of the frontal recess is usually positioned posteromedial to its posteromedial wall; hence, the agger nasi (AN) and frontal sinus are often involved synchronously with inflammation. For this reason, one must be quite careful regarding the use of dilators in this area, so as not to have the improved drainage of one area compromise the patency of the other. Alternatively shaped guide-free dilators of FIGS. 35A-B may be of particular use in this area as they allow for more limited, small-diameter dilation. Such a dilator tip might be mounted on a carriage similar to that of the backbiting hole punch (FIG. 9H) or of the drug delivery devices (FIGS. 38A and 39A) of the present invention, enabling similar maneuverability within the nose. The distal tip (90) is rounded in order to allow atraumatic advancement into the visualized ostium. Just proximally, the dilating flanges (91) taper to a neck (92) to facilitate seating them in the ostium when they are expanded to dilate it (FIG. 35B). Many different mechanisms to obtain the expansion of the flanges (91) are contemplated.

Access to the Frontal Sinus

As noted above, the frontal sinus is sometimes inflamed in concert with, and probably as a result of, inflammation in the anterior ethmoid. As such, in the minimally invasive arena, frontal sinusitis can often be treated purely by appropriate treatment of the anterior ethmoid, as outlined above, or with procedures of the prior art. There are circumstances, however, in which direct dilation of the frontal sinus ostium is desirable. An appropriately trained practitioner of the routine sinus art can directly visualize the frontal ostium in a predictable manner using a 70 degree endoscope. Subsequently, the curved rigid-semirigid balloon dilator (39) of the present invention can be passed into the ostium under direct vision and without resort to a guide. As in the above approaches, a significant advantage to the dilator of the present invention is that it can be manipulated just like the probe employed in frontal sinus identification in routine sinus procedures.

Figure 36A:
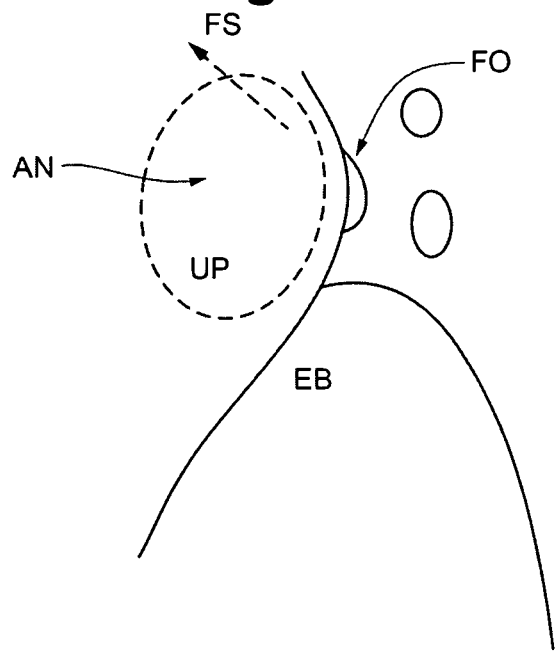
FIG. 36A illustrates an endoscopic view (70 degrees) of introducing an endoscope into the region surrounding the frontal sinus, in accordance with one aspect of the present invention.
Figure 36B:
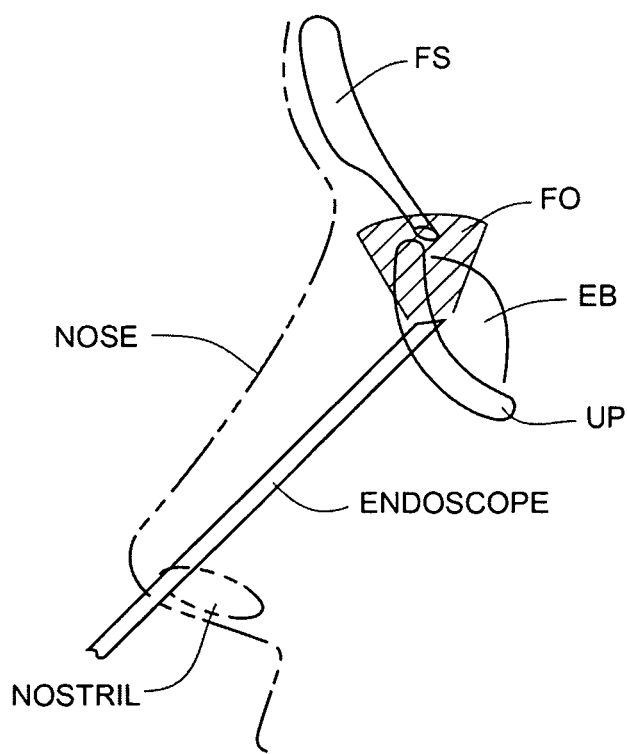
FIG. 36B illustrates a sagittal view of introducing an endoscope into the region surrounding the frontal sinus, in accordance with one aspect of the present invention.
Figure 37A:
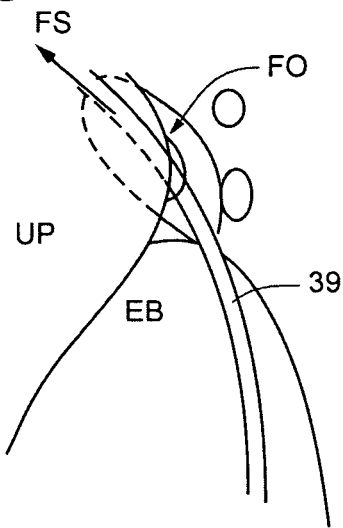
FIG. 37A illustrates an endoscopic view (70 degrees) of advancement of a guide-free dilator of the present invention into the frontal ostium followed by dilation, in accordance with one aspect of the present invention.
Figure 37B:
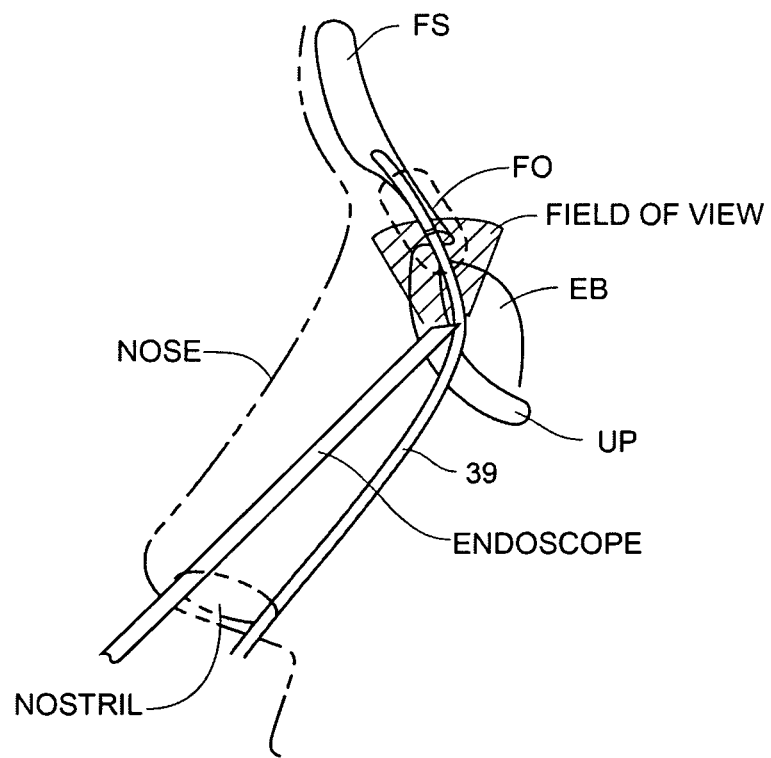
FIG. 37B illustrates a sagittal view of advancement of a guide-free dilator of the present invention into the frontal ostium followed by dilation, in accordance with one aspect of the present invention.

The frontal sinus procedure of the present invention is depicted in FIGS. 36 and 37. These figures each show two views of the relevant anatomy around the frontal sinus, an endoscopic view (70 degrees) (FIGS. 36A and 37A) and a sagittal projection (FIGS. 37A and 37B). In the Figures, the relevant anatomy is indicated, particularly the frontal sinus (FS) and frontal ostium (FO). The shaded cells in the figures are small ethmoid air cells. The frontal approach is likely best accomplished before the maxillary sinus and ethmoid infundibulum are addressed. After anesthesia and middle turbinate retraction are achieved, as described above, a 70 degree endoscope is advanced into the middle meatus just medial to the mid portion of the uncinate process, with the view directed superiorly (FIG. 36B). The frontal ostium is generally found posteromedial and superior to the posteromedial and superior aspect of the agger nasi cell (FIG. 36A). The guide-free dilator (39) can then be directed superior, lateral, and anterior and passed into the ostium under direct endoscopic vision (FIGS. 37A-37B). The appearance and position of the ostium are fairly characteristic to the trained practitioner of the prior routine sinus art, but, as there may be confounding adjacent small ethmoid cells present, it would be appropriate at this point to verify placement in the true frontal sinus ostium via fluoroscopy or other means. Dilation can then be accomplished. Anatomic variations can be seen. Exhaustive treatment of the variations is beyond the intended scope of this description, but suffice it to say that the person of ordinary skill in the art will recognize that the dilator of the current invention can be used to treat other anatomic locations of the ostium in analogous fashion to the above description.

Access to the Posterior Ethmoid

Definitive and directed treatment of this area is not often required in the minimally invasive arena, but certainly is amenable to the use of the guide-free dilator device of the current invention. The drainage pathways of the posterior ethmoid are quite variable and need to be assessed on a case-by-case basis. One constant to the variation is that mucociliary flow proceeds from the superolateral to the inferomedial direction, exiting in the superior meatus. This area can be endoscopically assessed using a 70 degree endoscope passed medial to the middle turbinate and with the view directed laterally. The ostia and recesses of the posterior ethmoid often can be seen with this approach and dilation can be accomplished with the guide-free device under direct vision as deemed necessary and appropriate.

Access to the Sphenoid Sinus

As in the posterior ethmoid sinuses, the sphenoid does not frequently require treatment in the minimally invasive arena. Nonetheless, the sphenoid sinus ostium can be identified posterior and superior to the body of the superior turbinate by appropriately trained practitioners of the routine sinus surgical art. This site is visualized with a 0 or 30 degree endoscope passed medial to the middle and superior turbinates with the view directed laterally, if the angled scope is needed. The guide-free dilator (39) of the current invention is well-suited to direct passage into the visualized ostium. As in the frontal sinus, proximity to vital structures and the concomitant hazard of significant morbid complications suggests that external verification of placement using fluoroscopy or other methods may be desirable in some cases before dilation is undertaken.

Delivery of Targeted Pharmacotherapy

As described in the Background section, it would be desirable to facilitate treatment of the sinuses with topical agents as, in an appropriate iteration, one would expect such treatment to be more effective and have fewer side effects than can be observed using an oral route of administration. Ideally, the means for delivery could be used on a repeated basis, if needed, with topical or no anesthesia, in an office setting. To that end, there is a need in the prior art for minimally traumatic and reliable access to the paranasal sinuses and for drug placement devices that are cost-effective and do not require later removal.

The anterior keyhole approach to the maxillary and anterior ethmoid sinuses and the medial approach to the ethmoid bulla outlined above satisfy the requirement for minimal trauma and reliability. Guide-free drug placement devices of the present invention allow the practitioner to take advantage of the keyhole access or direct visualization of the sinus ostia to place pharmaceuticals in solid, powdered, semisolid, or liquid biodegradable matrices within the appropriate sinus cavities. Of further benefit, the devices enable placement of the pharmaceutical strategically, in distal areas of the sinuses in question, so as to take advantage of the natural mucociliary clearance action of the sinus lining to spread the therapeutic agent throughout the sinus.

The action of placement of the therapeutic agents in each relevant sinus is entirely analogous to that noted above for the dilation of the sinus ostia, and is in general even simpler. The guide-free drug placement devices of this invention take advantage of the same angled anatomy as employed by the guide-free dilator of this invention and are easily manipulated by practitioners in similar fashion to accustomed probes of the routine sinus art.

In the maxillary sinus procedure of the present invention, topical infiltration anesthetics are placed. Infiltration anesthetics may also be used, but may not be needed if a keyhole or other antrostomy is already present. The creation of a keyhole is outlined in detail above and surgical maxillary antrostomies can be created according to the routine surgical art. Having established either type of opening into the sinus or by means of a naturally occurring accessory ostium, the surgeon utilizes a drug insertion device of the present invention to introduce either a drug or a drug-delivery device of the present invention into the maxillary sinus antrum. Two embodiments of drug insertion devices used in accordance with the present invention are depicted in FIGS. 38 and 39.

Figure 38A:
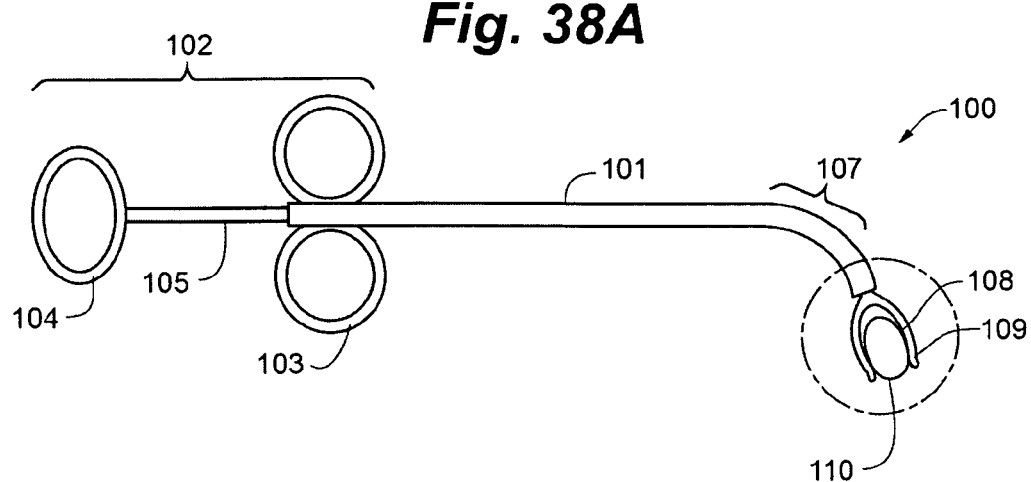
FIGS. 38A-C illustrate an embodiment of a guide-free drug placement device of the present invention.
Figure 39A:
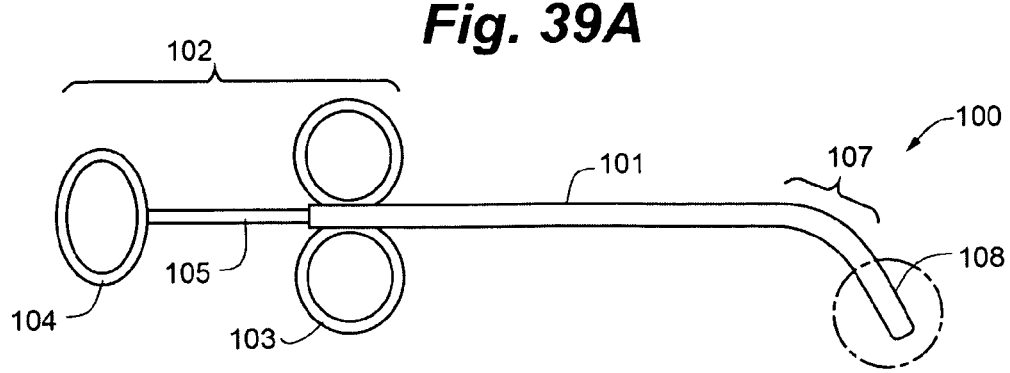
FIGS. 39A-C illustrate an alternative embodiment of a guide-free drug placement device of the present invention.
Figure 39B:
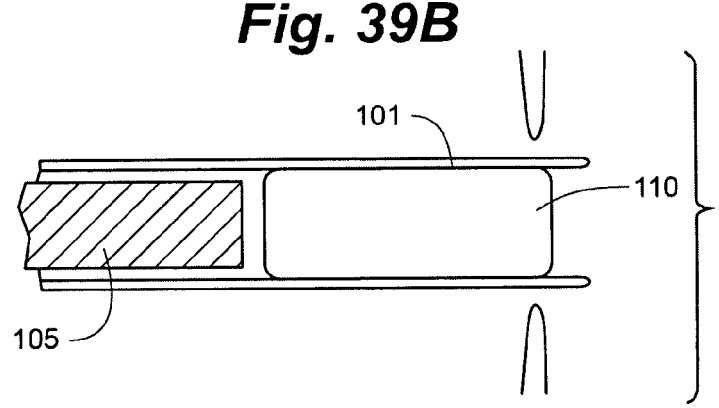

The drug insertion delivery instruments (100) depicted in FIGS. 38A and 39B share a number of common characteristics. Each consists of a rigid shaft (101) mounted on a handle assembly (102) held by the surgeon. Here the handle is depicted using a traditional syringe action with finger holes (103) to accommodate the surgeon's index and middle fingers and a plunger (104) for the thumb. The plunger (104) is squeezed toward the finger holes (103), advancing the piston (105) through the cylindrical shaft (101). Other mechanisms for the handle assembly are permissible as long as they succeed in advancing the piston (105). The shaft (101) angles distally at the intermediate segment (107). Appropriate angulations at this site are similar to those for the guide free dilator described above, but here the ideal angle is between about 55-60 degrees. This angle is specifically chosen to enable drug or drug device insertion through the keyhole in the maxillary sinus while also being able to easily accommodate a standard surgical maxillary antrostomy, naturally occurring accessory ostium, anterior ethmoid keyhole or patent medially dilated ethmoid bulla, as previously described in the methods of the present invention. All of the preceding items are of rigid construction, preferably using metal or plastic, except for the piston (105), which is flexible so as to accommodate the angled intermediate segment (107) of the shaft (101). Flexible plastic or malleable metal embodiments (as in a wire or spring) of the piston (105) are possible. In each device embodiment, the instrument terminates in a distal receptacle (108). The distal receptacle (108) segment is shown in the dotted circle of FIGS. 38A and 39A. The length of the receptacle (108) is preferably in the range of 1.0-2.0 cm with the most preferred length about 1.5 cm. The width is approximately 5 mm. These dimensions are chosen to allow the insertion device to negotiate the middle meatus and keyhole in a patient with otherwise intact anatomy.

Figure 38B:
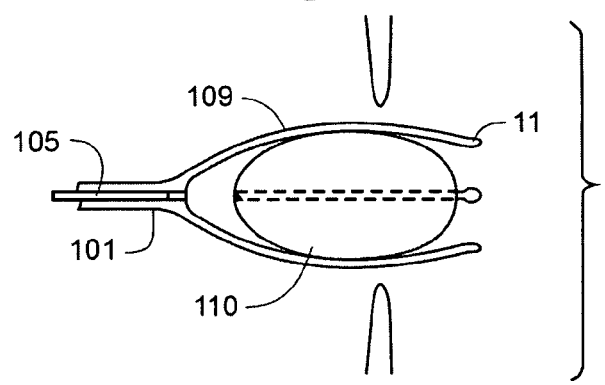
Figure 39C:
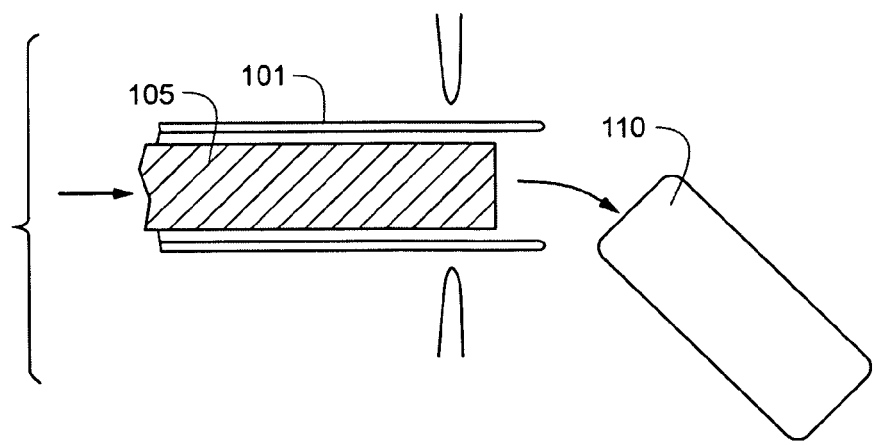

The distal receptacles (108) are rendered differently in the two embodiments depicted in FIGS. 38A and 39A. In the FIG. 38A embodiment, the receptacle (108) consists of several (at least 3) flexible flanges (109) which curve to grasp the drug (110) or drug delivery device. As shown in FIG. 38B, the drug (110) is initially held in distal receptacle (108) prior to drug delivery. As depicted in FIG. 39C, the flexibility of the flanges (109) allow them to spread apart when the piston (105) pushes the drug (110) or drug delivery device (e.g., drug in controlled release carrier) against the incurving distal tip (111), thus allowing the drug (110) or drug delivery device to be extruded from the now-open end of the insertion device. Again, flexible metal or plastic embodiments are preferable.

In the FIG. 39 embodiment, the receptacle (108) consists of a sleeve which wholly encompasses the drug or drug (110) delivery device but otherwise functions similarly to that in FIG. 38. The mechanism of action of pushing out the drug (110) or drug delivery device is shown in FIGS. 39B and 39C.

Figure 38C:
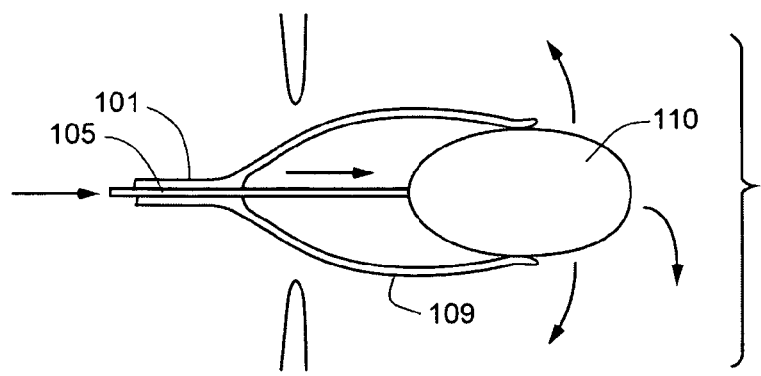
Figure 40A:
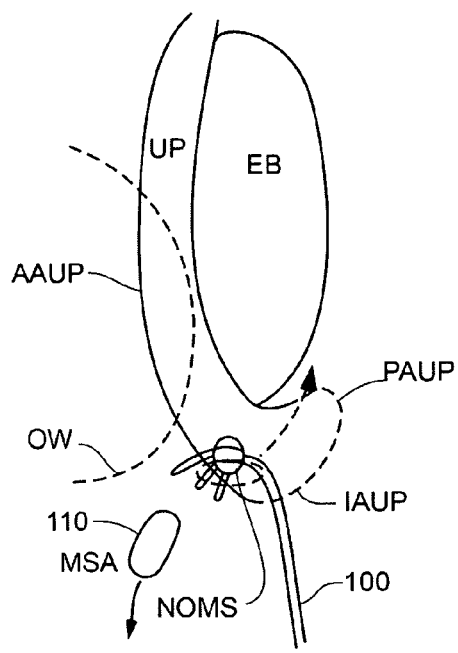
FIGS. 40A-40C illustrate three views (endoscopic, sagittal, transverse) of placement of a pharmaceutical agent in the maxillary sinus, in accordance with one aspect of the present invention.
Figure 40B:
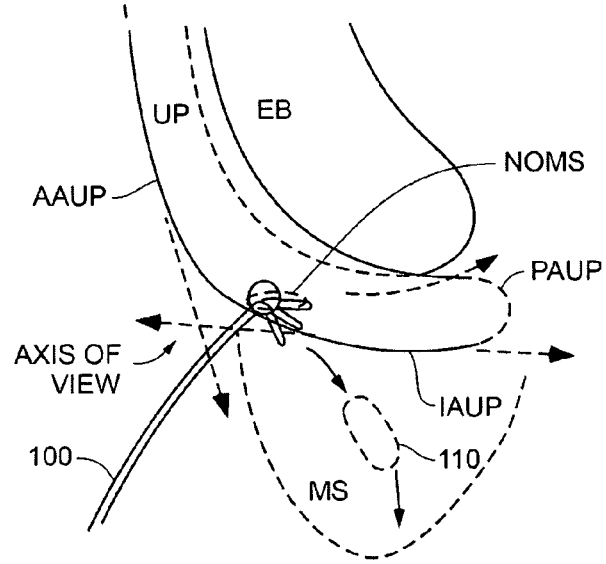
Figure 40C:
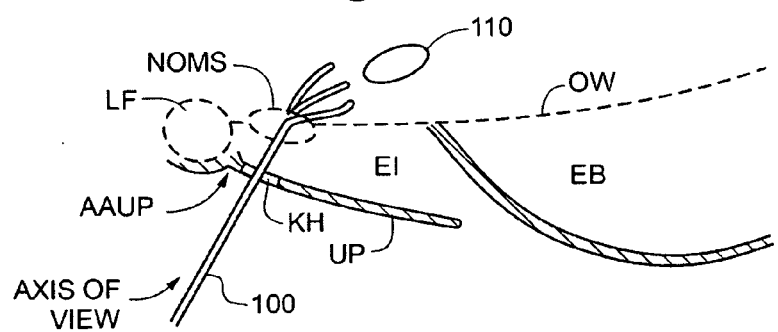

In the method of the present invention, the drug insertion instrument (100) is grasped by the handle assembly (102). The shaft (101), intermediate segment (107), and receptacle tip (108) of the drug insertion instrument (100) are introduced into the nose with a drug (110) or drug delivery device of choice loaded in the receptacle (108). The receptacle is directed through the keyhole (described above), antrostomy, or accessory ostium into the maxillary antrum (FIGS. 40A-C) in entirely analogous fashion to the introduction of the dilator in the previously described maxillary procedure of the present invention. As noted in the above description of the drug insertion instrument (100), the handle assembly (102) is manipulated so as to advance the piston (105) through the shaft (101), causing the drug (110) or drug delivery device to be inserted into the antrum (FIGS. 38C and 39C). The insertion device is then removed. The natural effect of gravity and the inferior orientation of the tip deliver the drug in the inferior apex of the sinus. Conveniently, this is an advantageous position for concentrating the drug where it is most helpful. The gravitationally dependent areas of the maxillary sinus are generally the most involved with inflammation. The drug may then distribute more generally via mucociliary action of the sinus lining.

Figure 41A:
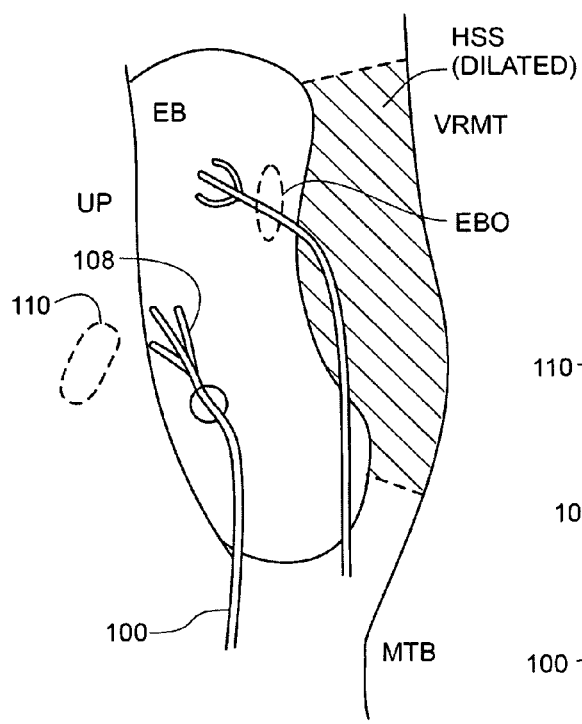
FIGS. 41A-41C illustrate three views (endoscopic, sagittal, transverse) of placement of a pharmaceutical agent in the anterior ethmoid sinus, in accordance with one aspect of the present invention.
Figure 41B:
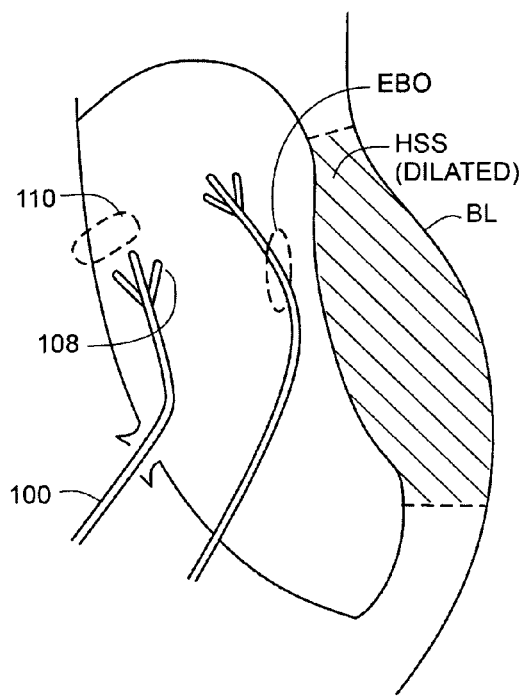
Figure 41C:
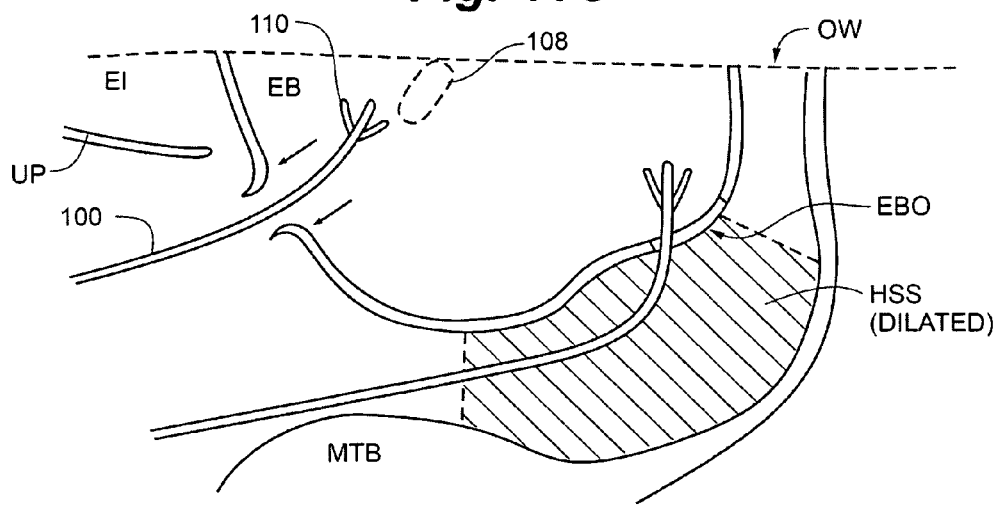

In the anterior ethmoid, topical or local infiltration anesthetics also can be used. Again, the middle turbinate will generally not need to be retracted in a stand-alone drug-placement procedure. If medial access to the bulla is already established, as outlined earlier in the method of the present invention (FIGS. 22-25), the drug insertion device can be introduced between the middle turbinate body and the bulla; the receptacle (108) is then advanced through the enlarged ethmoid bulla ostium (EBO) and directed lateral and posterior (FIGS. 41A-C). The drug (110) or drug delivery device is then released into the ethmoid bulla antrum. This lateral placement takes advantage of natural mucociliary movement. The insertion device is, however, versatile enough to allow strategic placement in a number of different directions. It is ideally suited, for example, to utilize the anterior keyhole of the bulla, if previously created (method outlined above), as access to the antrum of the ethmoid bulla. In this method, the receptacle tip (108) of the insertion device is introduced straight through the anterior wall of the bulla via the keyhole, entirely analogous to the use of the dilator in the anterior ethmoid keyhole method of the present invention (see FIGS. 31A-C).

The frontal, posterior ethmoid and sphenoid sinuses can be accessed with the placement device in entirely analogous fashion to the dilation procedures outlined above.

The present invention foresees the utility of sinus-specific biodegradable matrices for the delivery of topical pharmaceuticals for the sinuses. One would require that the matrix release medication over the interval of days-to-weeks, in sufficient concentration for effect, but without toxicity to the sinus mucosa. In particular, functional disruption of the gel-mucus interface with the cilia or alterations of ciliary motility would not be well tolerated. Of interest, substantially smaller doses of the active agents (e.g., antibiotics) than normally used orally might be highly effective topically given the immense advantage of concentration of action in this arena. Appropriate vehicles for drug release might include timed-release tablets, ointments, gels, creams, liquids, or powders. The parameters under which the release is achieved will be unique to the sinuses, both for the reasons noted above, and for the fact that the conditions anticipated in the sinuses have little in common with the enteric or intramuscular environment typically encountered by timed-release agents in humans.

Each of the drug delivery vehicles discussed above have their own problems, however. All are susceptible to rather rapid clearance by the natural mucociliary clearance function of the sinus lining. Furthermore, in the maxillary sinus with a large accessory ostium, or one previously operated with traditional techniques, and for the anterior ethmoid sinuses in general, gravity as well as mucociliary clearance may lead to early egress without some enhanced means of retention. Ideally, and as outlined below in an embodiment of the present invention, is a biodegradable retention framework that degrades at different rate than the drug matrix.

A drug delivery device of the present invention consists of a typical timed-release drug containing matrix coupled with a resorbable framework. The pharmaceutical industry has, over the years, developed biodegradable matrices for drug delivery, and the antibiotics and steroids considered for use in this arena are demonstrably active in the nose and have been coupled with biodegradable matrices in numerous oral preparations. As for the coupled framework, many materials are known to degrade in the nose over weeks-to-months, the ideal time interval for such a framework, including oxidized cellulose and polymerized sugars used in suture material. The polymers, in particular, maintain much structural integrity throughout a large part of the degradation interval and are relatively inert to nasal and sinus mucosa.

Several iterations of this drug delivery device have been conceived; these embodiments are illustrated in FIGS. 42-44. Each of these embodiments are configured so as to be utilized with the drug insertion instrument (100) of the present invention, but this relationship need not be exclusive. The central idea of a differentially degrading integrated retention framework coupled to a more traditional timed release drug matrix can certainly be adapted to other insertion systems, if desired, while still retaining its central advantages for topical therapies specifically in the sinuses. Ideally, any such device can be implanted easily under local anesthesia in the office, will elute drug over several weeks, and will resist the natural sinus mucociliary clearance to remain in place while pharmacologically effective. The illustrated embodiments and, by extension, analogous iterations, will fulfill these objectives admirably.

Figure 42A:
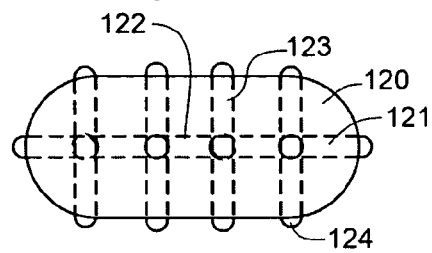
FIGS. 42A-B illustrate a front view and cross-sectional view, respectively, of a bioerodible drug delivery device of the present invention.
Figure 42B:
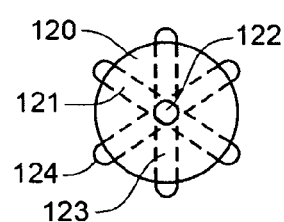

FIG. 42A shows the first embodiment of the drug delivery device of the present invention, consisting of a drug containing matrix (120) with an embedded degradable framework (121). The framework (121) is anchored by a spine (122) that follows the axis of the ellipsoid matrix. A series of ribs (123) protrude radially from the spine. Coplanar ribs (123) are depicted here as three in number, but could be more; ideally, no less than three would occupy a single transverse plane of the ellipsoid. Alternatively, the ribs (123) could stack in a spiral. The tip (124) of each rib would ideally protrude just past the surface of the matrix (120) in the nondegraded state. A cross-sectional view of the framework (121) is shown in FIG. 42B. As engineered, the framework (121) should degrade more slowly than the matrix (120) revealing more and more of the ribs (123). Thus, as the matrix resorbs and grows smaller, the retention device remains intact. The tips (124) of the ribs remain in contact with the sinus mucosa, but with considerably less surface area of contact than the matrix alone, thus decreasing the mucociliary clearance action by orders of magnitude. Once the matrix (120) is completely degraded, some framework (121) elements would be expected to remain for some finite interval before degrading completely themselves.

Figure 43A:
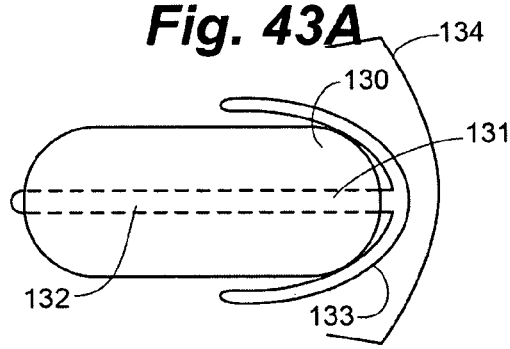
FIGS. 43A-B illustrate a front view and cross-sectional view, respectively, of an umbrella-type bioerodible drug delivery device of the present invention prior to delivery into the sinus.
Figure 43B:
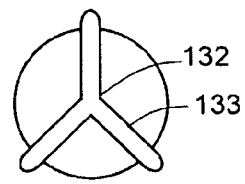
Figure 43C:
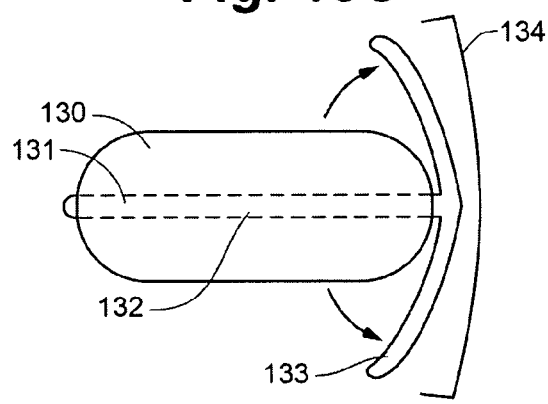
FIGS. 43C-D illustrate a front view and cross-sectional view, respectively, of an umbrella-type bioerodible drug delivery device of the present invention after delivery into the sinus.
Figure 43D:
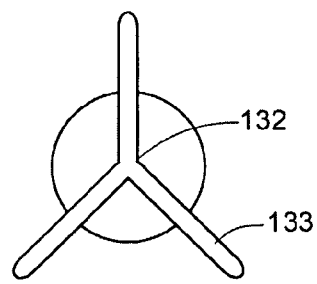

FIG. 43A shows the second embodiment of the drug delivery device of the present invention. FIG. 43B shows a cross-sectional view. The drug delivery device comprises a matrix (130) and an embedded degradable framework (131) design. In addition, this framework (131) is also anchored by a coaxial spine (132). Distinct from the embodiment depicted in FIG. 42A, however, is an expansile "umbrella" of ribs (133) also attached radially to the spine (132); here the attachment is outside the matrix (130) at one apex. The umbrella (134) is collapsed around the surface of the matrix (130) within the receptacle (see FIGS. 38 and 39) of the insertion device. As shown in FIG. 43C (and cross-sectional view FIG. 43D), the umbrella (134) then expands upon extrusion into the sinus. The retention and degradation properties of the drug delivery device are similar to those outlined in the discussion of the embodiment illustrated in FIG. 42A.

Figure 44A:
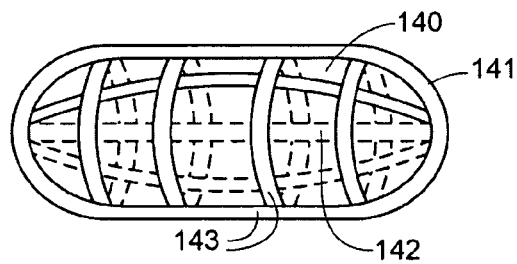
FIGS. 44A-B illustrate a front view and cross-sectional view, respectively, of an alternative embodiment of a bioerodible drug delivery device of the present invention.
Figure 44B:
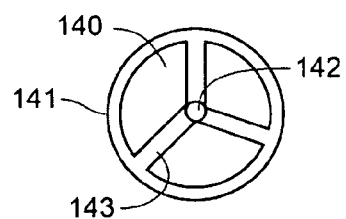

FIG. 44A shows the third embodiment of the drug delivery device of the present invention. FIG. 44B shows a cross-sectional view. The drug delivery device shares with the earlier embodiments the matrix (140) and embedded degradable framework (141) design. It, too, can be anchored by a coaxial spine (142), though this is not strictly necessary. Here, the matrix is surrounded at its surface by a cage (143) that is embedded in but projects just above the surface of the matrix (140) to enhance its retention properties at the outset. As the matrix (140) degrades, it remains within the confines of the cage (143) until the matrix (140) fragments become small enough to extrude through the openings in the cage (143). Other retention and degradation properties are similar to those outlined above.

Benefits of The Present Invention

Unique to the present invention, the combination of the minimally invasive anterior keyhole approach, the described guide-free drug placement devices, and the absence of any retained reservoir allow surgeons to consider several new uses for targeted therapeutic agents:

1. Surgeons will have a reasonable intermediate option between pure oral medical therapy and even minimally invasive ostial dilation procedures. A patient that failed several standard oral medical regimens might reasonably opt to have in-office placement of pharmaceuticals via the described approach. Such an option may have a substantial chance of succeeding where oral therapy failed and without even resorting to minimally invasive surgical options of the prior art or of the present invention.
2. As an adjunct to minimally invasive or routine sinus surgery of the prior art or of the present invention, in lieu of oral or other topical agents that are generally given in the context of sinus surgery.
3. The treatment of postoperative patients regardless of the surgical method used to treat them. This flexibility is quite valuable in that many postoperative patients will need further medical therapy on a repeated basis over the long term. For such patients, the major advantage of the method of the present invention is that it allows simple in-office treatment of the problem with a lower anticipated side-effect profile than typical for oral agents, and with a vehicle that mimics the cost structure and simplicity of administration of those oral agents, unlike any option available in the prior art.

The invention claimed is:

1. A method of treating a congested maxillary sinus comprising:
   advancing an instrument capable of making a perforation into the ethmoid infundibulum;
   positioning the instrument at the anterior and inferior attachment of the uncinate process;
   advancing the instrument into a posterior opening of an ethmoid infundibulum superior to a pathway of mucus exit from a posterior ethmoid infundibulum;
   assessing a location of the anterior and inferior attachment of the uncinate process;
   making a perforation in the uncinate process while minimizing a creation of flail segments, wherein the perforation is neither enlarged nor utilized as a new drainage pathway;
   inserting a dilator through the perforation;
   positioning the dilator in the ethmoid infundibulum; and
   dilating the ethmoid infundibulum by expanding the dilator.

2. The method of claim 1, further comprising:
   advancing the dilator into the natural ostium of the maxillary sinus; and
   dilating the natural ostium of the maxillary sinus by expanding the dilator.

3. The method of claim 1, wherein the dilator is a guide-free dilator.

4. The method of claim 1, wherein the instrument capable of making a perforation is a backbiting hole punch.

5. The method of claim 1, wherein the skeletal support structure of the uncinate process is maintained after making the perforation.

6. The method of claim 1, wherein the perforation has a diameter of about 3 mm.

7. The method of claim 1 wherein the dilator contains a balloon.

8. The method of claim 7, wherein the balloon has an ellipsoid or figure-8 configuration.

9. A method of treating a congested maxillary sinus comprising:
   retracting the middle turbinate;
   advancing an instrument capable of making a perforation into the ethmoid infundibulum;
   positioning the instrument at the anterior and inferior attachment of the uncinate process;
   advancing the instrument into a posterior opening of an ethmoid infundibulum superior to a pathway of mucus exit from a posterior ethmoid infundibulum;
   assessing a location of the anterior and inferior attachment of the uncinate process;
   making a perforation in the uncinate process wherein the perforation is neither enlarged nor utilized as a new drainage pathway;
   inserting a dilator through the perforation;
   positioning the dilator in the ethmoid infundibulum; and
   dilating the ethmoid infundibulum by expanding the dilator.

10. A method of treating a congested maxillary sinus comprising:
    advancing an instrument into a posterior opening of an ethmoid infundibulum superior to a pathway of mucus exit from a posterior ethmoid infundibulum;
    assessing a location of the anterior and inferior attachment of the uncinate process;
    making a perforation in the uncinate process wherein the perforation is used as a conduit through which other structures beyond the perforation can be accessed;
    inserting a dilator through the perforation;
    dilating the ethmoid infundibulum by expanding the dilator.

11. The method of claim 9, further comprising:
    advancing the dilator into the natural ostium of the maxillary sinus; and
    dilating the natural ostium of the maxillary sinus by expanding the dilator.

12. The method of claim 10, further comprising:
    advancing the dilator into the natural ostium of the maxillary sinus; and
    dilating the natural ostium of the maxillary sinus by expanding the dilator.

13. A method of treating a congested maxillary sinus comprising:
    advancing an instrument into a posterior opening of an ethmoid infundibulum superior to a pathway of mucus exit from a posterior ethmoid infundibulum;
    assessing a location of the anterior and inferior attachment of the uncinate process;
    retracting the middle turbinate;
    advancing an instrument capable of making a perforation into the ethmoid infundibulum;
    positioning the instrument at the anterior and inferior attachment of the uncinate process;

making a perforation in the uncinate process while preserving structural support of the uncinate process, wherein the perforation is neither enlarged nor utilized as a new drainage pathway;
inserting a dilator through the perforation;
positioning the dilator in the ethmoid infundibulum; and
dilating the ethmoid infundibulum by expanding the dilator.

14. The method of claim 13, further comprising:
advancing the dilator into the natural ostium of the maxillary sinus; and
dilating the natural ostium of the maxillary sinus by expanding the dilator.

15. A method of treating a congested maxillary sinus comprising:
advancing an instrument into a posterior opening of an ethmoid infundibulum superior to a pathway of mucus exit from a posterior ethmoid infundibulum;
assessing a location of the anterior and inferior attachment of the uncinate process;
positioning the instrument at the anterior and inferior attachment of the uncinate process;
making a perforation in the uncinate process without removing tissue from the uncinate process, wherein the perforation is neither enlarged nor utilized as a new drainage pathway;
inserting a dilator through the perforation;
positioning the dilator in the ethmoid infundibulum; and
dilating the ethmoid infundibulum by expanding the dilator.

16. The method of claim 15, further comprising:
advancing the dilator into the natural ostium of the maxillary sinus; and
dilating the natural ostium of the maxillary sinus by expanding the dilator.

* * * * *